US007388019B2

(12) United States Patent
Ashton et al.

(10) Patent No.: US 7,388,019 B2
(45) Date of Patent: Jun. 17, 2008

(54) 3-AMINO-4-PHENYLBUTANOIC ACID DERIVATIVES AS DIPEPTIDYL PEPTIDASE INHIBITORS FOR THE TREATMENT OR PREVENTION OF DIABETES

(75) Inventors: Wallace T. Ashton, Edison, NJ (US); Charles G. Caldwell, Scotch Plains, NJ (US); Joseph L. Duffy, Cranford, NJ (US); Robert J. Mathvink, Red Bank, NJ (US); Liping Wang, Dayton, NJ (US); Ann E. Weber, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 321 days.

(21) Appl. No.: 10/542,694

(22) PCT Filed: Jan. 27, 2004

(86) PCT No.: PCT/US2004/002309

§ 371 (c)(1),
(2), (4) Date: Jul. 19, 2005

(87) PCT Pub. No.: WO2004/069162

PCT Pub. Date: Aug. 19, 2004

(65) Prior Publication Data

US 2006/0074087 A1 Apr. 6, 2006

Related U.S. Application Data

(60) Provisional application No. 60/444,145, filed on Jan. 31, 2003.

(51) Int. Cl.
*C07D 471/04* (2006.01)
*A61K 31/4375* (2006.01)
*A61P 3/10* (2006.01)
*C07D 487/04* (2006.01)
*A61K 31/4985* (2006.01)
*A61K 31/5025* (2006.01)
*A61K 31/519* (2006.01)
*A61K 31/53* (2006.01)

(52) U.S. Cl. ............... 514/300; 546/122; 544/179; 544/180; 544/184; 544/239; 544/279; 544/350; 514/241; 514/243; 514/252.03; 514/249; 514/266.1

(58) Field of Classification Search ........... 546/122; 514/300
See application file for complete search history.

(56) References Cited

U.S. PATENT DOCUMENTS

| 4,386,090 | A | 5/1983 | Moinet et al. |
| 5,939,560 | A | 8/1999 | Jenkins et al. |
| 6,011,155 | A | 1/2000 | Villhauer |
| 6,166,063 | A | 12/2000 | Villhauer |
| 6,303,661 | B1 | 10/2001 | Demuth et al. |
| 6,432,969 | B1 | 8/2002 | Villhauer |
| 6,699,871 | B2 | 3/2004 | Edmondson et al. |

FOREIGN PATENT DOCUMENTS

| WO | WO 97/40832 | 11/1997 |
| WO | WO 98/19998 | 5/1998 |
| WO | WO 98/19998 A2 | 5/1998 |
| WO | WO 98/19998 A3 | 5/1998 |
| WO | WO 00/34241 | 6/2000 |
| WO | WO 01/34594 A1 | 5/2001 |
| WO | WO 01/42262 | 6/2001 |
| WO | WO 01/42262 A2 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 2005/002530 A2 | 1/2003 |
| WO | WO 03/082817 A2 | 10/2003 |
| WO | WO 2004/007468 | 1/2004 |
| WO | WO 2004/007468 A1 | 1/2004 |

(Continued)

OTHER PUBLICATIONS

J. J. Holst, "Treatment of Type 2 Diabetes Mellitus with Agonists of the GLP-1 Receptor or DPP-IV Inhibitors", Expert Opin. Emerg. Drugs, vol. 9(1) pp. 155-166, 2004.
C. F. Deacon, et al., "Inhibitors of dipeptidyl peptidase IV: A Novel Approach for the Prevention and Treatment of Type 2 Diabetes?", Expert Opin. Investig. Drugs, vol. 13(9) pp. 1091-1102, 2004.
K. Augustyns et al., "Dipeptidyl Peptidase IV Inhibitors as New Therapeutic Agents for the Treatment of Type 2 Diabetes", Expert Opin. Ther. Patents, vol. 13(4), pp. 499-510, 2003.
Novartis AG: WO0034241, "Novel N-substituted-2-Cyanopyrrolidines as Potent Inhibitors of Dipeptidyl Peptidase IV in the Treatment of Non-Insulin-Dependent Diabetes Mellitus", Exp. Opin. Ther. Patents, vol. 10(12), pp. 1937-1942, 2000.

(Continued)

*Primary Examiner*—Venkataraman Balasubram
(74) *Attorney, Agent, or Firm*—Philippe L. Durette; Catherine D. Fitch

(57) ABSTRACT

The present invention is directed to 3-amino-4-phenylbutanoic acid derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

24 Claims, No Drawings

FOREIGN PATENT DOCUMENTS

| | | |
|---|---|---|
| WO | WO 2004/032836 A2 | 4/2004 |
| WO | WO 2004/043940 | 5/2004 |
| WO | WO 2004/043940 A1 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 | 12/2004 |
| WO | WO 2004/110436 A1 | 12/2004 |
| WO | WO 2004/112701 A2 | 12/2004 |
| WO | WO 2004/112701 A3 | 12/2004 |
| WO | WO 2005/011581 A2 | 2/2005 |
| WO | WO 2005/044195 A2 | 5/2005 |
| WO | WO 2005/056003 A1 | 6/2005 |
| WO | WO 2005/056013 A1 | 6/2005 |

OTHER PUBLICATIONS

O. J. Orucker, "Therapeutic potential of dipeptidyl peptidase IV inhibitors for the treatment of type 2 diabetes", Exp. Opin Invest. Drugs, vol. 12, 2004, pp. 87-100.

T. P. Vahl & D. A. D'Alessio, "Gut peptides in the treatment of diabetes mellitus" Exp. Opin. Invest. Drugs, vol. 13, 2004, pp. 177-188.

L. B. Knudsen, "Glucagon-like peptide-1: The Basis of a New Class of Treatment for Type 2 Diabetes", J. Med. Chem, vol. 47, 2004, pp. 4128-4134.

Ann E. Weber, "Dipeptidyl Peptidase IV Inhibitors for the Treatment of Diabetes", J. Med. Chem, vol. 47, 2004, pp. 4135-4141.

J. J. Holst and C. F. Deacon, "Glucagon-like peptide 1 and inhibitors of dipeptidyl IV in the treatment of type 2 diabetes mellitus", Curr. Opin Pharmacology, vol. 4, 2004, pp. 589-596.

C. F. Deacon, "Perspectives in Diabetes—Therapeutic Strategies Based on Glucagon-Like Peptide 1", Diabetes, vol. 53, Sep. 2004, pp. 2181-2189.

Augustyns, K, et al., "Dipeptidyl peptidase IV inhibitors as new therapeutic agents for the treatment of Type 2 diabetes", Expert Opin. Ther. Patents, vol. 13, No. 4, pp. 499-510, 2003.

Deacon, C.F., "*Perspectives in Diabetes*—Therapeutic Strategies Based on Glucagon-Like Peptide 1", Diabetes, vol. 53, pp. 2181-2189, 2004.

Deacon, C. F. et al., "Inhibitors of dipeptidyl peptidase IV: a novel approach for the prevention and treatment of Type 2 diabetes?", Expert Opin. Investig. Drugs, vol. 13, No. 9, pp. 1091-1102, 2004.

Drucker, D . J., "Therapeutic Potential of dipeptidyl peptidase IV inhibitors for the treatment of type 2 diabetes", Expert Opin. Investig. Drugs, vol. 12, No. 1, pp. 87-100, 2003.

Holst, J. J., "Treatment of Type 2 diabetes mellitus with agonists of the GLP-1 receptor or DPP-IV inhibitors", Expert Opin. Emerg. Drugs, vol. 9, No. 1, pp. 155-166, 2004.

Holst, J. J. et al., "Glucagon-like peptide 1 and inhibitors of dipeptidyl peptidase IV in the treatment of type 2 diabetes mellitus", Current Opinion in Pharmacology, vol. 4, pp. 589-596, 2004.

Knudsen, L. B., "Glucagon-like Peptide-1: The Basis of a New Class of Treatment for Type 2 Diabetes",J. Med. Chem, vol. 47, pp. 4128-4134, 2004.

Novartis AG: WO0034241—"Novel N-substituted-2-cyanopyrrolidines as potent inhibitors of dipeptidyl peptidase IV in the treatment of non-insulin-depentdent diabetes mellitus", Exp. Opin. Ther. Patents, vol. 10, No. 12, pp. 1937-1942, 2000.

Vahl, T. P. et al., "Gut peptides in the treatment of diabetes mellitus", Expert Opin. Investig. Drugs, vol. 13, No. 3, pp. 177-188, 2004.

Weber, A. E., "Dipeptidyl Peptidase IV Inhibitors for the Treatment of Diabetes", J. Med. Chem, vol. 47, pp. 4135-4141, 2004.

3-AMINO-4-PHENYLBUTANOIC ACID DERIVATIVES AS DIPEPTIDYL PEPTIDASE INHIBITORS FOR THE TREATMENT OR PREVENTION OF DIABETES

CROSS REFERENCE TO RELATED APPLICATIONS

This application is the National Stage of International Application No. PCT/US04/002309, filed 27 Jan. 2004, which claims the benefit under 35 U.S.C. 119(e) of U.S. Provisional Application No. 60/444,145 filed 31 Jan. 2003.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, *Bioorg. Med. Chem. Lett.*, 6: 1163-1166 (1996); and *Bioorg. Med. Chem. Lett.* 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to 3-amino-4-phenylbutanoic acid derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to 3-amino-4-phenylbutanoic acid derivatives useful as inhibitors of dipeptidyl peptidase-IV. Compounds of the present invention are described by structural formula I:

(I)

or a pharmaceutically acceptable salt thereof; wherein each n is independently 0, 1, or 2;
  W, X, Y, and Z are each independently N or $CR^1$;
  with the provisos that at least one of W, X, Y and Z is $CR^1$, and when W and Y are N, then one of X and Z is N;
  Ar is phenyl substituted with one to five $R^2$ substituents;
  each $R^1$ is independently selected from the group consisting of
    hydrogen,
    halogen,
    hydroxy,
    cyano,
    $C_{1-10}$ alky, wherein alkyl is unsubstituted or substituted with one to five substituents independently selected from halogen or hydroxy,
    $C_{1-10}$ alkoxy, wherein alkoxy is unsubstituted or substituted with one to five substituents independently selected from halogen or hydroxy,
    $C_{1-10}$ alkylthio, wherein alkylthio is unsubstituted or substituted with one to five substituents independently selected from halogen or hydroxy,
    $C_{2-10}$ alkenyl, wherein alkenyl is unsubstituted or substituted with one to five substituents independently selected from halogen, hydroxy, COOH, and $COOC_{1-6}$alkyl,
    $(CH_2)_n COOH$,
    $(CH_2)_n COOC_{1-6}$ alkyl,
    $(CH_2)_n CONR^3R^4$, wherein $R^3$ and $R^4$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, $C_{1-6}$ alkoxy, $(CH_2)_n COOH$, and $(CH_2)_n COOC_{1-6}$ alkyl, wherein alkyl and alkoxy are unsubstituted or substituted with one to five halogens;
    or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOH$, $(CH_2)_n COOC_{1-6}$ alkyl, $C_{1-6}$ alkyl, and $C_{1-6}$ alkoxy, wherein alkyl and alkoxy are unsubstituted or substituted with phenyl or one to five halogens;
    $(CH_2)_n$—$NR^3R^4$,
    $(CH_2)_n$—$OCONR^3R^4$,
    $(CH_2)_n$—$SO_2NR^3R^4$,
    $(CH_2)_n$—$SO_2R^5$,
    $(CH_2)_n$—$NR^6SO_2R^5$,
    $(CH_2)_n$—$NR^6CONR^3R^4$,
    $(CH_2)_n$—$NR^6COR^6$,
    $(CH_2)_n$—$NR^6CO_2R^5$,
    $(CH_2)_n$—$COR^6$,
    $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
    $(CH_2)_n$-aryl, wherein aryl is unsubstituted or substituted with one to five substituents independently selected from halogen, cyano, hydroxy, $NR^6SO_2R^5$, $SO_2R^5$, $CO_2H$, $COOC_{1-6}$ alkyl, $C_{1-6}$ alkyl, and $C_{1-6}$ alkoxy, wherein alkyl and alkoxy are unsubstituted or substituted with one to five halogens,
    $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
    $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
    wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens;
  each $R^2$ is independently selected from the group consisting of
    hydrogen,
    halogen,
    cyano,
    hydroxy,
    $C_{1-6}$ alkyl, unsubstituted or substituted with one to five halogens, and
    $C_{1-6}$ alkoxy, unsubstituted or substituted with one to five halogens;
  each $R^5$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene (CH$_2$) carbon atom in R$^5$ is unsubstituted or substituted with one to two groups independently selected from halogen, hydroxy, C$_{1-4}$ alkyl, and C$_{1-4}$ alkoxy, wherein alkyl and alkoxy are unsubstituted or substituted with one to five halogens;

each R$^6$ is hydrogen or R$^5$;

R$^7$, R$^8$, and R$^9$ are each independently selected from the group consisting of hydrogen, cyano, (CH$_2$)$_n$COOH, (CH$_2$)$_n$COOC$_{1-6}$ alkyl, C$_{1-10}$ alkyl, unsubstituted or substituted with one to five substituents independently selected from halogen, hydroxy, C$_{1-6}$ alkoxy, and phenyl-C$_{1-3}$ alkoxy, wherein alkoxy is unsubstituted or substituted with one to five halogens, (CH$_2$)$_n$-aryl, wherein aryl is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens, (CH$_2$)$_n$-heteroaryl, wherein heteroaryl is unsubstituted or substituted with one to three substituents independently selected from hydroxy, halogen, C$_{1-6}$ alkyl, and C$_{1-6}$ alkoxy, wherein alkyl and alkoxy are unsubstituted or substituted with one to five halogens, (CH$_2$)$_n$-heterocyclyl, wherein heterocyclyl is unsubstituted or substituted with one to three substituents independently selected from oxo, hydroxy, halogen, C$_{1-6}$ alkyl, and C$_{1-6}$ alkoxy, wherein alkyl and alkoxy are unsubstituted or substituted with one to five halogens, (CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens, and (CH$_2$)$_n$CONR$^3$R$^4$, wherein R$^3$ and R$^4$ are independently selected from the group consisting of hydrogen, tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, C$_{1-6}$ alkoxy, (CH$_2$)$_n$COOH, and (CH$_2$)$_n$COOC$_{1-6}$ alkyl, wherein alkyl and alkoxy are unsubstituted or substituted with one to five halogens;

or R$^3$ and R$^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, (CH$_2$)$_n$COOH, (CH$_2$)$_n$COOC$_{1-6}$ alkyl, C$_{1-6}$ alkyl, and C$_{1-6}$ alkoxy, wherein alkyl and alkoxy are unsubstituted or substituted with phenyl or one to five halogens; and wherein any methylene (CH$_2$) carbon atom in R$^7$, R$^8$ or R$^9$ is unsubstituted or substituted with one to two groups independently selected from halogen, hydroxy, and C$_{1-4}$ alkyl unsubstituted or substituted with one to five halogens.

In one embodiment of the compounds of the present invention, the carbon atom marked with an * has the R stereochemical configuration as depicted in formula Ia

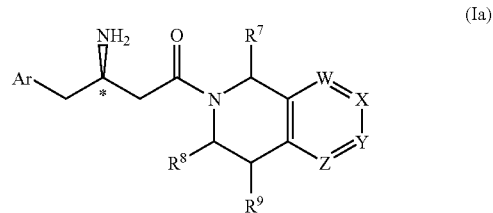

wherein Ar, W, X, Y, Z, R$^7$, R$^8$, and R$^9$ are as defined herein.

In a second embodiment of the compounds of the present invention, W, X, Y, and Z are CR$^1$ as depicted in formula Ib:

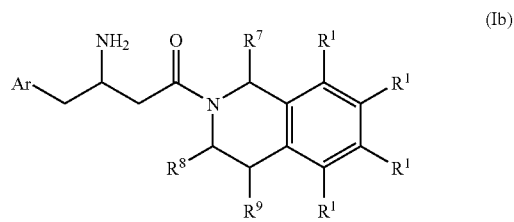

wherein Ar, R$^1$, R$^7$, R$^8$, and R$^9$ are as defined herein.

In a class of this second embodiment, the carbon atom marked with an * has the R stereochemical configuration as depicted in formula Ic:

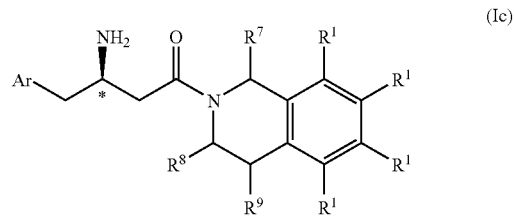

wherein Ar, R$^1$, R$^7$, R$^8$, and R$^9$ are as defined herein.

In another class of this second embodiment of the compounds of the present invention, R$^7$ and R$^9$ are hydrogen as depicted in formula Id:

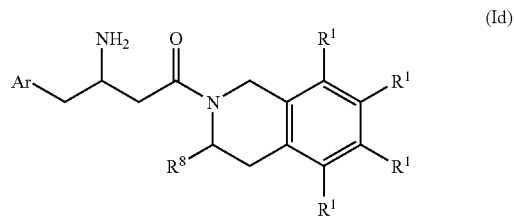

wherein Ar, R$^1$, and R$^8$ are as defined herein.

In a subclass of this class, R$^8$ is CONR$^3$R$^4$ or hydrogen.

In a third embodiment of the compounds of the present invention, W, X, and Y are CR$^1$ and Z is N as depicted in formula Ie:

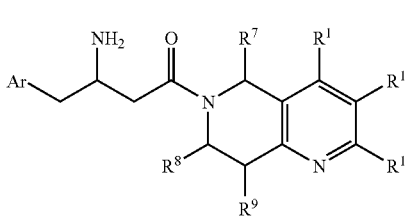

(Ie)

wherein Ar, $R^1$, $R^7$, $R^8$, and $R^9$ are as defined herein.

In a class of this third embodiment, the carbon atom marked with an * has the R stereochemical configuration as depicted in formula If:

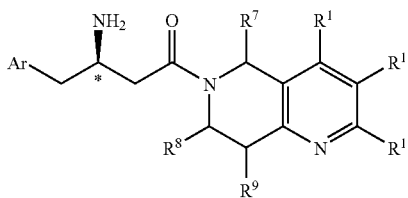

(If)

wherein Ar, $R^1$, $R^7$, $R^8$, and $R^9$ are as defined herein.

In another class of this third embodiment of the compounds of the present invention, $R^8$ and $R^9$ are hydrogen as depicted in formula Ig:

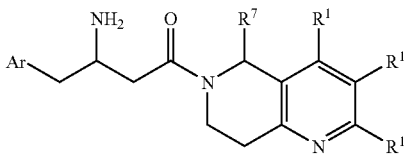

(Ig)

wherein Ar, $R^1$, and $R^7$ are as defined herein.

In a subclass of this class, $R^7$ is hydrogen.

In a fourth embodiment of the compounds of the present invention, W, X, and Z are $CR^1$, and Y is N as depicted in formula Ih:

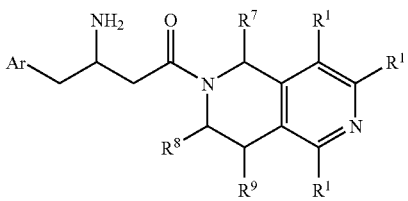

(Ih)

wherein Ar, $R^1$, $R^7$, $R^8$, and $R^9$ are as defined herein.

In a class of this fourth embodiment, the carbon atom marked with an * has the R stereochemical configuration as depicted in formula Ii:

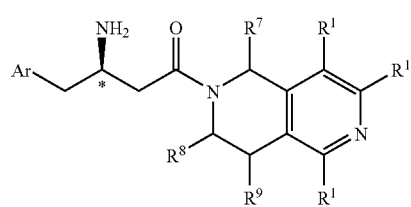

(Ii)

wherein Ar, $R^1$, $R^7$, $R^8$, and $R^9$ are as defined herein.

In another class of this fourth embodiment of the compounds of the present invention, $R^8$ and $R^9$ are hydrogen as depicted in formula Ij:

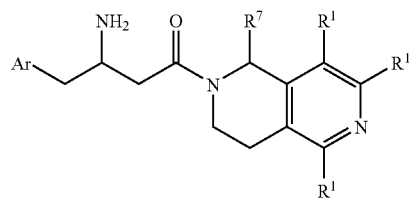

(Ij)

wherein Ar, $R^1$, and $R^7$ are as defined herein.

In a subclass of this class, $R^7$ is hydrogen.

In a fifth embodiment of the compounds of the present invention, W is N, and X, Y, and Z are $CR^1$ as depicted in formula Ik:

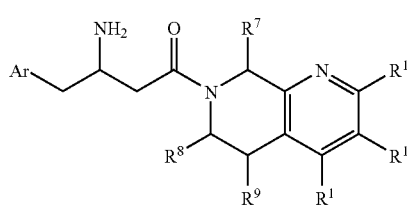

(Ik)

wherein Ar, $R^1$, $R^7$, $R^8$, and $R^9$ are as defined herein.

In a class of this fifth embodiment, the carbon atom marked with an * has the R stereochemical configuration as depicted in formula Il:

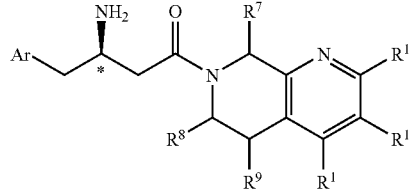

(Il)

wherein Ar, $R^1$, $R^7$, $R^8$, and $R^9$ are as defined herein.

In another class of this fifth embodiment of the compounds of the present invention, $R^8$ and $R^9$ are hydrogen as depicted in formula Im:

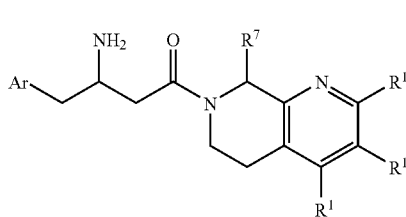

(Im)

wherein Ar,¹, R¹, and R⁷ are as defined herein.

In a subclass of this class, R⁷ is hydrogen.

In a sixth embodiment of the compounds of the present invention, W is CR¹, X is N, Y is CR¹, and Z is N as depicted in formula In:

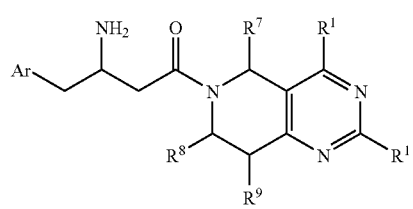

(In)

wherein Ar, R¹, R⁷, R⁸, and R⁹ are as defined herein.

In a class of this sixth embodiment, the carbon atom marked with an * has the R stereochemistry configuration as depicted in formula Io:

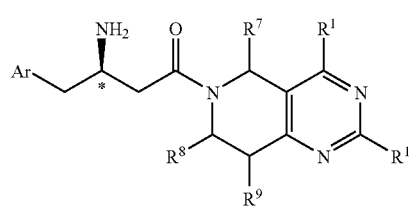

(Io)

wherein Ar, R¹, R⁷, R⁸, and R⁹ are as defined herein.

In another class of this sixth embodiment of the compounds of the present invention, R⁸ and R⁹ are hydrogen as depicted in formula Ip:

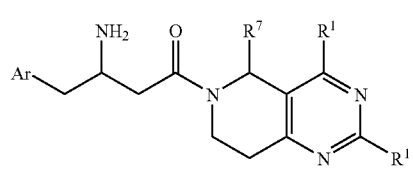

(Ip)

wherein Ar, R¹, and R⁷ are as defined herein.

In a subclass of this class, R⁷ is hydrogen.

In a seventh embodiment of the compounds of the present invention, W is N, X and Y are CR¹, and Z is N as depicted in formula Iq:

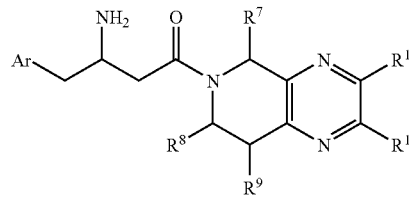

(Iq)

wherein Ar, R¹, R⁷, R⁸, and R⁹ are as defined herein.

In a class of this seventh embodiment, the carbon atom marked with an * has the R stereochemistry configuration as depicted in formula Ir:

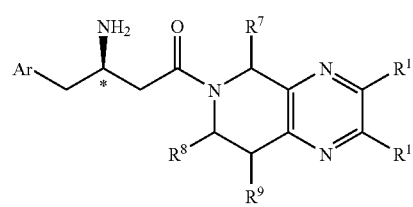

(Ir)

wherein Ar, R¹, R⁷, R⁸, and R⁹ are as defined herein.

In another class of this seventh embodiment of the compounds of the present invention, R⁸ and R⁹ are hydrogen as depicted in formula Is:

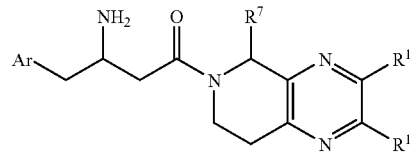

(Is)

wherein Ar, R¹, and R⁷ are as defined herein.

In a subclass of this class, R⁷ is hydrogen.

In an eighth embodiment of the compounds of the present invention, W and X are N, and Y and Z are CR¹ as depicted in formula It:

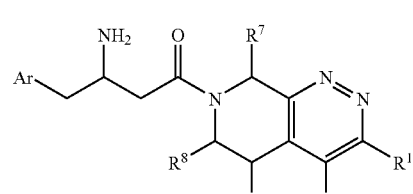

(It)

wherein Ar, R¹, R⁷, R⁸, and R⁹ are as defined herein.

In a class of this eighth embodiment, the carbon atom marked with an * has the R stereochemistry configuration as depicted in formula Iu:

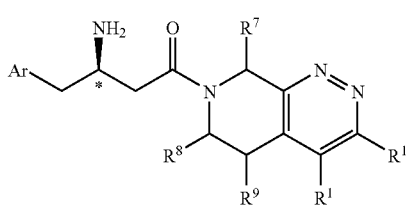

wherein Ar, $R^1$, $R^7$, $R^8$, and $R^9$ are as defined herein.

In another class of this eighth embodiment of the compounds of the present invention, $R^8$ and $R^9$ are hydrogen as depicted in formula Iv:

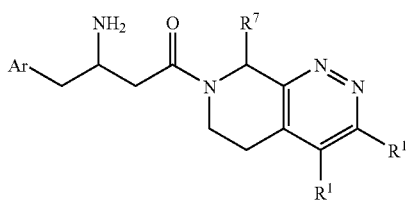

wherein Ar, $R^1$, and $R^7$ are as defined herein.

In a subclass of this class, $R^7$ is hydrogen.

In a ninth embodiment of the compounds of the present invention, W, X, and Z are N, and Y is $CR^1$ as depicted in formula Iw:

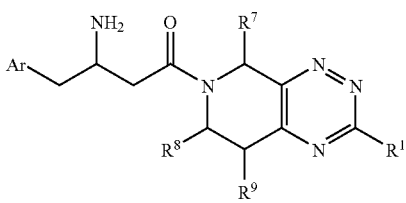

wherein Ar, $R^1$, $R^7$, $R^8$, and $R^9$ are as defined herein.

In a class of this ninth embodiment, the carbon atom marked with an * has the R stereochemical configuration as depicted in formula Ix:

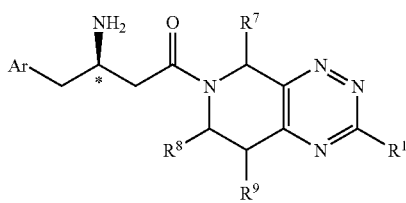

wherein Ar, $R^1$, $R^7$, $R^8$, and $R^9$ are as defined herein.

In another class of this ninth embodiment of the compounds of the present invention, $R^8$ and $R^9$ are hydrogen as depicted in formula Iy:

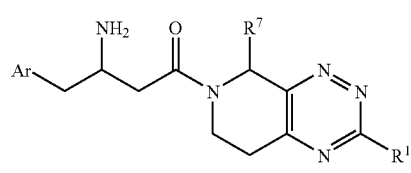

wherein Ar, $R^1$, and $R^7$ are as defined herein.

In a subclass of this class, $R^7$ is hydrogen.

In a tenth embodiment of the compounds of the present invention, W, Y, and Z are N, and X is $CR^1$ as depicted in formula Iz:

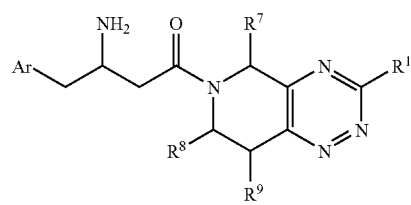

wherein Ar, $R^1$, $R^7$, $R^8$, and $R^9$ are as defined herein.

In a class of this tenth embodiment, the carbon atom marked with an * has the R stereochemical configuration as depicted in formula Iaa:

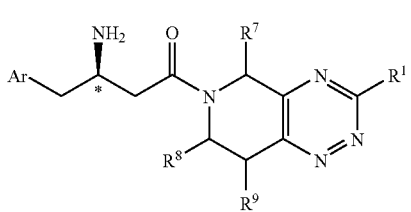

wherein Ar, $R^1$, $R^7$, $R^8$, and $R^9$ are as defined herein.

In another class of this tenth embodiment of the compounds of the present invention, $R^8$ and $R^9$ are hydrogen as depicted in formula Iab:

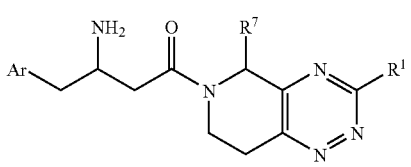

wherein Ar, $R^1$, and $R^7$ are as defined herein.

In a subclass of this class, $R^7$ is hydrogen.

In an eleventh embodiment of the compounds of the present invention, $R^2$ is selected from the group consisting of hydrogen, fluoro, chloro, bromo, trifluoromethyl, and methyl. In a class of this embodiment, $R^2$ is selected from the group consisting of hydrogen, fluoro, and chloro. In a subclass of this class, $R^2$ is hydrogen or fluoro.

In a twelfth embodiment of the compounds of the present invention, $R^1$ is selected from the group consisting of:
  hydrogen,
  halogen,
  hydroxy,
  cyano,
  $C_{1-10}$ alkyl, wherein alkyl is unsubstituted or substituted with one to five substituents independently selected from halogen or hydroxy,
  $C_{1-10}$ alkoxy, wherein alkoxy is unsubstituted or substituted with one to five substituents independently selected from halogen or hydroxy,
  $(CH_2)_n COOH$,
  $(CH_2)_n COOC_{1-6}$ alkyl,
  $(CH_2)_n CONR^3 R^4$, wherein $R^3$ and $R^4$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alky, $C_{1-6}$ alkoxy, $(CH_2)_n COOH$, and $(CH_2)_n COOC_{1-6}$ alkyl, wherein alkyl and alkoxy are unsubstituted or substituted with one to five halogens;
  or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOC_{1-6}$ alkyl, $C_{1-6}$ alkyl, and $C_{1-6}$ alkoxy, wherein alkyl and alkoxy are unsubstituted or substituted with phenyl or one to five halogens;
  $(CH_2)_n$—$SO_2 NR^3 R^4$,
  $(CH_2)_n$—$NR^6 SO_2 R^5$,
  $(CH_2)_n$—$NR^6 COR^6$,
  $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
  $(CH_2)_n$-aryl, wherein aryl is unsubstituted or substituted with one to five substituents independently selected from halogen, cyano, hydroxy, $NR^6 SO_2 R^5$, $SO_2 R^5$, $CO_2 H$, $COOC_{1-6}$ alkyl, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $C_{1-6}$ alkyd, and $C_{1-6}$ alkoxy, wherein alkyl and alkoxy are unsubstituted or substituted with one to five halogens, and
  wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^1$ is selected from the group consisting of
  hydrogen,
  methyl,
  trifluoromethyl,
  phenyl,
  4-fluorophenyl,
  cyclopropyl,
  chloro,
  methoxy,
  hydroxy,
  cyano,
  methoxycarbonyl,
  ethoxycarbonyl,
  tert-butylaminocarbonyl,
  carboxy,
  acetamido,
  methanesulfonylamino,
  benzenesulfonylamino,
  aminosulfonyl, and
  5-(trifluoromethyl)oxadiazol-3-yl.

In a thirteenth embodiment of the compounds of the present invention, $R^7$, $R^8$, and $R^9$ are independently selected from the group consisting of:
  hydrogen,
  $C_{1-10}$ alkyl, unsubstituted or substituted with one to five substituents independently selected from halogen, hydroxy, $C_{1-6}$ alkoxy, and phenyl-$C_{1-3}$ alkoxy, wherein alkoxy is unsubstituted or substituted with one to five halogens, and
  $(CH_2)_n CONR^3 R^4$, wherein $R^3$ and $R^4$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, $C_{1-6}$ alkoxy, $(CH_2)_n COOH$, and $(CH_2)_n COOC_{1-6}$ alkyl, wherein alkyl and alkoxy are unsubstituted or substituted with one to five halogens;
  or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOC_{1-6}$ alkyl, $C_{1-6}$ alkyl, and $C_{1-6}$ alkoxy, wherein alkyl and alkoxy are unsubstituted or substituted with phenyl or one to five halogens; and
  wherein any methylene ($CH_2$) carbon atom in $R^7$, $R^8$ or $R^9$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^7$, $R^8$, and $R^9$ are each independently selected from the group consisting of
  hydrogen,
  methyl,
  ethyl,
  [[4-(carboxymethyl)phenyl]methyl]aminocarbonyl,
  pyrrolidin-1-ylcarbonyl,
  piperidin-1-ylcarbonyl,
  4-[(methoxycarbonyl)methyl]benzylaminocarbonyl, and
  4-[(benzyloxy)carbonyl]piperazin-1-ylcarbonyl.

In a subclass of this class, $R^7$ and $R^9$ are hydrogen.

In a further subclass of this class, $R^8$ and $R^9$ are hydrogen. In a subclass of this subclass, $R^7$ is hydrogen.

Illustrative, but nonlimiting, examples of compounds of the present invention that are useful as dipeptidyl peptidase-IV inhibitors are the following:

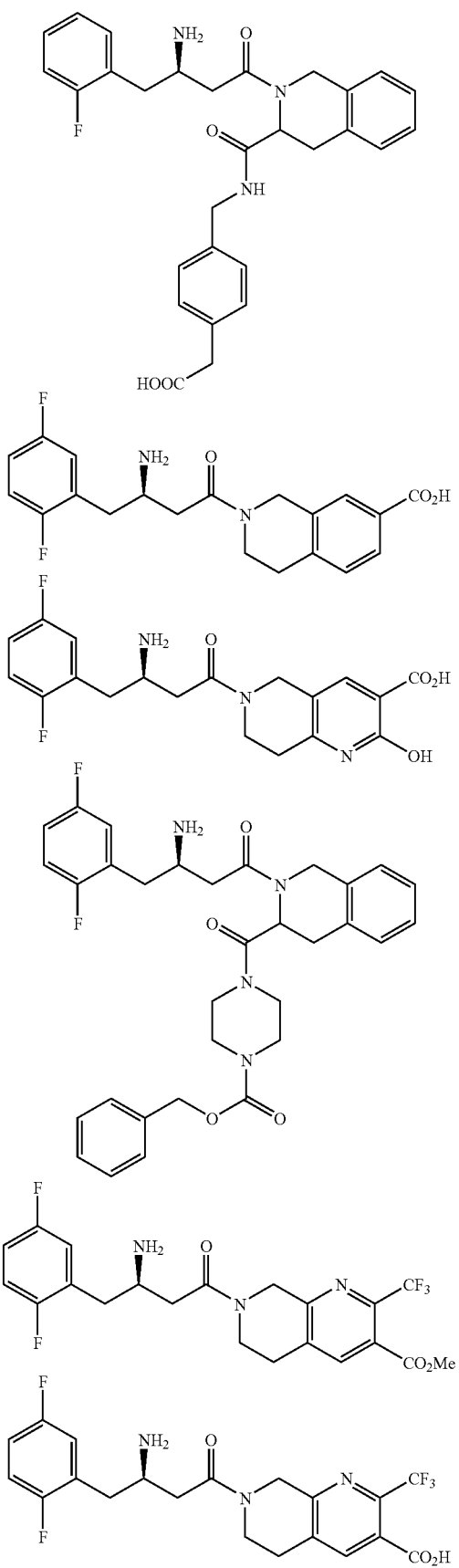

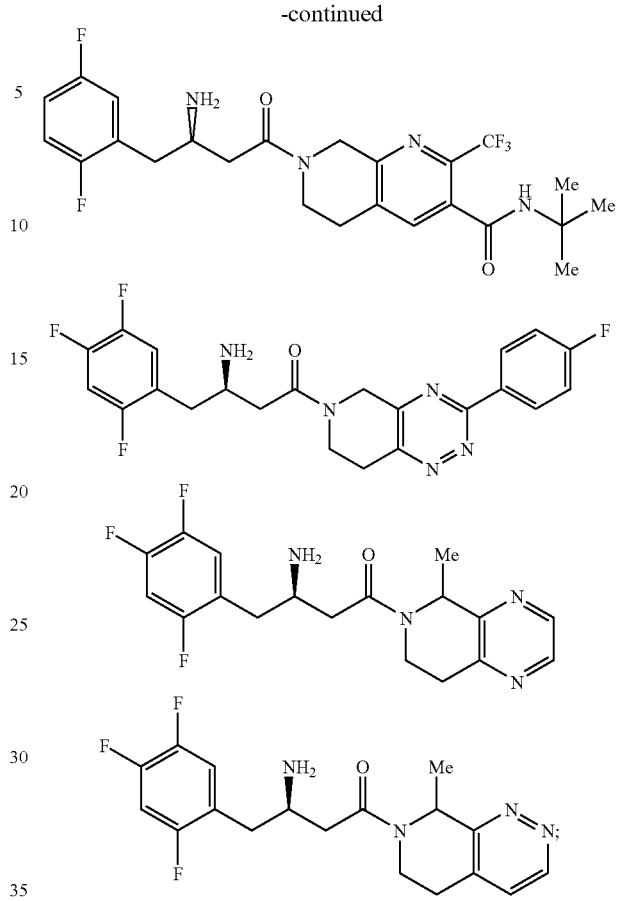

or a pharmaceutically acceptable salt thereof.

As used herein the following definitions are applicable.

"Alkyl" well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention may contain one or more asymmetric centers and can thus occur as racemates and racemic mixtures, single enantiomers, diastereomeric mixtures and individual diastereomers. The compounds of the present invention have one asymmetric center at the carbon atom marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m=50$ μM; $k_{cat}=75\ s^{-1}$; $k_{cat}/K_m=1.5\times10^6\ M^{-1}s^{-1}$. A typical reaction contains approximately 50 pM enzyme, 50 μM Gly-Pro-AMC, and buffer (100 mM HEPES, pH 7.5, 0.1 mg/ml BSA) in a total reaction volume of 100 μl. Liberation of AMC is monitored continuously in a 96-well plate fluorometer using an excitation wavelength of 360 nm and an emission wavelength of 460 nm. Under these conditions, approximately 0.8 μM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 μM. Such a result is indicative of the intrinsic activity of the compounds in use as inhibitors of the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis. The DP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DP-IV inhibitors may also be useful to treat hypertension associated with this condition.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine*, 6: 802-807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DP-IV inhibitor diprotin A; and (3) GRF[344] is found in the plasma of a human GRF transgenic pig (*J. Clin. Invest.*, 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides*. 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosuppressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation* 63: 1495-1500 (1997)). DP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DP-IV is upregulated in a number of autoimmune diseases including rheumatoid arthritis, multiple sclerosis, Graves' disease, and Hashimoto's thyroiditis (*Immunology Today* 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ $M^{-1}s^{-1}$ or greater. In an electric shock jump test model of analgesia in rats, a DP-IV inhibitor showed a significant effect that was independent of the presence of exogenous endomorphin-2 (*Brain Research*, 815: 278-286 (1999)). Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety

Rats naturally deficient in DP-IV have an anxiolytic phenotype (WO 02/34243; Karl et al., *Physiol. Behav.* 2003). DP-IV deficient mice also have an anxiolytic phenotype using the Porsolt and light/dark models. Thus DP-IV inhibitors may prove useful for treating anxiety and related disorders.

Memory and Cognition

GLP-1 agonists are active in models of learning (passive avoidance, Morris water maze) and neuronal injury kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DP-IV inhibitors are expected to show similar effects.

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.* 30: 333-338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV ODP-IV) inhibitors;

(b) insulin sensitizers including (i) PPARγ agonists such as the glitazones (e.g. troglitazone, pioglitazone, englitazone, MCC-555, rosiglitazone, balaglitazone, and the like) and other PPAR ligands, including PPARα/γ dual agonists, such as KRP-297 and muraglitazar, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepiride, and meglitinides, such as nateglinide and repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, such as Exendin 4, and liraglutide, and GLP-1 receptor agonists such as those disclosed in WO0/42026 and WO00/59887;

(h) GIP and GIP mimetics such as those disclosed in WO00/58360, and GP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors;

(o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers; and (p) glucokinase activators (GKAs).

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001) and D. Spanswick and K. Lee, "Emerging antiobesity drugs," *Expert Opin. Emerging Drugs*, 8: 217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents*, 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science*, 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted heterocyclic intermediates such as those of formula III, using standard peptide coupling conditions followed by deprotection. The preparation of these intermediates is described in the following schemes.

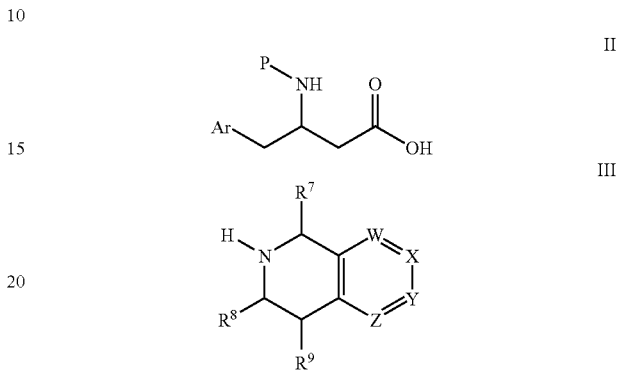

where Ar, W, X, Y, Z, $R^7$, $R^8$, and $R^9$ are as defined above and P is a suitable nitrogen protecting group such as tert-butoxycarbonyl, benzyloxycarbonyl, or 9-fluorenylmethoxy-carbonyl.

SCHEME 1

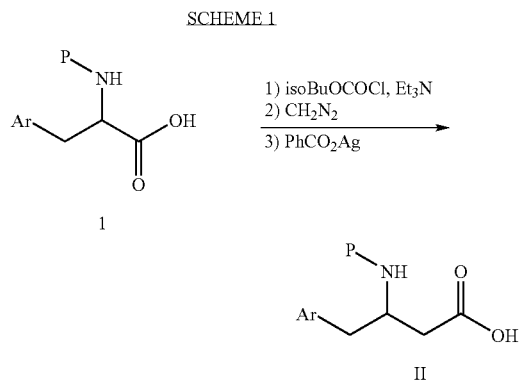

Compounds of formula II are commercially available, known in the literature or may be conveniently prepared by a variety of methods familiar to those skilled in the art. One common route is illustrated in Scheme 1. Acid 1, which may be commercially available or readily prepared from the corresponding amino acid by protection using, for example, di-tert-butyl-dicarbonate (for P=Boc), carbobenzyloxy chloride (for P=Cbz), or N-(9-fluorenylmethoxiycarbonyloxy) succinimide (for P=Fmoc), is treated with isobutyl chloroformate and a base such as triethylamine or N,N-diisopropylethylamine, followed by diazomethane. The resultant diazoketone is then treated with silver benzoate in a solvent such as methanol or aqueous dioxane and may be subjected to sonication following the procedure of Sewald et al., *Synthesis*, 837 (1997) in order to provide the beta amino acid II. As will be understood by those skilled in the art, for the preparation of enantiomerically pure beta amino acids II, enantiomerically pure alpha amino acids 1 may be used. Alternate routes to these compounds can be found in the following reviews: E. Juaristi, *Eizantioselective Synthesis of*

β-*Amino Acids*, Ed., Wiley-VCH, New York: 1997, Juaristi et al., *Aldrichimica Acta,* 27, 3 (1994), Cole et al., *Tetrahedron,* 32, 9517 (1994).

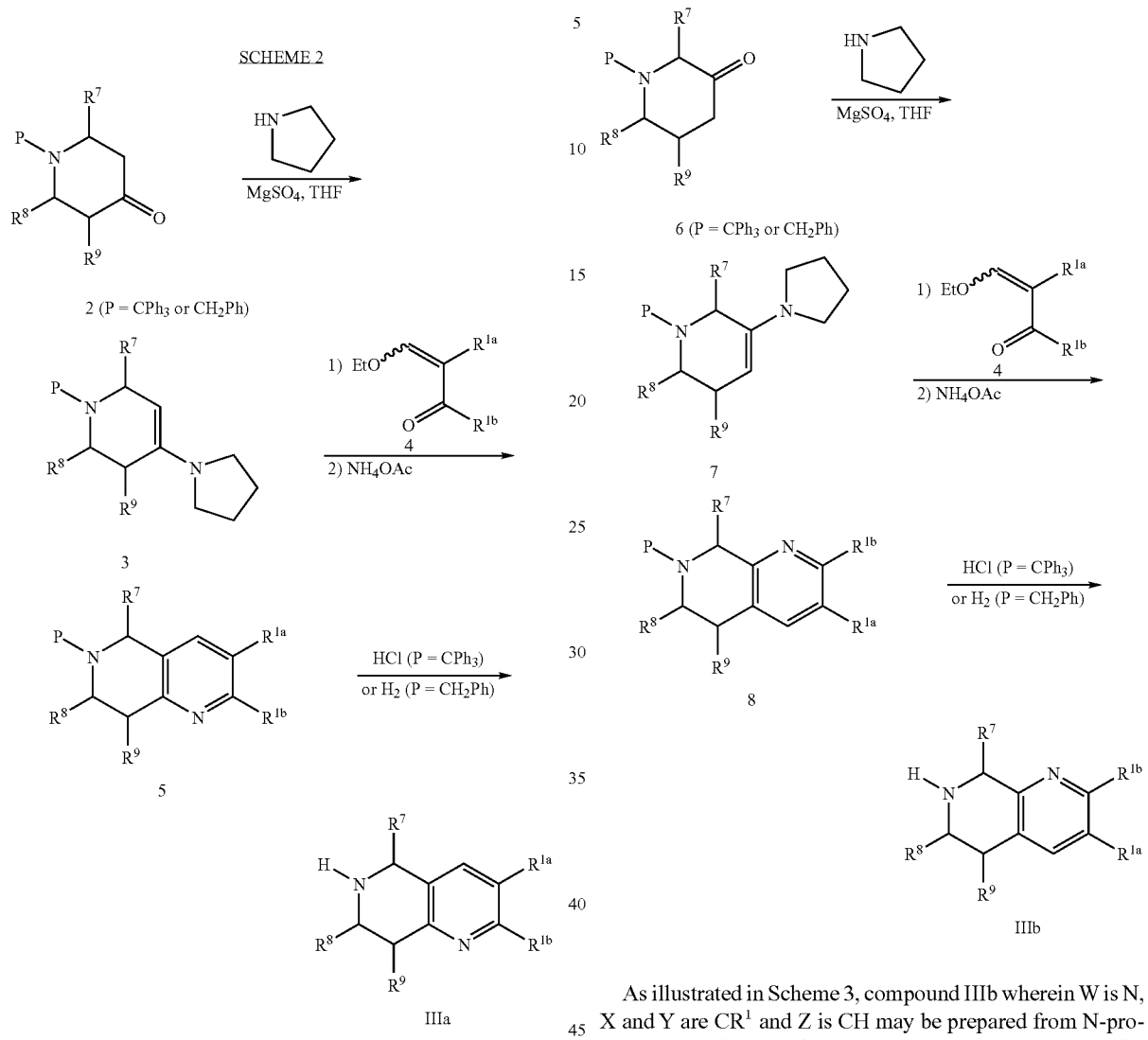

Compounds III are commercially available, known in the literature or may be conveniently prepared by a variety of methods familiar to those skilled in the art. One convenient method when W is CH, X and Y are $CR^1$ and Z is N is shown in Scheme 2. Piperidinone 2, in which the nitrogen is protected, for example, as a trityl or benzyl derivative, is treated with piperidine, conveniently in the presence of magnesium sulfate in a solvent such as tetrahydrofuran, to provide the corresponding enamine 3, in some cases as a mixture of isomers. Treatment of 3 with ethoxyvinylcarbonyl derivative 4 followed by ammonium acetate, typically at elevated temperature, gives the fused pyridine derivative 5. This reaction is particularly favored when $R^{1a}$ is H or $CO_2C_{1-6}$ alkyl and when $R^{1b}$ is $CF_3$ or $C_{1-6}$ alkyloxy. When $R^{1b}$ is $C_{1-6}$ alkyloxy, compound 5 is isolated as the hydroxypyridine derivative wherein $R^{1b}$ is OH. The protecting group may be removed by treatment with acid such as hydrogen choride when the protecting group is trityl or by catalytic hydrogenation when the protecting group is benzyl to give the desired product IIIa.

As illustrated in Scheme 3, compound IIIb wherein W is N, X and Y are $CR^1$ and Z is CH may be prepared from N-protected piperidinone 6, following the route described above for the synthesis of IIIa.

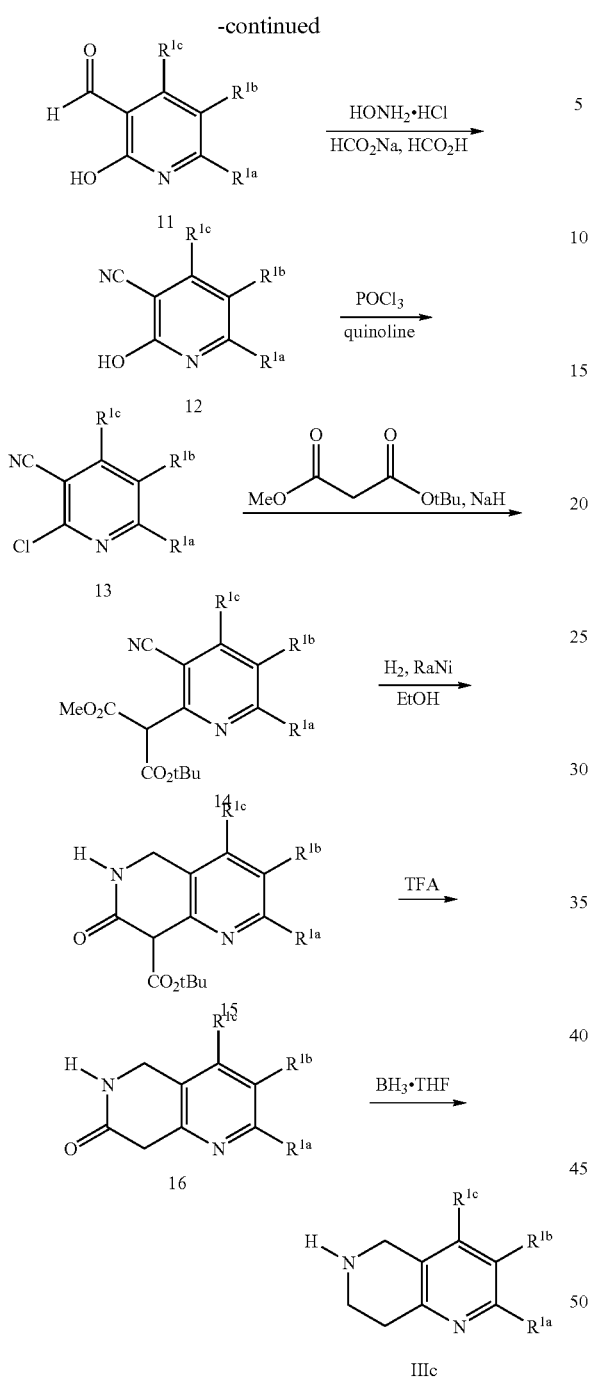
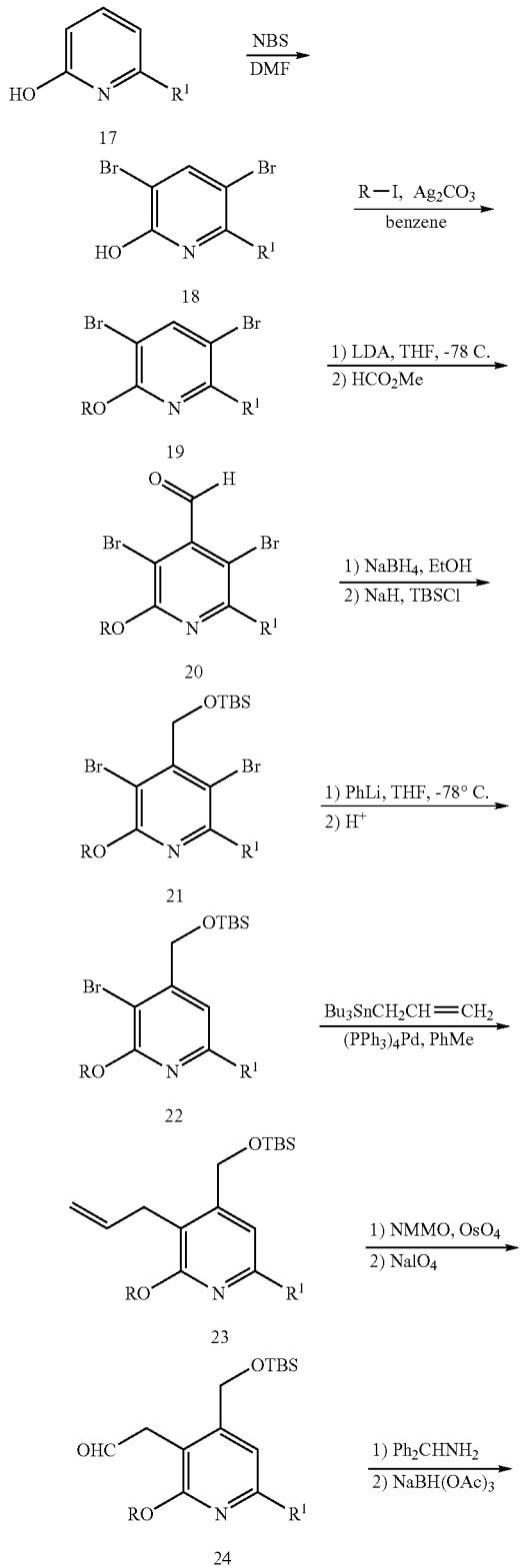

salt of methyl tert-butyl malonate gives pyridine 14. Raney nickel reduction followed by ring closure provides fused pyridine 15. Ester hydrolysis with TFA and decarboxylation gives amide 16. Borane reduction provides the desired compound IIIc.

Compound IIIc wherein W, X and Y are $CR^1$ and Z is N may be prepared as illustrated in Scheme 4. Hydroxypyridine 9 is brominated, for example by treatment with bromine and sodium acetate in acetic acid, to give bromopyridine 10. Deprotonation of the alcohol with sodium hydride followed by metal-halogen exchange, conveniently by treatment with tert-butyllithium gives a dianion which is quenched with N,N-dimethylformamide to provide aldehyde 11. Conversion of the aldehyde to the nitrile under standard conditions, for example by treatment with hydroxylamine hydrochloride and sodium formate in formic acid, gives nitrile 12. Treatment with phosphorus oxychloride provides chloropyridine 13. Displacement of the chloride by treatment with the sodium -continued

[Scheme continues with structures 25, 26, and IIId]

Compound IIId wherein W is CH, X is CR¹, Y is N and Z is C—OR (R=C$_{1-6}$ alkyl) may be prepared as illustrated in Scheme 5. Hydropyridine 17 is brominated, conveniently using N-bromosuccinimide in DMF, to provide dibromopyridine 18. The hydroxy group is alkylated, for example by treatment with an alkyl halide such as an alkyl iodide in the presence of silver carbonate, to provide alkoxypyridine 19. Formylation is achieved by deprotonation with a base such as lithium N,N-diisopropylamide followed by quenching with methyl formate to provide aldehyde 20. The aldehyde is treated with a reducing agent such as sodium borohydride, and then protected with a protecting group such as tert-butyldimethylsilyl (TBS) using TBS chloride. Treatment of the resultant pyridine 21 with phenyllithium followed by quenching with a proton source such as citric acid provides monobromide 22. Allylation of the bromide may be achieved by treatment with allyltributyltin in the presence of a catalyst such as tetrakis(triphenylphosphine) palladium. The allyl group is oxidized, for example using N-methylmorpholine N-oxide and osmium tetroxide in a polar solvent such as acetone/water followed by sodium periodate to provide aldehyde 24. Reductive amination using a protected ammonia equivalent such as (diphenylmethyl)amine and a reducing agent such as sodium triacetoxyborohydride provides amine 25. The diphenylmethyl group is removed by catalytic hydrogenation and the resultant primary amine protected, for example, as its BOC derivative, by treatment with di-tert-butyl dicarbonate. Deprotection of the silyl ether to the corresponding alcohol using a fluoride source such as tetrabutylammonium fluoride provides pyridine 26. The alcohol is treated with an oxidizing agent such as sulfur trioxide-pyridine to give the corresponding aldehyde. Deprotection of the amine using an acid such as hydrogen chloride and then internal reductive amination gives the desired cyclized intermediate IIId.

SCHEME 6

[Scheme 6 with structures 27, 28, 30, and IIIe]

Compounds IIIe wherein W is CH, X is N, Y is CR¹ and Z is N may be conveniently prepared as shown in Scheme 6. N-protected 4-piperidinone 27 is treated with 1,1-dimethoxy-N,N-dimethylmethanamine in DMF at elevated temperature to give enamine 28, which in some cases may be a mixture of isomers. Condensation of 28 with amidine 29 in the presence of a base such as sodium ethoxide in ethanol provides pyrimidine 30. Deprotection, in the case of BOC, with an acid such as hydrogen chloride or trifluoroacetic acid gives tetrahydropyridopyrimidine IIIe.

SCHEME 7

[Scheme 7 with structures 31, 32, and 29]

N-protected 4-piperidinone 27 and amidine 29 are commercially available, known in the literature or may be conveniently prepared by a variety of methods familiar to those skilled in the art. One convenient method for preparation of amidine 29 is shown in Scheme 7. Nitrile 31, which itself is commercially available, known in the literature, or conveniently prepared by a variety of methods familiar to those skilled in the art, is treated with hydrogen chloride, conveniently as a solution in dioxane, in ethanol to give imidate 32. Treatment with an ethanolic ammonia solution provides amidine 29.

SCHEME 8

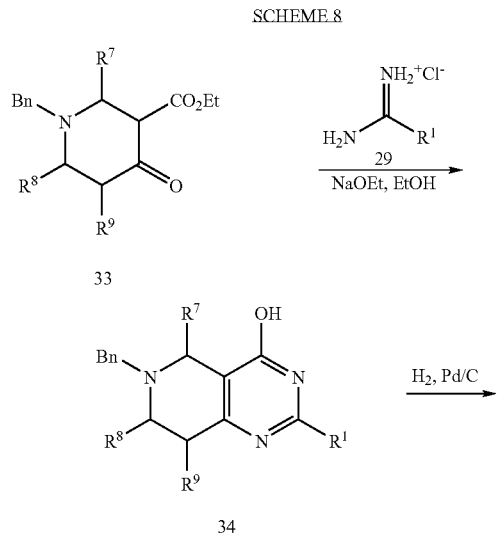

33

34

IIIf

The preparation of intermediate IIIf wherein W is C—OH, X is N, Y is CR$^1$ and Z is N is illustrated in Scheme 8. Ketoester 33 is treated with amidine 29 in the presence of a base such as sodium ethoxide in ethanol to provide tetrahydropyridopyridimine 34. Deprotection of the nitrogen using catalytic hydrogenation, for example by treatment with hydrogen in the presence of palladium on carbon, provides IIIf.

SCHEME 9

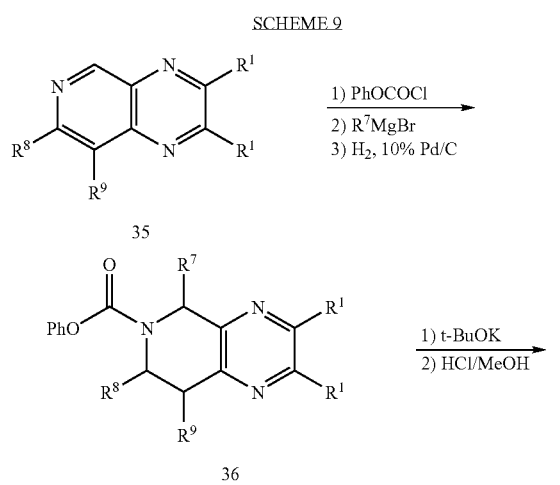

35

36

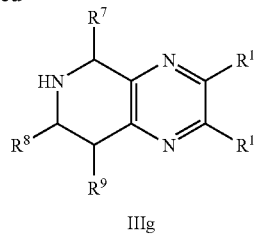

IIIg

One convenient method for the synthesis of intermediate IIIg wherein W is N, X is CR$^1$, Y is CR$^1$ and Z is N and wherein R$^7$ is an akyl or aryl group is illustrated in Scheme 9. Pyridopyrazine 35 is activated with phenyl chloroformate and treated with a Grignard reagent to provide, after reduction with hydrogen in the presence of a catalyst such as 10% palladium on carbon, tetrahydropyridopyrazine 36. Conversion of the phenylcarbamate to a BOC group is accomplished by treatment with potassium tert-butoxide. Removal of the BOC, for example, using methanolic hydrogen chloride, provides the desired intermediate IIIg.

SCHEME 10

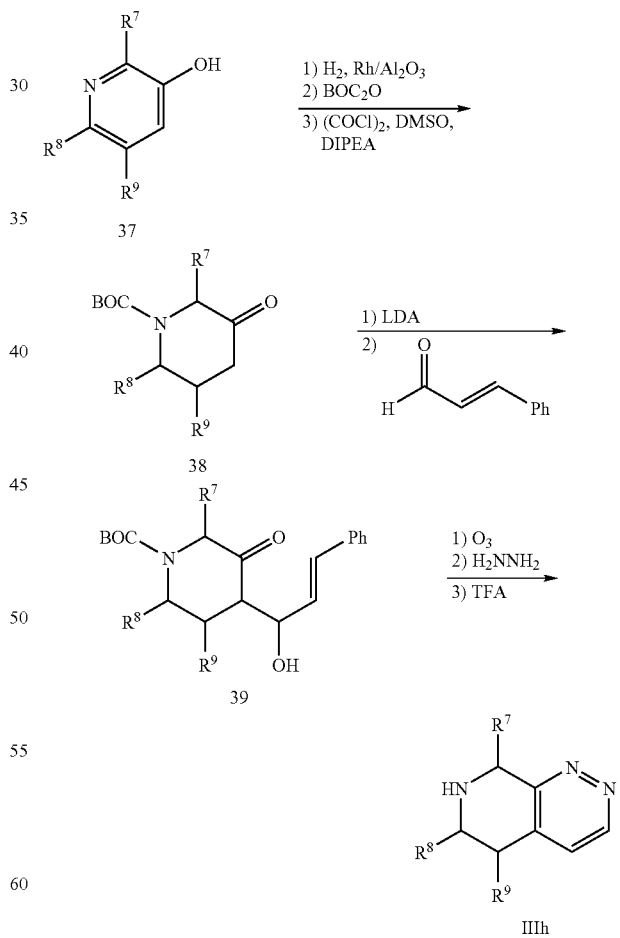

37

38

39

IIIh

Scheme 10 shows the preparation of intermediate IIIh, wherein W is N, X is N, Y is CH and Z is CH. Hydroxypyridine 37 is hydrogenated in the presence of a catalyst such as rhodium on alumina and the resultant piperidine derivative protected as its BOC derivative. The alcohol is oxidized to give ketone 38, conveniently using Swern conditions. Treatment with a strong base such as LDA followed by trapping of the resultant enolate with an oxaldehyde synthon such as cinnamaldehyde provides hydroxyketone 39. Ozonolysis followed by treatment with hydrazine gives the N-protected tetrahydropyridopyridazine derivative, which is treated with an acid such as trifluoroacetic acid to give intermediate IIIh.

diketone 42 with an appropriate amidrazone 43 gives a mixture of two tetrahydropyridotriazines. These may be separated, for example by using flash chromatography or HPLC, to provide, after deprotection under acidic conditions, intermediates IIIj and IIIk.

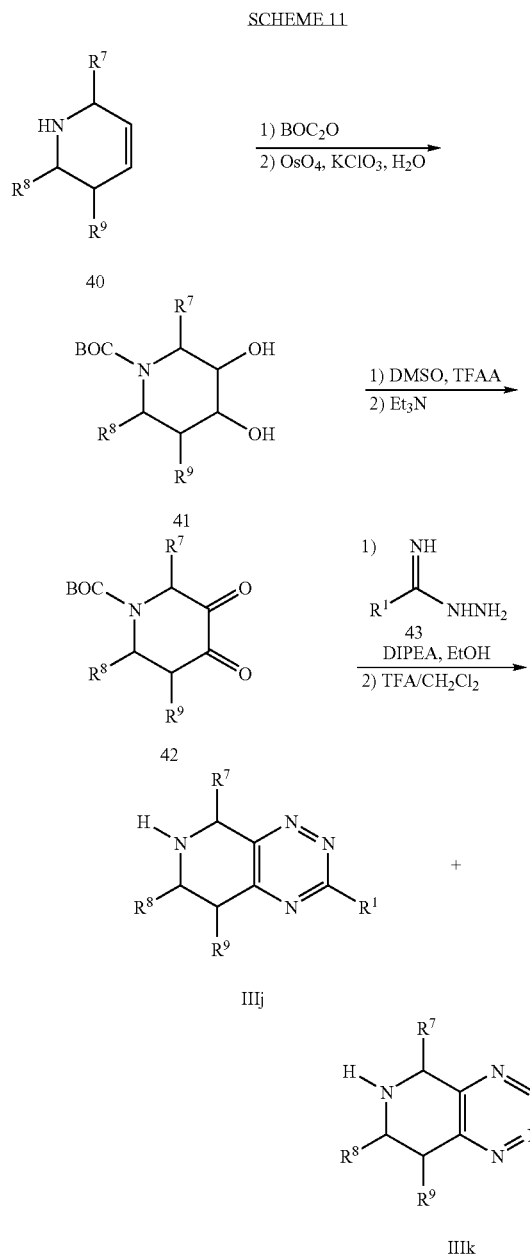

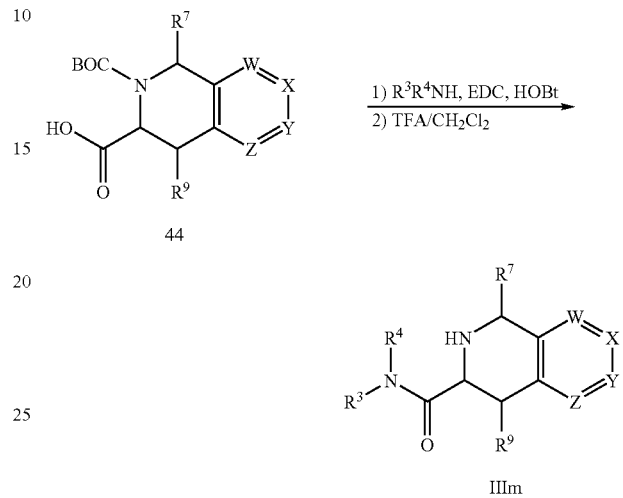

One convenient method for the synthesis of intermediate IIIm wherein $R^8$ is $CONR^3R^4$ is shown in Scheme 12. BOC protected aminoacid 44, which is commercially available, known in the literature, or readily prepared by a variety of methods known to those skilled in the art, is treated with an amine under standard peptide coupling conditions, for example using EDC and HOBt. Deprotection under acidic conditions provides the desired intermediates IIIm.

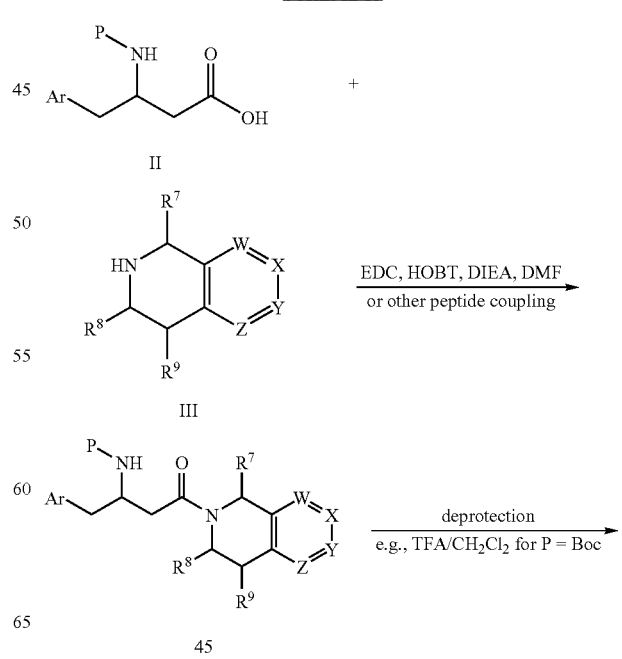

Intermediate IIIj, wherein W is N, X is N, Y is $CR^1$, and Z is N, and intermediate IIIk, wherein W is N, X is $CR^1$, Y is N, and Z is N, are available as outlined in Scheme 11. Tetrahydropyridine 40 is protected, for example as its BOC derivative by treatment with di-tert-butyl dicarbonate, and the olefin oxidized, conveniently by treatment with osmium tetroxide and potassium chlorate, to provide diol 41. The diol may be oxidized to diketone 42 using Swern conditions. Treatment of

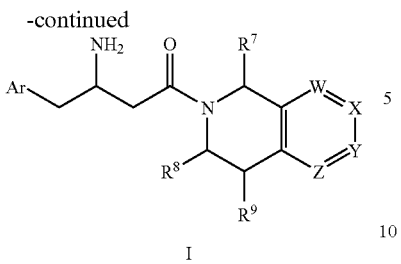

I

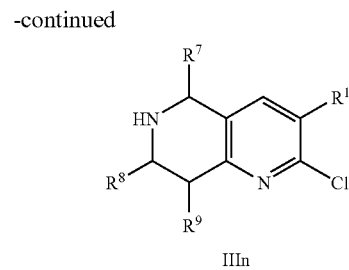

IIIn

Intermediates II and III are coupled under standard peptide coupling conditions, for example, using 1-ethyl-3-(3-dimethylaminopropyl)carbodiimide and 1-hydroxybenzotriazole (EDC/HOBT) or O-(7-azabenzotriazol-1-yl)-N,N,N',N'-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 45 as shown in Scheme 13. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or methanolic hydrogen chloride in the case of Boc to give the desired amine I. The product is purified from unwanted side products, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases the product I, prepared as described in Scheme 13, may be further modified, for example, by manipulation of substituents on Ar, $R^7$, $R^8$, $R^9$, W, X, Y or Z. These manipulations may include, but are not limited to, reduction, oxidation, alkylation, acylation, and hydrolysis reactions that are commonly known to those skilled in the art.

In some cases intermediates described in the above schemes may be further modified before the sequences are completed, for example, by manipulation of substituents on Ar, $R^7$, $R^8$, $R^9$, W, X, Y or Z. These manipulations may include, but are not limited to, reduction, oxidation, alkylation, acylation, and hydrolysis reactions that are commonly known to those skilled in the art.

One such example is illustrated in Scheme 14 for the preparation of intermediate IIIn wherein W is CH, X is $CR^1$, Y is Cl, and Z is N. Tetrahydropyridopyridimine 5a, prepared as described in Scheme 2, is treated with a chlorinating agent such as phenylphosphonic dichloride or phosphorus oxychloride, typically at elevated temperatures such as 100-200° C., to give chloropyridine 46. Deprotection of the nitrogen using 1-chloroethyl chloroformate provides IIIn.

SCHEME 15

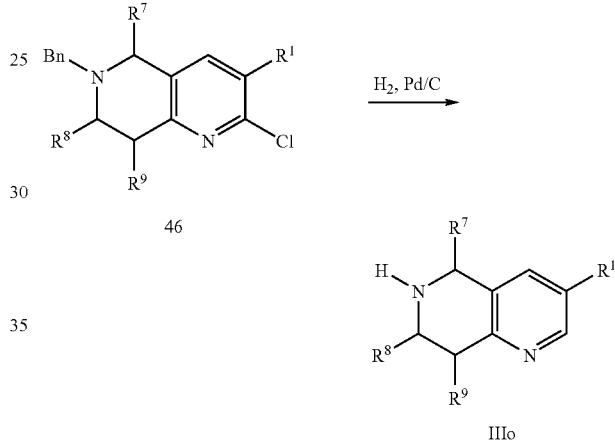

IIIo

Another such example is shown in Scheme 15. Deprotection of intermediate 46, prepared as described in Scheme 14, using catalytic hydrogenation, for example by treatment with hydrogen in the presence of palladium on carbon, provides IIIo, wherein W is CH, X is $CR^1$, Y is CH, and Z is N.

SCHEME 14

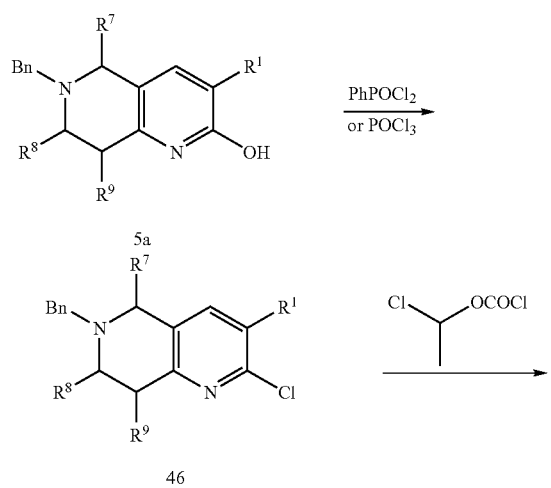

SCHEME 16

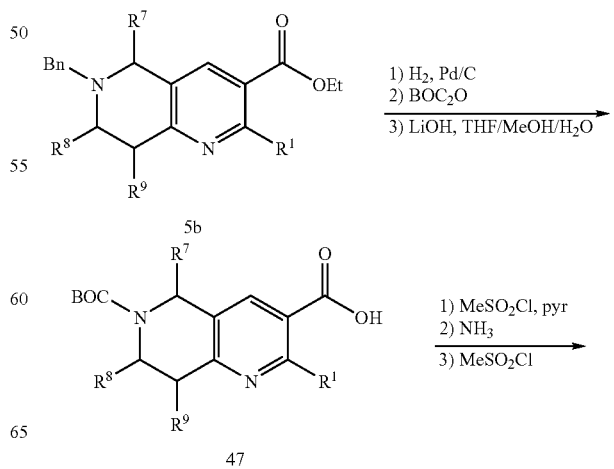

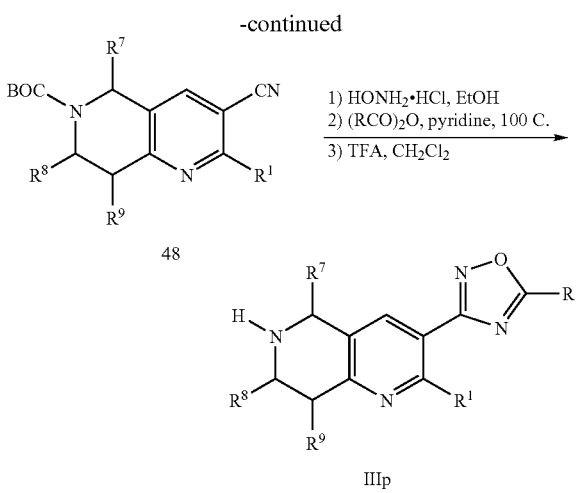

An additional example is provided in Scheme 16 for the preparation of intermediate IIIp, wherein W is CH, X is C-heterocycle, Y is CR¹, and Z is N. Ester 5b, prepared as described in Scheme 2, is subjected to catalytic hydrogenation conditions to remove the benzyl protecting group, and the nitrogen is reprotected, for example, as its BOC derivative using di-tert-butyl dicarbonate. Hydrolysis of the ester provides acid 47. The acid is converted to the corresponding nitrile 48 using standard conditions. Treatment with hydroxylamine hydrochloride followed by an anhydride provides, after deprotection under acidic conditions, intermediate IIIp. As will be understood by those skilled in the art, a variety of heterocycles are readily available from acid 47 and nitrile 48 using methods in the literature or known to those skilled in the art.

SCHEME 17

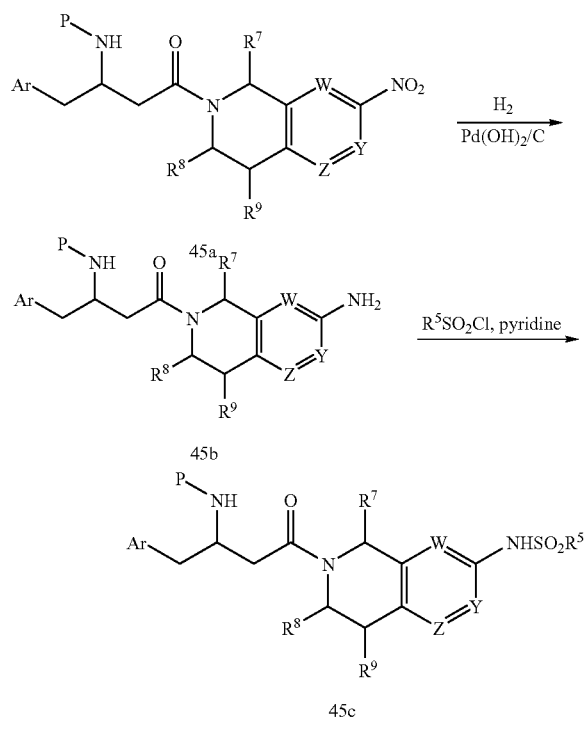

Scheme 17 illustrates the preparation of intermediate 45c, wherein X is C—NHSO₂R⁵. Intermediate 45a, prepared as described in Scheme 13, is hydrogenated in the presence of a catalyst such as Pearlman's catalyst to provide amine 45b. Sulfonylation of the amine may be achieved by treatment with a sulfonyl chloride in the presence of a base, conveniently pyridine, to give intermediate 45c. Intermediates 45b and 45c may be deprotected as described in Scheme 13 to give the final product I.

SCHEME 18

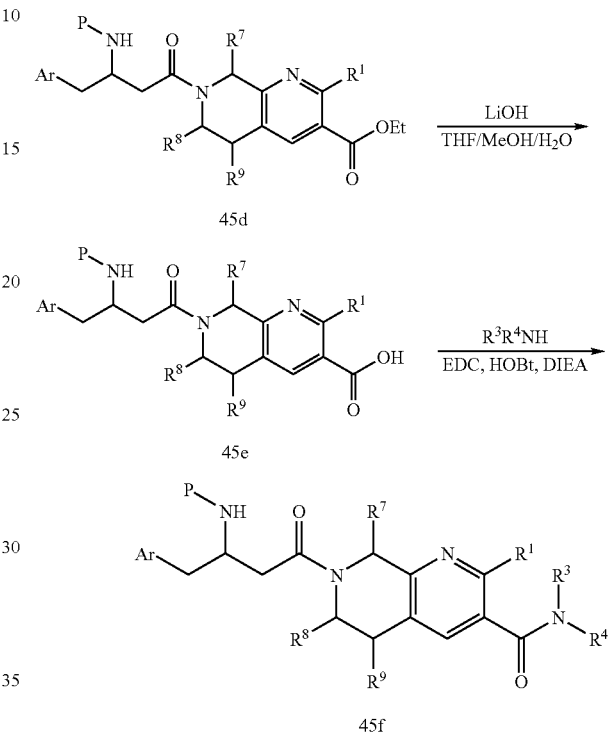

The modification of additional intermediates is illustrated in Scheme 18. Intermediate 45d, prepared as described in Scheme 13 using intermediate IIIb from Scheme 3, is treated with lithium hydroxide in an aqueous solvent mixture such as tetrahydrofuran/methanol/water to provide acid 45e. The acid is coupled with an amine using standard amine bond forming conditions such as EDC/HOBt to provide intermediate 45f. Intermediates 45d, 45e, and 45f may all be deprotected as described in Scheme 13 to provide final products I.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

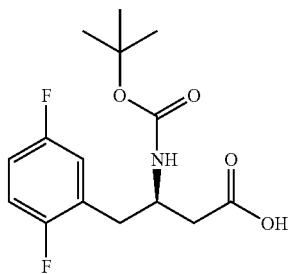

(3R)-3-[(tert-Butoxycarbonyl)amino]-4-(2,5-difluorophenyl)butanoic acid

Step A: (R,S)-N-(tert-Butoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and brine, dried over magnesium sulfate and concentrated in vacuo. The crude material was purified by flash chromatography (silica gel, 97:2:1 dichloromethane: methanol:acetic acid) to afford 671 mg of the title compound. LC/MS: 302 (M+1).

Step B: (R,S)-3-[(tert-Butoxycarbonyl)amino]-1-diazo-4-(2,5-difluoro-phenyl)butan-2-one To a solution of 2.23 g (7.4 mmol) of (R,S)-N-(tert-butoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded 1.5 g of diazoketone.
$^1$H NMR (500 MHz, CDCl$_3$) δ 7.03-6.95 (m, 1H, 6.95-6.88 (m, 2H), 5.43 (bs, 1H), 5.18 (bs, 1H), 4.45 (bs, 1H), 3.19-3.12 (m, 1H), 2.97-2.80 (m, 1H), 1.38 (s, 9H).

Step C: (3R)-3-[(tert-Butoxycarbonyl)amino]-4-(2,5-difluorophenyl)butanoic acid To a solution of 2.14 g (6.58 mmol) of (R,S)-3-[(tert-butoxycarbonyl)-amino]-1-diazo-4-(2,5-difluorophenyl)butan-2-one dissolved in 100 mL of methanol at −30° C. were added sequentially 3.3 mL (19 mmol) of diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol:1N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 360 mg of the title compound as a white foamy solid.
$^1$H NMR (500 MHz, CDCl$_3$) δ 7.21 (m, 1H), 6.98 (m, 2H), 6.10 (bs, 1H), 5.05 (m,1H), 4.21 (m, 1H), 2.98 (m, 2H), 2.60 (m, 2H), 1.38 (s, 9H).

INTERMEDIATE 2

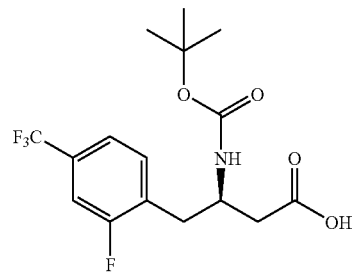

(3R)-3-[(tert-Butoxycarbonyl)amino]-4-[2-fluoro-4-(trifluoromethyl)phenyl]-butanoic acid

Step A: (2R,5S)-2,5-Dihydro-3,6-dimethoxy-2-(2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (19.5 mmol) of 2-fluoro-4-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0-5% ethyl acetate in hexanes) afforded 5.5 g of the title compound.
$^1$H NMR (500 MHz, CDCl$_3$) δ 7.33-7.25 (m, 3H), 4.35-4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25-2.15 (m, 1H), 1.0 (d, 3H, J=7 Hz), 0.66 (d, 3H, J=7 Hz).

Step B: (R)-N-(tert-Butoxycarbonyl)-2-fluoro-4-trifluoromethyl-phenylalanine methyl ester To a solution of 5.5 g (15 mmol) of (2R,5S)-2,5-dihydro-3,6-dimethoxy-2-(2'-fluoro-4'-(trifluoromethyl)benzyl)-5-isopropylpyrazine in 50 mL of a mixture of acetonitrile: dichloromethane (10:1) was added 80 mL of 1N aqueous trifluoroacetic acid. The reaction was stirred for 6 h and the organic solvents were removed in vacuo. Sodium carbonate was added until the solution was basic (>pH 8), and then the reaction was diluted with 100 mL of tetrahydrofuran and 10 g (46 mmol) of di-tert-butyl dicarbonate was added. The resultant slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded 5.1 g of the title compound.
$^1$H NMR (500 MHz, CDCl$_3$) δ 7.38-7.28 (m, 3H), 5.10 (bd, 1H), 4.65-3.98 (m, 1H), 3.76 (s, 3H), 3.32-3.25 (m, 1H), 3.13-3.05 (m, 1H), 1.40 (s, 9H).

Step C: (R)-N-(tert-Butoxycarbonyl)-2-fluoro-4-trifluoromethyl)phenyl-alanine A solution of 5.1 g (14 mmol) of (R,S)-N-(tert-butoxycarbonyl)-2-fluoro-4-trifluoromethyl)phenylalanine methyl ester in 350 mL of a mixture of tetrahydrofuran: methanol:1N lithium hydroxide (3:1:1) was stirred at 50° C. for 4 h. The reaction was cooled, acidified with 5% hydrochloric acid and extracted with ethyl acetate. The combined organic phases were washed with brine, dried over magnesium sulfate and concentrated in vacuo to give 4.8 g of the title compound.

$^1$H NMR (500 MHz, CD$_3$OD) δ 7.45-7.38 (m, 3H), 4.44-4.40 (m, 1H), 3.38-3.33 (m, 1H), 2.98 (dd, 1H, J=9.6, 13.5 Hz), 1.44 (s, 9H).

Step D: (3R)-3-[(tert-Butoxycarbonyl)amino]-4-[2-fluoro-4-(trifluoromethyl)-phenyl]-butanoic acid To a solution of 3.4 g (9.7 mmol) of the product from Step C in 60 mL of tetrahydrofuran at 0° C. were added sequentially 2.3 mL (13 mmol) of diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane:ethyl acetate) afforded 0.5 g of diazoketone. To a solution of 0.5 g (1.33 mmol) of the diazoketone dissolved in 100 mL of methanol at 0° C. were added sequentially 0.7 mL (4 mmol) of diisopropylethylamine and 32 mg (0.13 mmol) of silver benzoate. The reaction was stirred for 2 h before diluting with ethyl acetate and washing sequentially with 2N hydrochloric acid, saturated aqueous sodium bicarbonate, and brine. The organic phase was dried over magnesium sulfate, concentrated in vacuo and dissolved in 50 mL of a mixture of tetrahydrofuran:methanol:1N aqueous lithium hydroxide (3:1:1) and stirred at 50° C. for 3 h. The reaction was cooled, acidified with 5% hydrochloric acid and extracted with ethyl acetate. The combined organic phases were washed with brine, dried over magnesium sulfate and concentrated in vacuo to give 410 mg of the title compound as a white foamy solid.

$^1$H NMR (500 MHz, CD$_3$OD): δ 7.47-7.33 (m, 3-H), 4.88 (bs, 1H), 4.26-3.98 (m, 1H), 3.06-3.01 (m, 1H), 2.83-2.77 (m, 1H), 2.58-2.50 (m, 2H), 1.29 (s, 9H).

INTERMEDIATE 3

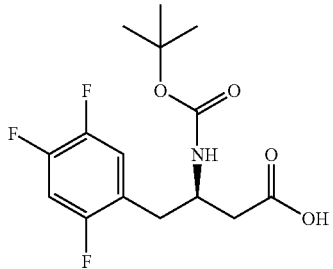

(3R)-3-[(tert-Butoxycarbonyl)amino]-4-(2,4,5-trifluorophenyl)butanoic acid

Step A: (2S,5R)-2,5-Dihydro-3,6-dimethoxy-2-isopropyl-5-(2',4',5'trifluorobenzyl)pyrazine The title compound (3.81 g) was prepared from 3.42 g (18.5 mmol) of (2S)-2,5-dihydro-3,6-dimethoxy-2-isopropylpyrazine and 5 g (22.3 mmol) of 2,4,5-trifluorobenzyl bromide using the procedure described for Intermediate 2, Step A.

$^1$H NMR (500 MHz, CDCl$_3$): δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H, 0.99 (d, 3H, J=8 Hz), 0.62 (d, 3H, J=8 Hz).

Step B: (R)-N-(tert-Butoxycarbonyl)-2,4,5-trifluorophenylalanine methyl ester

To a solution of 3.81 g (11.6 mmol) of (2S,5R)-2,5-dihydro-3,6-dimethoxy-2-isopropyl-5-(2',4',5'trifluorobenzyl) pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyl dicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford 2.41 g of the title compound.

$^1$H NMR (500 MHz, CDCl$_3$): δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C: (R)-N-(tert-Butoxycarbonyl)-2,4,5-trifluorophenylalanine

The title compound (2.01 g) was prepared from 2.41 g (7.5 mmol) of (R)-N-(tert-butoxycarbonyl)-2,4,5-trifluorophenylalanine methyl ester using the procedure described for Intermediate 2, Step C. LC/MS: 220.9 (M+1-BOC).

Step D: (3R)-3-[(tert-Butoxycarbonyl)amino]-4-(2,4,5-trifluorophenyl)-butanoic acid To a solution of 0.37 g (1.16 mmol) of (R)-N-(1,1-dimethylethoxy-carbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane:water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded 401 mg of the title compound.

$^1$H NMR (500 MHz, CDCl$_3$) δ 7.06 (m, 1H), 6.95 (m, 1H), 5.06 (bs, 1H), 4.18 (m, 1H), 2.98 (m, 2H), 2.61 (m, 2H), 1.39 (s, 9H).

INTERMEDIATE 4

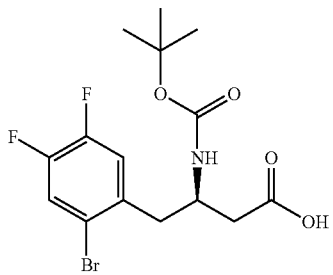

(3R)-4-(2-Bromo-4,5-difluorophenyl)-3-[(tert-butoxycarbonyl)amino]-butanoic acid To a solution of 2.4 g (10 mmol) of 2-bromo-4,5-difluorobenzoic acid [prepared according to the procedure of Braish et al., *Syn. Comm.*, 3067-3074 (1992)] in 75 mL of tetrahydrofuran was added 2.43 g (15 mmol) of carbonyldiimidazole. The solution was heated under reflux for 3.5 h, cooled to ambient temperature and 0.38 g (10 mmol) of sodium borohydride in 15 mL of water was added. The reaction was stirred for 10 min and partitioned between ethyl acetate and 10% aqueous sodium bicarbonate solution. The organic layer was washed twice with warm water, brine, dried over magnesium sulfate, and concentrated in vacuo. Purification by flash chromatography (silica gel, 4:1 hexane:ethyl acetate) afforded 1.9 g of 2-bromo-4,5-difluorobenzyl alcohol. To a solution of 1.9 g (8.4 mmol) of 2-bromo-4,5-difluorobenzyl alcohol in 30 mL of dichloromethane at 0° C. was added 3.4 g (10 mmol) of carbon tetrabromide and 2.7 g (10 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 20:1 hexane:ethyl acetate) to afford 2.9 g of 2-bromo-4,5-difluorobenzyl bromide contaminated with carbon tetrabromide which was used without further purification. Using the procedures outlined for the preparation of Intermediates 2-4, the benzyl bromide derivative was converted to the title compound.

LC/MS: 394 and 396 (M+1).

Essentially following the procedures outlined for the preparation of Intermediates 1-4, the Intermediates in Table 1 were prepared.

TABLE 1

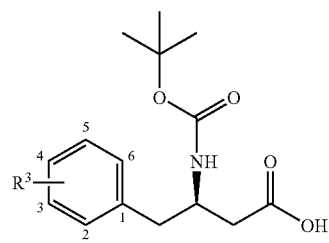

| Intermediate | R³ | Selected ¹H NMR data (CD₃OD) |
|---|---|---|
| 5 | 2-F,4-Cl,5-F | 7.11 (dd, 1 H, J = 8.9, 6.4 Hz), 7.03 (dd, 1 H, J = 9.0, 6.6) |
| 6 | 2-F,5-Cl | 7.27 (dd, 1 H, J = 6.4, 2.5 Hz), 7.21 (m, 1 H), 7.03 (t, 1 H, J = 9.2 Hz) |

TABLE 1-continued

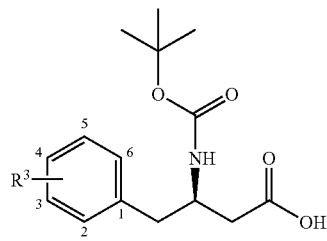

| Intermediate | R³ | Selected ¹H NMR data (CD₃OD) |
|---|---|---|
| 7 | 2-Me,5-Cl | 7.16 (d, 1 H, J = 1.8 Hz), 7.11-7.07 (m, 2 H), 2.34 (s, 3 H) |
| 8 | 2-Cl,5-Cl | 7.34 (d, 1 H, J = 9.0), 7.33 (d, 1 H, J = 2.1 Hz), 7.21 (dd, 1 H, J = 8.5, 2.5 Hz) |
| 9 | 2-F,3-Cl,6-F | 7.35 (td, 1 H, J = 8.5, 5.8 Hz), 6.95 (t, 1 H, J = 8.5 Hz) |
| 10 | 3-Cl,4-F | 7.33 (d, 1 H, J = 6.9 Hz), 7.19-7.11 (m, 2 H) |
| 11 | 2-F,3-F,6-F | 7.18-7.12 (m, 1 H), 6.91 (m, 1 H) |
| 12 | 2-F,4-F,6-F | 6.81 (t, 2 H, J = 8.4 Hz) |
| 13 | 2-OCH₂Ph,5-F | 7.49 (d, 2 H, J = 7.6 Hz), 7.38 (t, 2 H, J = 7.3 Hz), 7.30 (t, 1 H, J = 7.3 Hz), 6.96-6.89 (m, 3 H), 5.11 (d, 1 H, J = 11.7 Hz), 5.08 (d, 1 H, J = 11.9 Hz) |

INTERMEDIATE 14

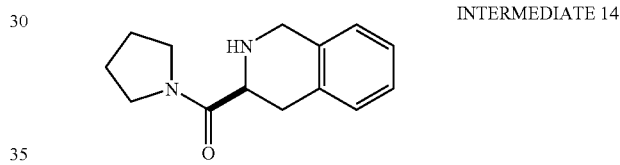

(3S)-3-(Pyrrolidin-1-ylcarbonyl)-1,2,3,4-tetrahydroisoquinoline

To a solution of N-(tert-butoxycarbonyl)-(3S)-1,2,3,4-tetrahydro-isoquinoline-3-carboxylic acid (Boc-TIC-OH; 5.55 g, 20 mmol) in 200 mL of dichloromethane was added (1-[3-(dimethylamino)propyl]-3-ethylcarbodiimide hydrochloride (EDC, 4.03 g, 21 mmol), 1-hydroxybenzotriazole (HOBt; 2.85 g, 21 mmol) and N,N-diisopropylethylamine (4.4 mL, 25 mmol). After 10 min, pyrrolidine (1.8 mL, 21 mmol) was added, and the resultant solution was stirred at room temperature for 18 h. Additional dichloromethane (200 mL) was added, and the solution was washed sequentially with ice-cold 5% hydrochloric acid, saturated aqueous sodium bicarbonate solution, and saturated brine. The organic phase was dried over sodium sulfate and concentrated under reduced pressure to afford a pale yellow solid. Purification by flash chromatography (silica gel; 45% ethyl acetate-hexanes as eluant) afforded the BOC-protected intermediate (6.05 g) as an off-white solid, which was dissolved in 100 mL of dichloromethane, cooled in an ice-water bath and treated dropwise with 40 mL of trifluoroacetic acid. The solution was warmed to room temperature and, after 1.5 h, concentrated under reduced pressure. The resultant crude oil was partitioned between dichloromethane and 1N aqueous sodium hydroxide solution, and the aqueous layer was further extracted with dichloromethane. The combined organic extracts were washed with saturated brine, dried over sodium sulfate and concentrated under reduced pressure to afford a light yellow

INTERMEDIATE 15

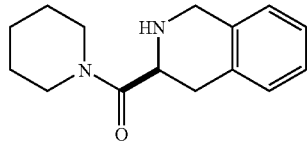

(3S)-3-(Piperidin-1-ylcarbonyl)-1,2,3,4-tetrahydroisoquinoline

Following a procedure similar to that described for Intermediate 14, treatment of Boc-TIC-OH with EDC, HOBt, N,N-diisopropylethylamine and piperidine, followed by deprotection using trifluoroacetic acid, afforded the title compound as a white foam. LC/MS: 245.2 (M+1).

INTERMEDIATE 16

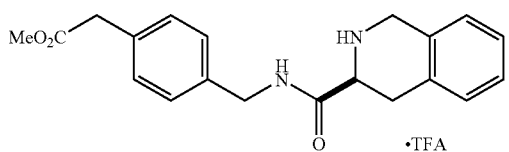

Methyl [4-[[[(3S)-1,2,3,4-tetrahydroisoquinolin-3-ylcarbonyl]amino]methyl]phenyl]acetate, trifluoroacetic acid To a solution of N-(tert-butoxycarbonyl)-(3S)-1,2,3,4-tetrahydroisoquinoline-3-carboxylic acid (Boc-TIC-OH; 111 mg, 0.4 mmol) in 2.0 mL of dichloromethane were added 1-[3-(dimethylamino)propyl]-3-ethylcarbodiimide hydrochloride (EDC; 84 mg, 0.44 mmol) and N,N-diisopropylethylamlne (0.154 mL, 0.88 mmol). After 10 min, methyl 4-(aminomethyl)phenylacetate hydrochloride (95 mg, 0.44 mmol) was added, and the resultant solution was stirred at room temperature for 24 h. Additional dichloromethane (6 mL) was added, and the solution was washed sequentially with ice-cold 5% hydrochloric acid, saturated aqueous sodium bicarbonate solution, and saturated brine. The organic phase was dried over sodium sulfate and concentrated under reduced pressure to a pale yellow oil. Purification by flash chromatography (silica gel; 35-50% ethyl acetate/hexanes step gradient) afforded the BOC-protected intermediate (68 mg) as a clear oil, which was dissolved in 4 mL of dichloromethane and treated with 2 mL of trifluoroacetic acid. The solution was stirred at room temperature for 1 h and was then concentrated under reduced pressure to afford the title compound as a white powder. LC/MS: 339.2 (M+1).

INTERMEDIATE 17

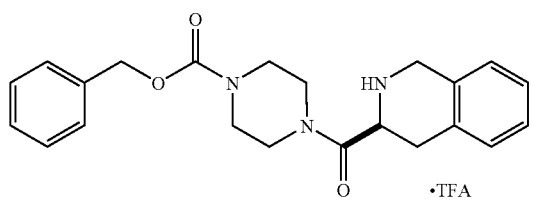

Benzyl 4-[(3S)-1,2,3,4-tetrahydroisoguinolin-3-ylcarbonyl]piperazine-1-carboxylate, trifluoroacetic acid salt Following a procedure similar to that described for Intermediate 14, treatment of Boc-TIC-OH with EDC, HOBt, N,N-diisopropylethylamine and benzyl 1-piperazinecarboxylate, followed by deprotection using trifluoroacetic acid, afforded the title compound as a white solid. LC/MS: 380.1 (M+1).

INTERMEDIATE 18

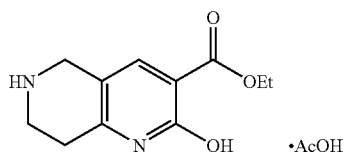

Ethyl 2-hydroxy-5,6,7,8-tetrahydro-1,6-naphthyridine-3-carboxylate, acetic acid salt Step A: Ethyl 6-benzyl-2-hydroxy-5,6,7,8-tetrahydro-1,6-naphthyridine-3-carboxylate A solution of 1-benzyl-4-piperidone (20 g, 106 mmol) and pyrrolidine (11.3 g, 159 mmol) in 300 mL of toluene was warmed at reflux for 18 h with azeotropic distillation of the water formed. The yellow solution was then concentrated under reduced pressure, and the resultant orange oil was dissolved in 200 mL of anhydrous 1,4-dioxane. To this solution was added 24 mL of diethyl ethoxymethylenemalonate under ice cooling. The mixture was then warmed at reflux temperature for 6 h, and was allowed to cool to room temperature overnight. Ammonium acetate (14.5 g) was added, and the reaction mixture was heated at reflux temperature for 1 h. The mixture was cooled to room temperature and was concentrated under reduced pressure to afford a red oil, which was triturated with ether. The resultant precipitate was collected and dried in vacuo to afford the title compound as a yellow powder.

Step B: Ethyl 2-hydroxy-5,6,7,8-tetrahydro-1,6-naphthyridine-3-carboxylate, acetic acid salt A mixture of the product (0.060 g, 0.19 mmol) from Step A above and 10% palladium on carbon (0.010 g) in 20 mL of glacial acetic was placed under a balloon of hydrogen and stirred overnight. The reaction mixture was filtered through a pad of Celite, and the filtrate was concentrated under reduced pressure to afford the title compound. LC/MS: 223 (M+1)

INTERMEDIATE 19

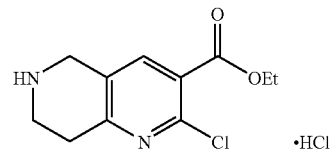

Ethyl 2-chloro-5,6,7,8-tetrahydro-1,6-naphthyridine-3-carboxylate, hydrochloride

Step A: Ethyl 6-benzyl-2-chloro-5,6,7,8-tetrahydro-1,6-naphthyridine-3-carboxylate, hydrochloride A mixture of the product from Intermediate 18, Step A (1.0 g, 3.2 mmol) and phenylphosphonic dichloride (1 mL) was warmed to 150° C. After 1 h, the mixture was cooled and to the dark brown mixture was added diisopropyl ether. The precipitated crystals were collected by filtration and suspended in chloroform. The mixture was neutralized by dropwise addition of saturated aqueous sodium bicarbonate solution. The organic layer was separated, dried over sodium sulfate and concentrated under reduced pressure. The residue was purified by flash chromatography (silica gel; 15% ethyl acetate/hexanes as eluant) to afford the title compound.

Step B: Ethyl 2-chloro-5,6,7,8-tetrahydro-1,6-naphthyridine-3-carboxylate, hydrochloride salt A solution of the product from Step A above (0.095 mg, 0.287 mmol) in 10 mL of dichloromethane was treated with 1-chloroethyl chloroformate (0.050 g; 0.344 mmol), and the mixture was warmed at reflux temperature overnight. The reaction was concentrated under reduced pressure to afford a yellow oil, which was dissolved in 10 mL of methanol. The solution was heated at 40° C. for 2 h, cooled to room temperature and concentrated in vacuo. To the yellow solid was added diisopropyl ether. The pale yellow crystals were collected by filtration and recrystallized from ethanol to afford the title compound. LC/MS: 240.0 (M+1)

INTERMEDIATE 20

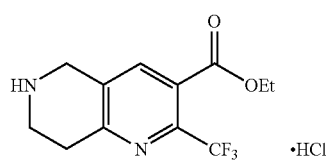

Ethyl 2-(trifluoromethyl)-5,6,7,8-tetrahydro-1,6-naphthyridine-3-carboxylate, hydrochloride salt

Step A: 1-Benzyl-4-pyrrolidino-1,2,5,6-tetrahydropyridine

A solution of N-benzyl piperidone (20.0 g, 53 mmol) and pyrrolidine (14.0 mL, 80 mmol) in 300 mL of toluene was warmed at reflux overnight with azeotropic removal of water. The reaction mixture was then cooled and concentrated under reduced pressure. The resultant dark oil was dissolved in 200 mL of ether, dried over magnesium sulfate, filtered and concentrated under reduced pressure.

Step B: Ethyl 6-benzyl-2-(trifluoromethyl)-5,6,7,8-tetrahydro-1,6-naphthridine-3-carboxylate A solution of the crude enamine (2.67 g, 10.6 mmol) from Step A above in 30 mL of dry 1,4-dioxane was cooled to approximately 10° C. and ethyl 2-(ethoxymethylene)-4,4,4-trifluoro-3-oxobutyrate (2.3 mL, 11.7 mmol) was added dropwise. The resultant orange solution was allowed to warm to room temperature overnight. Ammonium acetate (1.78 g) was added to the blood-red solution, and the mixture was heated at reflux for 2 h, cooled to room temperature and concentrated under reduced pressure. The residue was partitioned between ether and water, and the ether layer was washed with saturated brine, dried over magnesium sulfate and concentrated to a red oil. Purification by flash chromatography (silica gel; 12% ethyl acetate/hexanes as eluant) followed by preparative TLC (silica gel; 15% ethyl acetate/hexanes as eluant) afforded the title compound as a light yellow oil. LC/MS 365.2 (M+1).

Step C: Ethyl 2-(trifluoromethyl)-5,6,7,8-tetrahydro-1,6-naphthyridine-3-carboxylate, hydrochloride salt A solution of the product (140 mg, 0.385 mmol) from Step B in 1.5 mL of dry dichloromethane was treated with 1-chloroethyl chloroformate (0.050 mL, 0.46 mmol). The reaction mixture was warmed to 45° C. After 20 h, the solution was cooled to room temperature and concentrated under a stream of nitrogen. The resultant residue was dissolved in 3 mL of methanol and the solution was warmed at 40° C. for 2.5 h. The resultant solution was cooled and concentrated under a stream of nitrogen, and the residue was triturated with 4 mL of ethyl acetate. The solid precipitate was collected and dried in vacuo to afford the title compound as a white crystalline solid. LC/MS 275.0 (M+1).

INTERMEDIATE 21

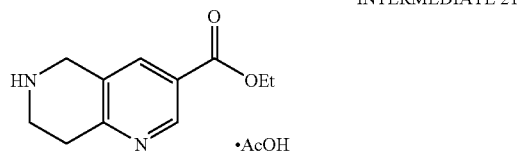

Ethyl 5,6,7,8-Tetrahydro-1,6-naphthyridine-3-carboxylate, acetic acid salt

A mixture of Intermediate 19 (3.70 g, 11.0 mmol) and 10% palladium on carbon (0.37 g) in glacial acetic acid (10 mL) was placed under a balloon of hydrogen and stirred at room temperature overnight. The reaction mixture was filtered through a pad of Celite, and the filtrate was concentrated under reduced pressure. Trituration with ether afforded the title compound as a white powder. LC/MS: 207 (M+1).

INTERMEDIATE 22

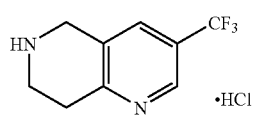

3-(Trifluoromethyl)-5,6,7,8-tetrahydro-1,6-naphthyridine, hydrochloride

Step A: 3-Bromo-2-hydroxy-5-trifluoromethylpyridine

To a solution of 5-trifluoromethyl-2-pyridinol (51 g, 310 mmol) and sodium acetate (26.2 g, 319 mmol) in glacial acetic acid (200 mL) was added bromine (16.7 mL, 325 mmol) and the resultant mixture was heated at 80° C. for 2.5 h. The reaction was allowed to cool to room temperature and then was evaporated under reduced pressure. The residue was neutralized with saturated aqueous sodium bicarbonate solution and extracted with 3 portions of ethyl acetate. The organic extracts were combined, dried over magnesium sulfate and concentrated under reduced pressure to afford the title compound. $^1$H NMR (400 MHz, CDCl$_3$) δ 8.04 (d, J=2.6 Hz, 1H), 7.89 (m, 1H).

Step B:
3-Formyl-2-hydroxy-5-trifluoromethylpyridine

Under nitrogen, the compound from Step A above (48.8 g, 202 mmol) was added in small portions to a suspension of sodium hydride (8.9 g, 220 mmol) in anhydrous tetrahydrofuran (500 mL). After complete addition of the intermediate, the reaction mixture was cooled to −78° C. and treated with tert-butyllithium (260 mL, 444 mmol) added dropwise via syringe. After stirring for 5 min, N,N-dimethylformamide (50 mL, 707 mmol) was added slowly, maintaining the temperature below −50° C. The resultant mixture was allowed to slowly warm to room temperature over 10 h. The mixture was quenched with 2N hydrochloric acid and then diluted with ethyl acetate (1000 mL). The organic layer was separated, washed with saturated brine, dried over magnesium sulfate and evaporated in vacuo. The desired product was precipitated out of a mixture of ethyl acetate and hexanes and filtered to yield a light brown solid.
$^1$H NMR (500 MHz, CD$_3$OD) δ 10.13 (s, 1H), 8.21 (s, 2H).

Step C:
3-Cyano-2-hydroxy-5-trifluoromethylpyridine

A mixture of the compound from Step B above (18 g, 95 mmol), sodium formate (7.1 g, 110 mmol), hydroxylamine hydrochloride (7.3 g, 110 mmol), and formic acid (150 mL) was stirred at room temperature for 2 h and then heated to reflux overnight. The reaction mixture was cooled, allowed to stand at room temperature for 7 d, poured into water and extracted with three portions of ethyl acetate. The combined organic layers were washed sequentially with two portions of water, saturated aqueous sodium bicarbonate solution and brine, dried over sodium sulfate and concentrated in vacuo to yield the desired product as a brown powder. $^1$H NMR (400 MHz, CD$_3$OD) δ 8.37 (d, J=2.7 Hz, 1H), 8.19 (q, J=0.7 Hz, 0.3 Hz, 1H).

Step D: 2-Chloro-3-cyano-5-trifluoromethylpyridine

To a mixture of phosphorous oxychloride (13.4 mL, 144 mmol) and quinoline (8.7 mL, 73 mmol) was added the product from Step C above (24.6 g, 131 mmol) and the resultant mixture was heated to reflux for 3 h. The reaction was cooled to 100° C. before water (70 mL) was slowly added. The mixture was further cooled to room temperature and neutralized by the cautious addition of saturated aqueous sodium bicarbonate solution. The aqueous layer was extracted with three portions of ethyl acetate and the organic layers were combined, dried over magnesium sulfate and concentrated in vacuo. The crude product was purified by flash chromatography to afford the desired compound. $^1$H NMR (500 MHz, CDCl$_3$) δ 8.88 (d, J=2.0 Hz, 1H), 8.26 (d, J=2.5 Hz, 1H).

Step E: tert-Butyl methyl 2-[3-cyano-5-(trifluoromethyl)pyridin-2-yl]malonate

To a suspension of sodium hydride (7.8 g, 200 mmol) in tetrahydrofuran (100 mL) under nitrogen was added dropwise a solution of tert-butyl methyl malonate (20 mL, 120 mmol) in anhydrous tetrahydrofuran (100 mL) via syringe. The reaction mixture was stirred for 0.5 h before a solution of the intermediate prepared in Step D above (20.1 g, 97.6 mmol) in tetrahydrofuran (200 mL) was added slowly via syringe. The reaction was stirred at room temperature overnight, then quenched with a saturated solution of ammonium chloride. The organic layer was separated and the aqueous layer was extracted with three portions of ethyl acetate. The combined organic layers were washed with water, dried over sodium sulfate and concentrated in vacuo. Flash chromatography afforded the title compound. $^1$H NMR (500 MHz, CDCl$_3$) δ 9.03 (d, J=1.5 Hz, 1H), 8.25 (d, J=2.0 Hz, 1H), 5.25 (s, 1H), 3.86 (s, 3M), 1.52 (s, 9H).

Step F: tert-Butyl 7-oxo-3-(trifluoromethyl)-5,6,7,8-tetrahydro-1,6-naphthyridine-8-carboxylate A suspension of Raney nickel (1 g) and the product from Step E above (18.2 g, 52.9 mmol) in ethanol (130 mL) was placed on a Parr shaker apparatus and hydrogenated at 40 psi hydrogen overnight. The suspension was filtered through Celite and the filtrate was evaporated in vacuo to afford the title compound. $^1$H NMR (500 MHz, CDCl$_3$) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

Step G: 3-(Trifluoromethyl)-5,8-dihydro-1,6-naphthyridin-7(6H)-one

To a mixture of the product from Step F above (16 g, 51 mmol) in dichloromethane (60 mL) was added trifluoroacetic acid (30 mL) and the resultant solution was stirred at room temperature for 0.5 h. The solution was evaporated under reduced pressure and the residue was dissolved in dichloromethane. The mixture was neutralized by the slow addition of a solution of saturated sodium bicarbonate and the organic layer was removed. The aqueous layer was extracted with four portions of dichloromethane and the combined organic layers were dried over sodium sulfate and concentrated under reduced pressure to afford the title compound. $^1$H NMR (400 MHz, CDCl$_3$) δ 8.81 (s, 1H), 7.78 (s, 1H), 7.30 (s, 1H), 4.63 (s, 2H), 3.90 (s, 2H).

Step H: 6-(tert-Butoxycarbonyl)-3-(trifluoromethyl)-5,6,7,8-tetrahydro-1,6-naphthyridine To a solution of the product from Step G above (18.0 g, 83.3 mmol) in tetrahydrofuran (50 mL) was added 1.0M borane in tetrahydrofuran (417 mL, 420 mmol) and the resultant solution was stirred at room temperature overnight. The solution was evaporated under reduced pressure and the residue was treated with 1% methanolic hydrogen chloride solution. The resultant mixture was heated at 50° C. overnight to break down the borane complex. Treatment with methanolic hydrogen chloride was repeated twice to insure that the borane complex was removed. A solution of the crude product and N,N-diisopropylethylamine (43 mL, 250 mmol) in dichloromethane was treated with di-tert-butyl dicarbonate (36.4 g, 167 mmol) and the resultant mixture was stirred at room temperature overnight. The solution was washed sequentially with saturated sodium bicarbonate solution, water, and saturated brine. The aqueous layers were combined and extracted with two portions of dichloromethane. The combined organic layers were then dried over sodium sulfate and concentrated under reduced pressure. The crude product was purified by flash chromatography and medium-pressure liquid chromatography (MPLC) to afford the title compound as a yellow solid. $^1$H NMR (500MHz, CDCl$_3$) δ 8.69 (s, 1H), 7.66 (s, 1H), 4.67 (s, 2H), 3.79 (t, J=6.0 Hz, 2H), 3.08 (t, J=6.0 Hz, 2H), 1.51 (s, 9H).

Step I: 3-(Trifluoromethyl)-5,6,7,8-tetrahydro-1,6-naphthyridine hydrochloride The product described in Step H above (11.89 g) was treated with a solution of 4N hydrogen chloride in 1,4-dioxane. The solution was stirred at room temperature for 2 h and then concentrated in vacuo to afford the title compound as a yellow powder. LC/MS 203.0 (M+H).

INTERMEDIATE 23

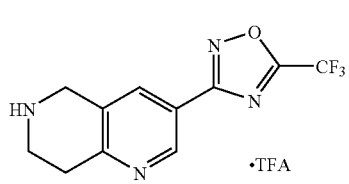

3-[5-(Trifluoromethyl)-1,2,4-oxadiazol-3-yl]-5,6,7,8-tetrahydro-1,6-naphthyridine, trifluoroacetic acid salt

Step A: Ethyl 6-(tert-butoxycarbonyl)-2-chloro-5,6,7,8-tetrahydro-1,6-naphthyridine-3-carboxylate To an ice-cold solution of Intermediate 21 (1.07 g, 4.0 mmol) in 10 mL of dichloromethane was added di-tert-butyl dicarbonate (0.88 g, 4.0 mmol) and N,N-diisopropylethylamine (0.7 mL, 4.0 mmol), and the reaction mixture was allowed to warm to room temperature overnight. The mixture was diluted with ethyl acetate and was washed sequentially with ice-cold 1M hydrochloric acid, saturated aqueous sodium bicarbonate solution and saturated brine, dried over magnesium sulfate and concentrated under reduced pressure. The residue was purified by flash chromatography (silica gel; 10-30% ethyl acetate/hexanes gradient elution) to afford the title compound as a white solid.

Step B: 6-(tert-Butoxycarbonyl)-3-cyano-5,6,7,8-tetrahydro-1,6-naphthyridine To a solution of the product from Step A above in 6 mL of 3:2:1 tetrahydrofuran/methanol/water was added lithium hydroxide monohydrate (0.23 g, 5.58 mmol). The mixture was allowed to stir overnight and the volatiles were removed under reduced pressure. Additional water was added, and the solution was acidified with citric acid monohydrate. The resultant precipitate was collected, washed with water, and dried in vacuo. To an ice-cold solution of this intermediate (1.0 g, 3.6 mmol) in 32 mL of pyridine was added methanesulfonyl chloride (0.41 g, 3.6 mmol) dropwise, and the resultant mixture was allowed to stir for one hour. Dry ammonia gas was bubbled into the reaction mixture for 2 minutes. The excess ammonia was then removed under reduced pressure, and the solution was cooled again in ice and treated with methanesulfonyl chloride (3.43 g, 30.0 mmol). The resultant mixture was allowed to warm to room temperature overnight. The reaction was concentrated under reduced pressure, and the residue was partitioned between ethyl acetate and 1N hydrochloric acid. The product was extracted with ethyl acetate, and the combined extracts were dried over magnesium sulfate and concentrated under reduced pressure. The resultant crystalline solid was triturated with ether, and the precipitate was collected to afford the title compound as a light orange powder.

Step C: 3-[5-(Trifluoromethyl)-1,2,4-oxadiazol-3-yl]-5,6,7,8-tetrahydro-1,6-naphthyridine, trifluoroacetic acid salt To a solution of the compound from Step B above in 7 mL of absolute ethanol (0.2 g, 0.77 mmol) was added hydroxylamine hydrochloride (0.067 g, 0.97 mmol), and sodium carbonate (0.1 g, 0.97 mmol). The reaction was warmed to reflux and, after 18 h, cooled to room temperature and concentrated under reduced pressure. To this crude intermediate were added pyridine (2.0 mL) and trifluoroacetic anhydride (0.158 g; 0.75 mmol) sequentially, and the mixture was warmed at 100° C. overnight. The reaction mixture was cooled, diluted with water and extracted with ethyl acetate. The combined extracts were dried over magnesium sulfate and concentrated in vacuo. The brown oil was purified by preparative thin-layer chromatography (1 mm silica gel; three elutions with 30% ethyl acetate/hexanes). The purified compound was then dissolved in dichloromethane (5 mL). Trifluoroacetic acid (2 mL) was added, and the solution was kept at room temperature for 1 h and then concentrated under reduced pressure to afford the title compound as a red gum. LC/MS: 271 (M+1).

INTERMEDIATE 24

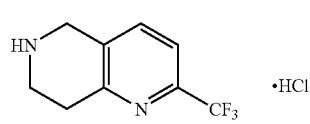

2-(Trifluoromethyl)-5,6,7,8-tetrahydro-1,6-naphthridine, hydrochloride

Step A: 6-Benzyl-2-(trifluoromethyl)-5,6,7,8-tetrahydro-1,6-naphthyridine

A solution of the crude enamine from Intermediate 20, Step A (904 mg, 3.6 mmol) in 15 mL of dry dioxane was cooled to approximately 10° C. and 4-ethoxy-1,1,1-trifluoro-3-buten-2-one (0.61 mL, 4.3 mmol) was added dropwise. The light red solution was allowed to warm to room temperature overnight, ammonium acetate (600 mg) was added, and the mixture was warmed to reflux. After 2.5 h, the dark red reaction mixture was cooled and concentrated under reduced pressure. The residue was dissolved in ether, washed sequentially with water and saturated brine, dried over magnesium sulfate and concentrated under reduced pressure. The resultant red oil was purified by flash chromatography (silica gel; 10% ethyl acetate/hexanes as eluant) to afford the title compound as an orange, waxy solid. LC/MS 293.1 (M+1).

Step B: 2-(Trifluoromethyl)-5,6,7,8-tetrahydro-1,6-naphthyridine, hydrochloride Treatment of the intermediate from Step A above with 1-chloroethyl chloroformate as described for Intermediate 20, Step C afforded the crude title compound. Trituration with ether provided the title compound as a pale orange powder. LC/MS 203.1 (M+1).

INTERMEDIATE 25

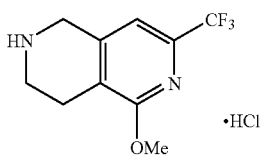

5-Methoxy-7-(trifluoromethyl)-1,2,3,4-tetrahydro-2, 6-naphthridine, hydrochloride Step A:
3,5-Dibromo-6-(trifluoromethylpyridin-2(1H)-one A mixture of 2-hydroxy-6-(trifluoromethyl)pyridine (5.00 g, 30.7 mmol) and N-bromosuccinimide (11.46 g, 64.4 mmol) in N,N-dimethylformamide (20 mL) was stirred at room temperature overnight. The reaction mixture was diluted with ethyl acetate, washed sequentially with water (twice) and saturated brine, dried over sodium sulfate and concentrated under reduced pressure. The residue was purified by flash column chromatography (silica gel; 30% ethyl acetate/hexanes as eluant) to yield the title compound. $^1$H-NMR (400 MHz, CDCl$_3$) δ 8.15 (s, 1H). ESI-MS: 322 (M+H+2).

Step B:
3,5-Dibromo-2-methoxy-6-(trifluoromethyl)pyridine

To a suspension of the compound from Step A above (10.0 g, 31.2 mmol) and silver carbonate (5.73 g, 20.8 mmol) in benzene (40 mL) was added iodomethane (2.33 mL, 37.4 mL). The reaction mixture was stirred at 50° C. under nitrogen in the dark for 24 h. The reaction mixture was diluted with benzene and filtered. The filtrate was washed sequentially with 5% aqueous sodium bicarbonate solution and water (twice), dried over sodium sulfate and concentrated. The residue was purified by flash silica gel column chromatography. $^1$H NMR (400 MHz, CDCl$_3$) δ 8.07 (s, 1H), 4.02 (s, 3H).

Step C: 3,5-Dibromo-2-methoxy-6-(trifluoromethyl) isonicotinaldehyde

To a flame-dried 100 mL round-bottomed flask, was added dry THF (15 mL). The solution was cooled to −78° C. and then N,N-diisopropylamine (0.46 mL, 3.28 mmol), 2.5M n-butyllithium in hexane (1.31 mL, 3.28 mmol), and a solution of the compound from Step B above (1.00 g, 2.99 mmol) in dry THF (10 mL) were added sequentially. The reaction mixture was stirred at −78° C. for 10 min before methyl formate (0.276 mL, 4.49 mmol) was slowly added. After the reaction was stirred for another 2 h, the mixture was warmed and stirred for 30 min at room temperature. Then the mixture was quenched by the addition of saturated aqueous ammonium chloride solution and extracted with ethyl acetate. The combined organic phases were washed sequentially with water and saturated brine, dried over sodium sulfate and concentrated. The residue was purified by flash chromatography (silica gel; 15% ethyl acetate/hexanes as eluant) to yield the title compound. $^1$H NMR (400 MHz, CDCl$_3$) δ 10.10 (s, 1H), 4.11 (s, 3H).

Step D: [3,5-Dibromo-2-methoxy-6-(trifluoromethyl)pyridin-4-yl]methanol

To a solution of 3,5-dibromo-2-methoxy-6-(trifluoromethyl)isonicotinaldehyde (980 mg, 2.7 mmol) in ethanol (10 mL) was added sodium borohydride (102 mg, 2.7 mmol). The reaction mixture was stirred for 20 min, concentrated, and the residue was purified by flash chromatography (silica gel; 50% ethyl acetate/hexanes as eluant) to yield the title compound. $^1$H NMR (400 MHz, CDCl$_3$) δ 5.10 (s, 2H), 4.05 (s, 3H), 2.32 (br s, 1H).

Step E: 4-[[[tert-Butyl(dimethyl)silyl]oxy]methyl]-3, 5-dibromo-2-methoxy-6-(trifluoromethyl)pyridine To a solution of the compound from Step D above (880 mg, 2.41 mmol) in tetrahydrofuran (3 mL) was added sodium hydride (60 weight % dispersion in oil; 107 mg, 2.65 mmol). After 30 min at room temperature, a solution of tert-butyl (dimethyl)silyl chloride (434 mg, 2.89 mmol) was added and the reaction was then stirred for an additional 1 h. The solvent was evaporated and residue was purified by flash chromatography (silica gel; 20% ethyl acetate/hexanes as eluant) to yield the title compound. $^1$H NMR (400 MHz, CDCl$_3$) δ 5.03 (s, 2H), 4.05 (s, 3H), 0.95 (s, 9H), 0.19 (s, 6H). LC/MS: 480 (M+H+2).

Step F: 3-Bromo-4-[[[tert-butyl(dimethyl)silyl]oxy] methyl]-2-methoxy-6-(trifluoromethyl)pyridine To a solution of the compound from Step E above (2.68 g, 3.41 mmol) in tetrahydrofuran (50 mL) at −78° C. was added 2.0M phenyllithium in cyclohexane (1.70 mL, 3.41 mmol). After the reaction was stirred for 5 min, 10% citric acid in THF was added. The mixture was diluted with ethyl ether, washed sequentially with water and saturated brine, dried over sodium sulfate and concentrated. The residue was purified by flash chromatography (silica gel; 10 to 15% ethyl acetate/hexanes gradient elution) to yield the title compound. $^1$H NMR (400 MHz, CDCl$_3$) δ 7.52 (s, 1H), 4.74 (s, 2H), 4.08 (s, 3H), 0.99 (s, 9H), 0.17 (s, 6H). LC/MS: 400/402 (M+H and M+H+2).

Step G: 3-Allyl-4-[[[tert-butyl(dimethyl)silyl]oxy] methyl-2-methoxy-6-(trifluoromethyl)pyridine A mixture of 3-bromo-4-[[[tert-butyl(dimethyl)silyl]oxy] methyl]-2-methoxy-6-(trifluoromethyl)pyridine (2.51 g, 6.27 mmol), allytributyltin (2.92 mL, 9.41 mmol), tetrakis (triphenylphosphine)palladium(0) (750 mg, 0.627 mmol) and toluene (15 mL) was flushed with nitrogen several times. The reaction mixture was stirred at reflux overnight. The reaction was filtered and concentrated under vacuum. The residue was purified by flash chromatography (silica gel; 0 to 5% ethyl acetate/hexanes gradient elution) to yield the title compound. $^1$H NMR (400 MHz, CDCl$_3$) δ 7.55 (s, 1H), 5.85 (m, 1H), 4.93-5.11 (m, 2H), 4.74 (s, 2H), 4.04 (s, 3H), 3.37 (d, J=5 Hz, 2H), 0.99 (s, 9H), 0.17 (s, 6H).

Step H: [4-[[[tert-Butyl(dimethyl)silyl]oxy]methyl]-2-methoxy-6-(trifluoromethyl)pyridin-3-yl]acetaldehyde A mixture of the compound from Step G above (2.62 g, 7.25 mmol), N-methylmorpholine N-oxide (849 mg, 7.25 mmol) and osmium tetroxide (4 wt. % in water, 10 mL, 400 mg) in acetone/water (4:1) (100 mL) was stirred at room temperature overnight. The reaction was quenched by addition of sodium bisulfite (3.50 g, 36 mmol), the acetone was removed under reduced pressure, the mixture was diluted with water, and the product extracted with dichloromethane. The organic layer was dried over sodium sulfate and concentrated, and the residue was stirred with sodium periodate (1.86 g, 8.7 mmol) in methanol/water (1:1) (60 mL) for 30 min. The reaction was filtered and concentrated. The residue was partitioned between ethyl acetate and water and the aqueous layer was extracted with additional ethyl acetate. The combined organic extracts were dried over sodium sulfate and concentrated under reduced pressure, and the residue was purified by flash chromatography (silica gel; 30% ethyl acetate/hexanes as eluant) to yield the title compound. $^1$H NMR (400 MHz, CDCl$_3$) δ 9.68 (t, J=1.5 Hz, 1H), 7.46 (s, 1H), 4.67 (s, 2H), 4.01 (s, 3H), 3.76 (d, J=5 Hz, 2H), 0.96 (s, 9H), 0.13 (s, 6H).

Step I: N-Benzhydryl-2-[4-[[[tert-butyl(dimethyl)silyl]oxy]methyl]-2-methoxy-6-(trifluoromethyl)pyridin-3-yl]ethanamine A mixture of the compound from Step H above (1.55 g, 4.26 mmol), aminodiphenylmethane (1.11 mL, 6.40 mmol), and powdered 4 Å molecular sieves (2.80 g) in dichloromethane (20 mL) was stirred for 30 min. Then sodium triacetoxyborohydride (132 mg, 0.625 mmol) was added. The resultant mixture was stirred overnight, diluted with dichloromethane, filtered, and the filtrate was washed with saturated aqueous sodium carbonate solution. The layers were separated, and the aqueous solution was extracted with dichloromethane. The combined organic layers were dried over sodium sulfate and concentrated under reduced pressure, and the residue was purified by flash chromatography (silica gel; dichloromethane as eluant) to yield the title compound. $^1$H NMR (CDCl$_3$, 400 MHz) δ 7.48 (s, 1H), 7.18-7.38 (m, 10H), 4.84 (s, 1H), 4.78 (s, 2H), 3.81 (s, 3H), 2.77 (m, 4H), 1.62 (br s, 1H), 0.97 (s, 9H), 0.12 (s, 6H). LC/MS: 531 (M+1).

Step J: 2-[4-[[[tert-Butyl(dimethyl)silyl]oxy]methyl]-2-methoxy-6-(trifluoromethyl)pyridin-3-yl]ethanamine To a solution of the compound from Step I above (1.25 g, 2.36 mmol) in absolute ethanol (100 mL) was added 10% palladium on carbon (480 mg). The reaction mixture was placed in a Parr apparatus and shaken under 50 psi of hydrogen for 4 hours. The solution was filtered through a pad of Celite and concentrated in vacuo to yield the title compound. LC/MS: 365 (M+1).

Step K: N-(tert-Butoxycarbonyl)-2-[4-[[[tert-butyl(dimethyl)silyl]oxy]methyl]-2-methoxy-6-(trifluoromethyl)pyridin-3-yl]ethanamine A mixture of the compound from Step J above (880 mg, 2.41 mmol) and di-tert-butyl dicarbonate (630 mg, 2.90 mmol) in dichloromethane (20 mL) was stirred at room temperature for 4 h. The mixture was diluted with additional dichloromethane, washed sequentially with water and saturated brine, dried over sodium sulfate and concentrated. The residue was purified by flash chromatography (silica gel; 20% ethyl acetate/hexanes as eluant) to yield the title compound. $^1$H NMR (400 MHz, CDCl$_3$) δ 7.48 (s, 1H), 4.78 (s, 2H), 4.00 (s, 3H), 3.33 (m, 2H), 2.79 (t, 2H, J=7 Hz).

Step L: N-(tert-Butoxycarbonyl)-2-[4-(hydroxymethyl)-2-methoxy-6-(trifluoromethyl)pyridin-3-yl]ethanamine To a solution of the compound from Step K above (1.12 g, 2.41 mmol) in tetrahydrofuran (20 mL) was added tetrabutylammonium fluoride (11.0M in tetrahydrofuran, 2.41 mL, 2.41 mmol). The reaction was then stirred at room temperature for 10 min and concentrated under reduced pressure. The residue was purified by flash chromatography (silica gel; 20% to 40% ethyl acetate/hexanes gradient elution) to afford the title compound. $^1$H NMR (400 MHz, CDCl$_3$) δ 7.38 (s, 1H), 4.87 (br s, 1H), 4.76 (d, 2H, J=6 Hz), 4.02 (s, 3H), 3.54 (t, 1H), 3.35 (m, 2H), 2.88 (t, 2H, J=6 Hz), 1.38 (s, 9H).

Step M: 5-Methoxy-7-(trifluoromethyl)-1,2,3,4-tetrahydro-2,6-naphthyridine, hydrochloride To a solution of the compound from Step L above (342 mg, 0.976 mmol) and triethylamine (0.82 mL, 5.86 mmol) in dimethyl sulfoxide (3.0 mL) was added a solution of sulfur trioxide-pyridine complex (622 mg, 3.905 mmol) in dimethyl sulfoxide (10 mL). The reaction was then stirred for 40 min, diluted with ethyl acetate, washed sequentially with water and saturated brine, dried over sodium sulfate and concentrated under reduced pressure. The residue (322 mg, 0.924 mmol) was treated with 4N hydrogen chloride in 1,4-dioxane (2 mL, 8.0 mmol), and the mixture was stirred for 4 h. Saturated aqueous sodium bicarbonate solution was added portionwise to adjust the pH of the mixture to 8, and the product was extracted with three portions of dichloromethane. The combined organic extracts were dried over sodium sulfate and concentrated under reduced pressure to afford an oil, which was dissolved in dichloromethane (15 mL). Sodium triacetoxyborohydride (783 mg, 3.7 mmol) was added, and the reaction mixture was stirred overnight at room temperature. Additional dichloromethane (15 mL) was added, followed by saturated aqueous sodium bicarbonate solution (30 mL) and di-tert-butyl dicarbonate (360 mg, 1.657 mmol). The resultant biphasic mixture was stirred for 4 h, and the layers were separated. The aqueous layer was extracted with additional dichloromethane, and the combined organic extracts were washed sequentially with water and saturated brine, dried over sodium sulfate and concentrated under reduced pressure. The residue was purified by flash chromatography (silica gel; 15% ethyl acetate/hexanes as eluant) to afford the BOC-protected amine (191 mg, 41%), which was treated with 4N hydrogen chloride (5 mL) in 1,4-dioxane at room temperature for 18 h. The volatiles were removed under reduced pressure to afford the title compound as a pale yellow solid. LC/MS 233.1 (M+1).

INTERMEDIATE 26

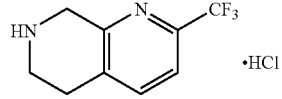

·HCl 2-(Trifluoromethyl)-5,6,7,8-tetrahydro-1,7-naphthyridine, hydrochloride

Step A: 2-(Trifluoromethyl)-7-(triphenylmethyl)-5,6,7,8-tetrahydro-1,7-naphthyridine A mixture of N-trityl-3-piperidone (1.22 g, 3.6 mmol), magnesium sulfate (2.70 g) and pyrrolidine (0.36 mL, 4.3 mmol) in 10 mL of tetrahydrofuran was stirred at room temperature for 72 h. The reaction mixture was filtered, and the filtrate was concentrated under reduced pressure. The resultant crude enamine was dissolved in 13 mL of dry dioxane, cooled to approximately 10° C. and treated dropwise with 4-ethoxy-1,1,1-trifluoro-3-buten-2-one (0.61 mL, 4.3 mmol). The resultant orange solution was allowed to warm to room temperature overnight. Ammonium acetate (0.60 g) was added to the blood-red solution, and the mixture was heated at reflux for 2.5 h, cooled to room temperature and concentrated under reduced pressure. The residue was stirred with 100 mL of dry ether, filtered through a pad of Celite, and concentrated under reduced pressure. The resultant dark red gum was purified by flash chromatography (silica gel; 3% ethyl acetate/hexanes as eluant) to afford impure product. A portion (147 mg) of this material was further purified by preparative TLC (silica gel; 5% ethyl acetate/hexanes as eluant) to afford the title compound as a light yellow foam. LC/MS 365.2 (M+1).

Step B: 2-(Trifluoromethyl)-5,6,7,8-tetrahydro-1,7-naphthyridine, hydrochloride

A solution of the product (94 mg, 0.20 mmol) from Step A above in 0.5 mL of methanol and 2.0 mL of 4.0M hydrogen chloride in 1,4-dioxane was kept at room temperature for 18 h. The reaction mixture was concentrated under a stream of nitrogen, and the residue was triturated with ether. The resultant precipitate was collected and dried in vacuo to afford the title compound as a pale yellow powder. LC/MS 203.1 (M+1).

INTERMEDIATE 27

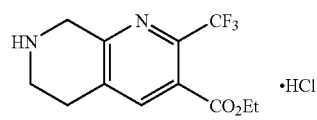

Ethyl 2-(trifluoromethyl)-5,6,7,8-tetrahydro-1,7-naphthyridine-3-carboxylate, hydrochloride Step A: Ethyl 2-(Trifluoromethyl)-7-(triphenylmethyl)-5,6,7,8-tetrahydro-1,7-naphthyridine-3-carboxylate A mixture of N-trityl-3-piperidone (1.22 g, 3.6 mmol), magnesium sulfate (2.70 g) and pyrrolidine (0.36 mL, 4.3 mmol) in 10 mL of tetrahydrofuran was stirred at room temperature for 72 h. The reaction mixture was filtered, and the filtrate was concentrated under reduced pressure. The resultant crude enamine was dissolved in 15 mL of dry dioxane, cooled to approximately 10° C. and treated dropwise with ethyl 2-(ethoxymethylene)-4,4,4-trifluoro-3-oxobutyrate (0.77 mL, 3.9 mmol). The resultant red-orange solution was allowed to warm to room temperature overnight. Ammonium acetate (0.61 g) was added to the blood-red solution, and the mixture was heated at reflux for 3 h, cooled to room temperature and concentrated under reduced pressure. The residue was stirred with 100 mL of dry ether, filtered through a pad of Celite, and concentrated under reduced pressure. The resultant dark red gum was purified by flash chromatography (silica gel; 5% ethyl acetate/hexanes as eluant) to afford the title compound as a light orange foam.

Step B: Ethyl 2-(Trifluoromethyl)-5,6,7,8-tetrahydro-1,7-naphthyridine-3-carboxylate hydrochloride A solution of the product (145 mg) from Step A in 0.5 mL of methanol and 2.5 mL of 4.0M hydrogen chloride in dioxane was kept at room temperature for 3 h. The reaction mixture was concentrated under a stream of nitrogen, and the residue was triturated with ether. The resultant precipitate was collected and dried in vacuo to afford the title compound as a light red powder. LC/MS 275.1 (M+1).

INTERMEDIATE 28

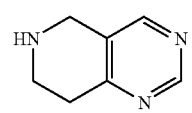

5,6,7,8-Tetrahydropyrido[4,3-d]pyridine

Step A: tert-Butyl 4-oxo-3-(dimethylaminomethylidene)-1-piperidinecarboxylate

A solution of tert-butyl 4-oxo-1-piperidinecarboxylate (8.73 g, 44 mmol) and N,N-dimethylformamide dimethyl acetal (5.8 mL, 44 mmol) in 80 mL of dry N,N-dimethylformamide was warmed at 80° C. for 18 h. The solution was cooled and concentrated under reduced pressure, and the residue was partitioned between ethyl acetate and water. The mixture was filtered through a pad of Celite, and the organic layer was separated, washed with saturated brine, dried over magnesium sulfate and concentrated under reduced pressure to afford the title compound as an orange oil.

Step B: 6-(tert-Butoxycarbonyl)-5,6,7,8-tetrahydropyrido[4,3-d]pyrimidine

Formamidine acetate (472 mg, 4.52 mmol) in 15.0 mL of absolute ethanol was treated with sodium ethoxide (21 wt % solution in ethanol; 1.7 mL). After 30 min, a solution of the product from Step A above (1.15 g) in 8 mL of absolute ethanol was added, and the mixture was warmed at reflux for 18 h. The dark solution was cooled to room temperature and concentrated under reduced pressure, and the residue was partitioned between ethyl acetate and water. The organic layer was separated, washed with brine, dried over magnesium sulfate and concentrated to an orange oil. Purification by flash chromatography (silica gel; 2% methanol/dichloromethane as eluant) afforded the title compound as a light yellow gum.

Step C: 5,6,7,8-Tetrahydropyrido[4,3-d]pyrimidine

A solution of the product from Step B above (730 mg) in 10 mL of dichloromethane was cooled to 0° C. and treated dropwise with 5 mL of trifluoroacetic acid. The solution was warmed to room temperature and, after 1 h, concentrated under reduced pressure. The residue was dissolved in methanol and applied to an ion-exchange column (Varian Bond-Elut SCX, 5 g; preconditioned with methanol). The column was washed several times with methanol, and the amine product was eluted with 1.0M ammonia-methanol. The fractions containing product were concentrated under reduced pressure to afford the title compound as an orange oil. LC/MS 136.1 (M+1).

INTERMEDIATE 29

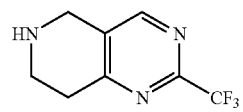

2-(Trifluoromethyl)-5,6,7,8-tetrahydropyrido[4,3-d]pyrimidine

Step A: 6-(tert-Butoxycarbonyl)-2-(trifluoromethyl)-5,6,7,8-tetrahydropyrido[4,3-d]pyrimidine Reaction of tert-butyl 4-oxo-3-(dimethylaminomethylidene)-1-piperidinecarboxylate (1.78 g) from Intermediate 28, Step A with trifluoroacetamidine (0.86 g) according to the procedure described for Intermediate 28, Step B, and purification by flash chromatography (silica gel; 18% ethyl acetate/hexanes as eluant), afforded the title compound as a viscous orange oil.

Step B: 2-(Trifluoromethyl)-5,6,7,8-tetrahydropyrido[4,3-d]pyrimidine, trifluoroacetatic acid salt Reaction of the product from Step A above with trifluoroacetic acid in dichloromethane according to the procedure outlined for Intermediate 28, Step C afforded the title compound as a white powder. LC/MS 204.0 (M+1).

INTERMEDIATE 30

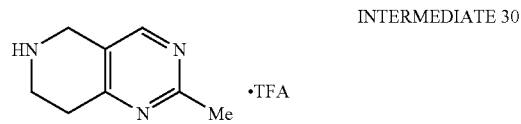

2-Methyl-5,6,7,8-tetrahydropyrido[4,3-d]pyrimidine, trifluoroacetate salt

Step A: 6-(tert-Butoxycarbonyl)-2-methyl-5,6,7,8-tetrahydropyrido[4,3-d]pyrimidine Reaction of tert-butyl 4-oxo-3-(dimethylaminomethylidene)-1-piperidinecarboxylate (1.15 g) from Intermediate 28, Step A with acetamidine acetate (0.54 g) according to the procedure described for Intermediate 28, Step B, and purification by flash chromatography (silica gel; 2% methanol/dichloromethane as eluant) afforded the title compound as a viscous orange oil.

Step B: 2-Methyl-5,6,7,8-tetrahydropyrido[4,3-d]pyrimidine, trifluoroacetate salt Reaction of the product from Step A above with trifluoroacetic acid in dichloromethane according to the procedure outlined for Intermediate 28, Step C afforded the title compound as a light orange powder. LC/MS 150.1 (M+1).

INTERMEDIATE 31

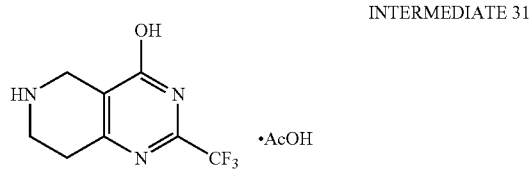

4-Hydroxy-2-(trifluoromethyl)-5,6,7,8-tetrahydropyrido[4,3-d]pyrimidine, acetic acid salt

Step A: 6-Benzyl-2-(trifluoromethyl)-5,6,7,8-tetrahydropyrido[4,3-d]pyrimidin-4-ol To a solution of ethyl 1-benzyl-4-oxo-3-piperidinecarboxylate hydrochloride (2.68 g, 10.3 mmol) in 25 mL of absolute ethanol was added 13 mL of 2.68M sodium ethoxide in ethanol dropwise with stirring and cooling in a water bath. After 10 min, trifluoroacetamide (0.92 g, 8.21 mmol) was added dropwise. The reaction stirred at reflux (90° C.) for 16 h. The mixture was cooled to ambient temperature, concentrated in vacuo, partitioned between water and ethyl acetate, and extracted with three portions of ethyl acetate. The organic phase was sequentially washed with brine, dried over magnesium sulfate, and concentrated in vacuo. Purification by flash chromatography (silica gel, 97:7 dichloromethane/methanol) gave the title compound. LC/MS 310 (M+1).

Step B: 4-Hydroxy-2-(trifluoromethyl)-5,6,7,8-tetrahydropyrido[4,3-d]pyrimidine, acetic acid salt To a solution of 6-benzyl-2-(trifluoromethyl)-5,6,7,8-tetrahydropyrido[4,3-d]pyrimidin-4-ol (0.08 g, 0.26 mmol) in 5.0 mL of glacial acetic acid was added 70 mg of 5% Pd/C. The reaction was shaken (Parr shaker) at room temperature under hydrogen at 42 psi for 13 h. Removal of the catalyst by filtration, followed by concentration and trituration with diethyl ether gave the title compound. LC/MS 220 (M+1).

INTERMEDIATE 32

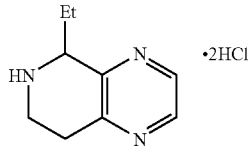

5-Ethyl-5,6,7,8-tetrahydropyrido[3,4-b]pyrazine dihydrochloride

Step A: Phenyl 5-ethylpyrido[3,4-b]pyrazine-6(5H)-carboxylate

A solution of phenyl chloroformate (0.200 mL, 250 mg, 1.59 mmol) in tetrahydrofuran (3.5 mL) was added over 20 min to a solution of 200 mg (1.53 mmol) of pyrido[3,4-b]pyrazine (prepared according to the procedure of F. F. Duarte and F. D. Popp, *J. Heterocyclic Chem.*, 31: 819-823 (1994)) in tetrahydrofuran (7.5 mL) cooled in a −25° C. bath. After 10 min, ethylmagnesium bromide (1.0M in tetrahydrofuran, 1.54 mL, 1.54 mmol) was added over 10 min. The mixture was allowed to warm to 0° C. over 1 h. After an additional 30 min at 0° C., water (20 mL) was added and the mixture was extracted with ethyl acetate (50 mL). The organic layer was washed with saturated sodium bicarbonate solution (10 mL) followed by saturated aqueous brine (10 mL). The aqueous layers were extracted in succession with ethyl acetate (25 mL) and the organic layers were dried over sodium sulfate, decanted, and evaporated. Purification by flash chromatography (silica gel, 4-5% ethyl acetate in 1:1 hexanes/dichloromethane) gave the title compound as a colorless syrup. LC/MS 282 (M+1).

Step B: Phenyl 5-ethyl-7,8-dihydropyrido[3,4-b]pyrazine-6(5H)-carboxylate

Catalyst (10% palladium on carbon, 140 mg) was added to a solution of phenyl 5-ethylpyrido[3,4-b]pyrazine-6(5H)-carboxylate (238 mg, 0.85 mmol) in ethyl acetate (6.0 mL), and the resultant mixture was stirred under hydrogen (1 atm) for 7.5 h. Filtration through Celite® and evaporation of the solvent gave the crude product. Purification by flash chromatography (silica gel, 6-15% ethyl acetate/dichloromethane) gave the title compound as a colorless oil. LC/MS 284 (M+1).

Step C: tert-Butyl 5-ethyl-7,8-dihydropyrido[3,4-b]pyrazine-6(5H)-carboxylate

Potassium tert-butoxide (11.0M in tetrahydrofuran, 0.7 mL, 0.7 mmol) was added over 3 min to a solution of phenyl 5-ethyl-7,8-dihydropyrido[3,4-b]pyrazine-6(5H)-carboxylate (91 mg, 0.32 mmol) in tetrahydrofuran (1.8 mL) cooled in a −20 to −30° C. bath. After 30 min, the bath was removed and stirring was continued for 75 min. The mixture was added to saturated aqueous sodium bicarbonate solution (10 mL) which was then extracted with two portions of ethyl acetate (35 mL and 15 mL). The organic layers were washed in succession with saturated aqueous brine (10 mL), dried over sodium sulfate, decanted, and evaporated. Purification by flash column chromatography (silica gel, 15% ethyl acetate/hexanes) gave the title compound as a colorless oil. $^1$H NMR (500 MHz, CD$_3$OD) δ 8.43 (d, 1H, J=2 Hz), 8.40 (d, 1H, J=2 Hz), 5.17-5.02 (bm, 1H), 4.40-4.25 (bm, 1H), 3.37-3.20 (bm, 1H), 3.04 (ddd, 1H, J=17, 12, 6 Hz), 2.90 (dd, 1H, J=17, 4 Hz), 2.10-2.00 (m, 1H), 1.87-1.76 (m, 1H), 1.49 (s, 9H), 1.04 (bt, 3H). LC/MS 208 (M+1-56).

Step D: 5-Ethyl-5,6,7,8-tetrahydropyrido[3,4-b]pyrazine dihydrochloride

A solution methanolic hydrogen chloride (approx. 1.6M, 1.5 mL) was added to tert-butyl 5-ethyl-7,8-dihydropyrido[3,4-b]pyrazine-6(5H)-carboxylate (29 mg, 0.11 mmol) dissolved in 0.25 mL of methanol. After 3.5 h, the solution was concentrated under a stream of nitrogen. Methanol (two portions) was added, with evaporation of the solvent after each addition, to give the title compound as a hygroscopic foam. $^1$H NMR (500 MHz, CD$_3$OD) δ 8.57 (d, 1H, J=3 Hz), 8.54 (d, 1, J=3 Hz), 4.57 (dd, 1H, J=8, 5 Hz), 3.77 (ddd, 1H, J=13, 6, 5 Hz), 3.59 (ddd, 1H, J=10, 6 Hz), 3.37 (ddd, 1H, J=18, 10, 7 Hz), 3.35 (dt, 1H, J=18, 5 Hz), 2.51-2.41 (m, 1H), 2.06-1.96 (m, 1H), 1.18 (t, 3H, J=8 Hz). LC/MS 164 (M+1).

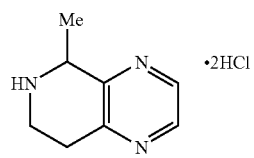

INTERMEDIATE 33

5-Methyl-5,6,7,8-tetrahydropyrido[3,4-b]pyrazine dihydrochloride

The title compound was prepared using essentially the same procedure described for INTERMEDIATE 32, with methylmagnesium bromide used in place of ethylmagnesium bromide in Step A. $^1$H NMR (500 MHz, CD$_3$OD) δ 8.58 (d, 1H, J=3 Hz), 8.55 (d, 1H, J=3 Hz), 4.74 (q, 1H, J=7 Hz), 3.77 (dt, 1H, J=13, 6 Hz), 3.62 (ddd, 1H, J=13, 9, 6 Hz), 3.38 (ddd, 1H, J=18, 9, 6 Hz), 3.27 (dt, J=18, 6 Hz), 1.77 (d, 3H, J=7 Hz).

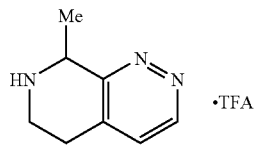

INTERMEDIATE 34

8-Methyl-5,6,7,8-tetrahydropyrido[3,4-c]pyridazine, trifluoroacetic acid salt

Step A: 2-Methylpiperidin-3-ol

To a solution of 5.0 g (45.8 mmol) of 3-hydroxy-2-methylpyridine in methanol was added 5.5 g of rhodium on alumina powder. The reaction was stirred under an atmosphere of hydrogen at 50 psi overnight. The mixture was filtered through a pad of Celite and the filtrate was concentrated to give the title compound as a viscous oil.

Step B: tert-Butyl 3-hydroxy-2-methylpiperidine-1-carboxylate

To a solution of 4.80 g (41.7 mmol) of 2-methylpiperidin-3-ol (Step A) in 200 mL of dichloromethane were added N,N-diisopropylethylamine (7.26 mL, 41.7 mmol) and di-tert-butyl dicarbonate (9.10 g, 41.7 mmol). The reaction was stirred at ambient temperature for 4 h. Then the mixture was partitioned between dichloromethane and 0.5N aqueous sodium bicarbonate solution. The aqueous phase was extracted with three portions of dichloromethane. The combined organic layers were washed with brine, dried over magnesium sulfate, and concentrated. Purification by flash chromatography on a Biotage® system (silica gel, eluting with 20% ethyl acetate/hexane to 60% ethyl acetate/hexane) gave the title compound. LC/MS 160 (M+1-56).

Step C: tert-Butyl 2-methyl-3-oxopiperidine-1-carboxylate

A solution of oxalyl chloride (4.06 mL, 46.5 mmol) in 50 mL of dichloromethane was cooled to −78° C. and 4.95 mL (69.8 mmol) of dimethyl sulfoxide was added slowly and the mixture was stirred at −78° C. for 10 min. Then a solution of 5.00 g (23.3 mmol) of tert-butyl 3-hydroxy-2-methylpiperidine-1-carboxylate (Step B) in 5 mL of dichloromethane was added dropwise to above mixture. The mixture was stirred at −78° C. for 20 min, then 40.5 mL (232 mmol) of N,N-diisopropylethylamine was added to the mixture. The reaction was warmed to ambient temperature and continued to stir at ambient temperature for 1 h. The mixture was partitioned between dichloromethane and water. The aqueous phase was extracted with three potions of dichloromethane. The combined organic layers were washed with brine, dried over magnesium sulfate, and concentrated. Purification by flash chromatography on a Biotage®D system (silica gel, eluting with 10% ethyl acetate/hexane to 30% ethyl acetate/hexane) gave the title compound. LC/MS 214 (M+1).

Step D: tert-Butyl 4-[(2E)-1-hydroxyl-3-phenylprop-2-enyl]-2-methyl-3-oxopiperidine-1-carboxylate To a solution of 2.14 mL (15.3 mmol) of N,N-diisopropylamine in 50 mL of tetrahydrofuran at −78° C. was added 7.96 mL (15.6 mmol, 2.5M in hexane) of n-butyl lithium and the mixture was stirred at −78° C. for 10 min. The reaction was warmed to 0° C. and stirred at 0° C. for 15 min. The mixture was cooled down to −78° C. again, and a solution 2.50 g (11.7 mmol) of tert-butyl 2-methyl-3-oxopiperidine-1-carboxylate (Step C) in 5 mL of tetrahydrofuran was added to the mixture slowly. The mixture was stirred at −78° C. for 1 h. Then 1.77 mL (14.9 mmol) of trans-cinnamaldehyde in 5 mL of tetrahydrofuran (pre-cooled to −78° C.) was added to the reaction mixture and the reaction was stirred at −78° C. for 5 h. The reaction was quenched with saturated aqueous sodium bicarbonate solution and extracted with three portions of ether. The combined organic layers were washed with brine, dried over magnesium sulfate, and concentrated. Purification by flash chromatography on a Biotage® system (silica gel, eluting with 10% ethyl acetate/hexane to 30% ethyl acetate/hexane) gave the tide compound. LC/MS 368 (M+23).

Step E: tert-Butyl 4-(1-hydroxyl-2-oxoethyl)-2-methyl-3-oxopiperidine-1-carboxylate Ozone gas was bubbled into a solution of 0.450 g (1.30 mmol) of tert-butyl 4-[(2E)-1-hydroxyl-3-phenylprop-2-enyl]-2-methyl-3-oxopiperidine-1-carboxylate (Step D) in 10 mL of methanol and 10 mL of dichloromethane at −78° C. until the solution turned blue. The reaction was quenched with dimethyl sulfide, warmed to ambient temperature, and stirred for 1 h. The mixture was concentrated in vacuo and purified by flash chromatography on a Biotage® system (silica gel, eluting with 20% ethyl acetate/hexane to 60% ethyl acetate/hexane), affording the title compound.

Step F: tert-Butyl 8-methyl-5,8-dihydropyrido[3,4-c]pyridazine-7(6H)-carboxylate To a solution of 70.0 mg (0.258 mmol) of tert-butyl 4-(1-hydroxyl-2-oxoethyl)-2-methyl-3-oxopiperidine-1-carboxylate (Step E) in 12 mL of benzene was added hydrazine. The reaction was heated to reflux for 3.5 h and concentrated to afford the title compound. LC/MS 194 (M+1-56).

Step G: 8-Methyl-5,6,7,8-tetrahydropyrido[3,4-c]pyridazine, trifluoroacetate salt To 70.0 mg (0.258 mmol) of tert-butyl 8-methyl-5,8-dihydropyrido[3,4-c]pyridazine-7(6H)-carboxylate (Step F) was added 2 mL of trifluoroacetic acid. The reaction was stirred at ambient temperature for 1 h and concentrated to afford the title compound. LC/MS: 150 (M+1).

INTERMEDIATE 35

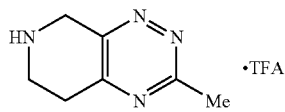

3-Methyl-5,6,7,8-tetrahydropyrido[4,3-e][1,2,4]triazine, trifluoroacetic acid salt

Step A: tert-Butyl 3,6-dihydropyridine-1(2H)-carboxylate

To a solution of 10 g (117 mmol) of commercially available 1,2,3,6-tetrahydropyridine in 240 mL of dichloromethane stirred at 0° C. was added 31.5 g (140 mmol) of di-tert-butyl dicarbonate, and stirring was continued at 0° C. under nitrogen for several minutes. Then the cooling bath was removed, and the solution was stirred at ambient temperature for 2.5 h. The solution was concentrated in vacuo, and the residue was purified by flash chromatography (silica gel, 0-5% methanol/dichloromethane followed by 9:1 hexanes/ethyl acetate) to afford the title compound [For a modified preparation, see Nordmann et al., *J. Med. Chem.*, 28: 1109-1111 (1985)]. $^1$H NMR (500 MHz, CDCl$_3$) δ 5.84 (br m, 1H), 5.67 (br apparent s, 1H), 3.90 (apparent s, 2H), 3.50 (t, J=5.6 Hz, 2H), 2.15 (br apparent s, 2H), 1.49 (s, 9H). LC/MS: 128 (M+1-isobutene).

Step B: tert-Butyl 3,4-dihydroxypiperidine-1-carboxylate

To a stirred solution of 21 g (115 mmol) of tert-butyl 3,6-dihydropyridine-1(2H)-carboxylate from Step A in 5 mL of tetrahydrofuran was added 300 mL of water, followed by 18 g (149 mmol) of potassium chlorate. Then a solution of 200 mg of osmium tetroxide in 30 mL of water was added slowly in portions. The mixture was stirred at 80° C. for 16 h. At this time, additional portions of potassium chlorate (11.2 g, 92 mmol) and osmium tetroxide (138 mg) were added, and stirring was continued at 80° C. for another 3.5 h. The reaction mixture was partitioned between diethyl ether and water. The aqueous phase was extracted with dichloromethane and then concentrated in vacuo. The resultant residue from the aqueous phase was extracted with tetrahydrofuran. The combined organic fractions were concentrated in vacuo, and the residue was purified by flash chromatography (silica gel, 0-5% methanol/dichloromethane) to give the title compound. $^1$H NMR (500 MHz, CDCl$_3$) δ 5.93 (br s, 2H), 3.92 (m, 1H)-3.83 (m, 1H), 3.63 (m, 2H), 3.39 (m, 1H), 3.25 (m, 1H), 1.84 (m, 1H), 1.72 (m, 1H), 1.47 (s, 9H). LC/MS: 240 (M+1).

Step C: tert-Butyl 3,4-dioxopiperidine-1-carboxylate

In a dried flask, a solution of 8.8 mL (9.7 g, 125 mmol) of anhydrous dimethyl sulfoxide in 400 mL of anhydrous dichloromethane was stirred under nitrogen at −60° C. as 15.9 mL (23.6 g, 113 mmol) of trifluoroacetic anhydride was added dropwise. The resultant solution was stirred at −60° C. for 20 min, at which time a solution of 8.5 g (39.1 mmol) of tert-butyl 3,4-dihydroxypiperidine-1-carboxylate from Step B in 100 mL of anhydrous dichloromethane was added via cannula. The solution was stirred at −60° C. for 1.5 h, during which time some precipitation occurred. Then 36.2 mL (26.3 g, 260 mmol) of triethylamine was added, and stirring was continued at −60° C. for an additional 30 min. The reaction mixture was concentrated in vacuo, and the residue was purified by flash chromatography (silica gel, 0-30% ethyl acetate/hexanes) to yield the title compound, which may exist as a mixture of tautomers. $^1$H NMR (500 MHz, CDCl$_3$) δ 7.8-7.6 (br m, <1H), 5.3 (br apparent s, ≦1H), 4.00 (m, 2H), 2.69 (t, J=7.5 Hz, 2H), 1.57 (s, 9H). LC/MS: 214 (M+1).

Step D: tert-Butyl 3-methyl-5,8-dihydropyrido[4,3-e][1,2,4]triazine-7(6H)-carboxylate In analogy to a general literature method (Neunhoeffer and Metz, *Liebigs Ann. Chem.*, 1476-1495 (1983)), a solution of 377 mg (1.88 mmol) of acetamidrazone hydriodide (ethanimidohydrazide hydriodide), prepared from methyl ethanimidothioate hydriodide (Singh et al., *Indian J. Chem.*, 21B: 272-273 (1982)) according to the procedure of Zelenin et al., *J. Gen. Chem. USSR*, 18: 1410-1415 (1982)) in 10 mL of absolute ethanol was treated with 0.36 mL (268 mg, 2.07 mmol) of N,N-diisopropylethylamine, and the solution was stirred under nitrogen at room temperature for 10 min. To this was then added dropwise a solution of 400 mg (1.88 mmol) of tert-butyl 3,4-dioxopiperidine-1-carboxylate from Step C. After being stirred initially at room temperature, the reaction mixture was heated at reflux for 4.5 h. At this time, an additional 96 mg (0.48 mmol) of the amidrazone salt was added, and stirring at reflux was continued for 3 h. The reaction mixture was concentrated in vacuo, and the residue was purified by flash chromatography (silica gel, 30-70% ethyl acetate/hexanes, then 95:5 dichloromethane/methanol) to give the title compound. The regiochemistry was assigned in analogy to Example 36, Step A, in which both possible regioisomers were isolated and assigned. $^1$H N (500 MHz, CDCl$_3$) δ 4.93 (s, 2H), 3.82 (m, 2H), 3.02 (m, 2H), 2.85 (s, 3H, 1.52 (s, 9H). LC/MS: 195 (M+1-isobutene).

Step E: 3-Methyl-5,6,7,8-tetrahydropyrido[4,3-e][1,2,4]triazine, trifluoroacetic acid salt A solution of 58 mg (0.23 mmol) of tert-butyl 3-methyl-5,8-dihydropyrido[4,3-e][1,2,4]triazine-7(6H)-carboxylate from Step D in 2 mL of trifluoroacetic acid and 2 mL of dichloromethane was stirred at room temperature for 20 min and then concentrated in vacuo. Trituration of the residue with diethyl ether gave the title compound as a trifluoroacetate salt. $^1$H NMR (500 MHz, CD$_3$OD) δ 4.16 (apparent s, 2H), 3.96 (m, 2H), 2.28 (s, 3H). (The signal for the methylene group at the 8-position may be obscured by the water peak at δ 4.88.) LC/MS: 151 (+1).

INTERMEDIATE 36

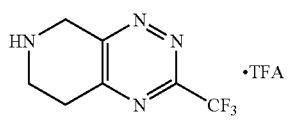

3-(Trifluoromethyl)-5,6,7,8-tetrahydropyrido[4,3-e][1,2,4]triazine, trifluoroacetic acid salt Step A: tert-Butyl 3-(trifluoromethyl)-5,8-dihydropyrido[4,3-e][1,2,4]triazine-7(6H)-carboxylate This material was obtained by reaction of tert-butyl 3,4-dioxopiperidine-1-carboxylate from Intermediate 35, Step C, with trifluoroacetamidrazone (2,2,2-trifluoroethanimidohydrazide), prepared from methyl 2,2,2-trifluoroethanimidoate according to the procedure of Brown and Wetzel, J. Org. Chem., 30: 3729-3733 (1965), essentially as described for Intermediate 35, Step D, except that completion of the condensation and ring closure required heating in 2-methoxyethanol at reflux for 2 d. Purification of the evaporation residue by flash chromatography (silica gel, 30% ethyl acetate/hexanes) provided the crude title compound in addition to a minor amount of the other regioisomer, tert-butyl 3-(trifluoromethyl)-7,8-dihydropyrido[3,4-e][1,2,4]triazine-6(5H)-carboxylate. Further purification of the product was achieved by preparative HPLC (YMC Pro C18 column, gradient elution, 40-70% acetonitrile/water containing 0.1% trifluoroacetic acid). To prevent decomposition during isolation, excess N,N-diisopropylethylamine was added to the pooled product fractions to neutralize the trifluoroacetic acid prior to concentration in vacuo. The residue was partitioned between ethyl acetate and 5% aqueous citric acid solution. The organic phase was washed with brine, dried over sodium sulfate, and concentrated to give the pure title compound. The regioisomers were assigned on the basis of $^1$H NMR chemical shift differences reported in several papers for analogous compounds. (See, for example, Konno et al., Heterocycles, 22: 2241-2244 (1984) and Neunhoeffer and Böhnisch, Liebigs Ann. Chem., 153-162 (1976).) $^1$H NMR (500 MHz, CDCl$_3$) δ 5.08 (s, 2H), 3.90 (m, 2H), 3.21 (m, 2H), 1.54 (s, 9H). LC/MS: 249 (M+1-isobutene).

Step B: 3-(Trifluoromethyl)-5,6,7,8-tetrahydropyrido[4,3-e][1,2,4]triazine, trifluoroacetic acid salt Essentially following the procedure used for Example 35, Step E, tert-butyl 3-(trifluoromethyl)-5,8-dihydropyrido[4,3-e][1,2,4]triazine-7(6H)-carboxylate was deprotected with trifluoroacetic acid to give the title compound as a trifluoroacetate salt. LC/MS: 205 (M+1).

INTERMEDIATE 37

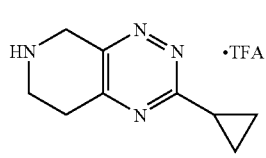

3-Cyclopropyl-5,6,7,8-tetrahydropyrido[4,3-e][1,2,4]triazine, trifluoroacetic acid salt Step A: tert-Butyl 3-(cyclopropyl)-5,8-dihydropyrido[4,3-e[]1,2,4]triazine-7(6H)-carboxylate Following a one-pot procedure for conversion of an amidine via its amidrazone to a 1,2,4-triazine (Neunhoeffer and Weischedel, Liebigs Ann. Chem., 749: 16-23 (1971)), a solution of 175 mg (1.45 mmol) of commercially available cyclopropylcarbamidine hydrochloride in 4 mL of anhydrous ethanol was treated dropwise with 0.452 mL (46.1 mg, 1.45 mmol) of anhydrous hydrazine. After being stirred for about 20 min, 0.271 mL (201 mg, 1.56 mmol) of N,N-diisopropylethylamine was added. The resultant solution was added to a suspension of 300 mg (1.41 mmol) of tert-butyl 3,4-dioxopiperidine-1-carboxylate from Intermediate 35, Step C, in a mixture of 1 mL of ethanol and 5 mL of methanol. The resultant solution was stirred at room temperature for 2 d and then concentrated in vacuo. The residue was purified by flash chromatography (silica gel, 30-50% ethyl acetate/hexanes) followed by preparative TLC (silica gel, 2:3 dichloromethane/ethyl acetate) to afford the title compound, which was separated from the minor regioisomer, tert-butyl 3-cyclopropyl-7,8-dihydropyrido[3,4-e][1,2,4]triazine-6(5H)-carboxylate. Regioisomers were assigned as described for Intermediate 36, Step A. $^1$H NMR (500 MHz, CDCl$_3$) δ 4.92 (s, 2H), 3.81 (m, 2H), 2.98 (m, 2H), 2.47 (m, 1H), 1.54 (s, 9H), 1.24-1.19 (m, 4H). LC/MS: 221 (M+1-isobutene).

Step B: 3-Cyclopropyl-5,6,7,8-tetrahydropyrido[4,3-e][1,2,4]triazine, trifluoroacetic acid salt Essentially following the procedure used for Example 35, Step E, tert-butyl 3-(cyclopropyl)-5,8-dihydropyrido[4,3-e][1,2,4]triazine-7(6H)-carboxylate from Step A was deprotected with trifluoroacetic acid to give the title compound as a trifluoroacetate salt. LC/MS: 177 (M+1).

INTERMEDIATE 38

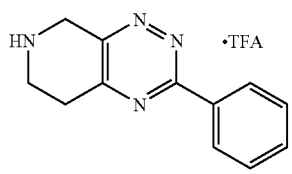

3-Phenyl-5,6,7,8-tetrahydropyrido[4,3-e][1,2,4]triazine, trifluoroacetic acid salt Step A: tert-Butyl 3-phenyl-5,8-dihydropyrido[4,3-e][2,4]triazine-7(6H)-carboxylate Essentially following the procedure used for Intermediate 35, Step D, tert-butyl 3,4-dioxopiperidine-1-carboxylate from Intermediate 35, Step C, was reacted with benzamidrazone hydriodide (benzenecarboximidohydrazide hydriodide), prepared according to the procedure of Doyle and Kurzer, *Synthesis*, 583-584 (1974), to give the title compound, which was separated from the other regioisomer, tert-butyl 3-phenyl-7,8-dihydropyrido[3,4-e][1,2,4]triazine-6(5H)-carboxylate. Regioisomers were assigned as described for Intermediate 36, Step A. $^1$H NMR (500 MHz, CDCl$_3$) δ 8.56 (m, 21), 7.58 (m, 3H), 5.03 (s, 2H), 3.90 (t, J=6 Hz, 2H), 3.15 (t, J=6 Hz, 2H), 1.57 (s, 9H). LC/MS: 257 (M+1-isobutene).

Step B: 3-Phenyl-5,6,7,8-tetrahydropyrido[4,3-e][1,2,4]triazine, trifluoroacetic acid salt Essentially following the procedure used for Example 35, Step E, tert-butyl 3-phenyl-5,8-dihydropyrido[4,3-e][1,2,4]triazine-7(6H)-carboxylate from Step A was deprotected with trifluoroacetic acid to give the title compound as a trifluoroacetate salt. LC/MS: 213 (M+1).

INTERMEDIATE 39

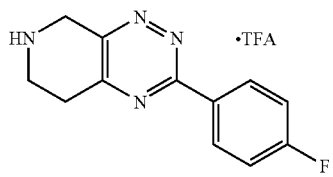

3-(4-Fluorophenyl)-5,6,7,8-tetrahydropyrido[4,3-e][1,2,4]triazine, trifluoroacetic acid salt Step A: tert-Butyl 3-(4-fluorophenyl)-5,8-dihydropyrido[4,3-e][1,2,4]triazine-7(6H)-carboxylate and tert-butyl 3-(4-fluorophenyl)-7,8-dihydropyrido[3,4-e][1,2,4]triazine-6(5H)-carboxylate Essentially following the procedure used for Intermediate 37, Step A, 4-fluorobenzamidine hydrochloride (Terpinski et al., *Magn. Reson. Chem.*, 25: 923-927 (1987); general method: Moss et al., *J. Am. Chem. Soc.*, 107: 2743-2748 (1985)) was reacted with anhydrous hydrazine and then with tert-butyl 3,4-dioxopiperidine-1-carboxylate from Intermediate 35, Step C. Purification of the residue by preparative TLC (silica gel, 7:3 dichloromethane/ethyl acetate) afforded the two title compounds. Regioisomers were assigned as described for Intermediate 36, Step A.

tert-Butyl 3-(4-Fluorophenyl)-5,8-dihydropyrido[4,3-e][1,2,4]triazine-7(6H)-carboxylate: $^1$H NMR (500 MHz, CDCl$_3$) δ 8.56 (m, 2H), 7.23 (m, 2H), 5.00 (s, 2H), 3.88 (m, 2H), 3.11 (m, 2H), 1.55 (s, 9H). LC/MS: 331 (M+1).

tert-Butyl 3-(4-fluorophenyl)-7,8-dihydropyrido[3,4-e][1,2,4]triazine-6(5H)-carboxylate: $^1$H NMR (500 MHz, CDCl$_3$) δ 8.55 (m, 2H), 7.23 (m, 2H), 4.79 (s, 2H), 3.89 (m, 2H), 3.31 (m, 2H), 1.55 (s, 9H). LC/MS: 331 (M+1).

Step B: 3-(4-Fluorophenyl)-5,6,7,8-tetrahydropyrido[4,3-e][1,2,4]triazine, trifluoroacetic acid salt Essentially following the procedure used for Example 35, Step E, tert-butyl 3-(4-fluorophenyl)-5,8-dihydropyrido[4,3-e][1,2,4]triazine-7(6H)-carboxylate from Step A was deprotected with trifluoroacetic acid to give the title compound as a trifluoroacetate salt. LC/MS: 231 (M+1).

INTERMEDIATE 40

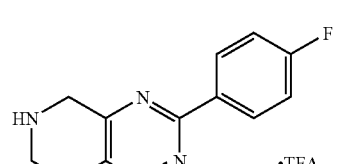

3-(4-Fluorophenyl)-5,6,7,8-tetrahydropyrido[3,4-e][1,2,4]triazine, trifluoroacetic acid sat Essentially following the procedure used for Example 35, Step E, tert-butyl 3-(4-fluorophenyl)-5,8-dihydropyrido[4,3-e][1,2,4]triazine-7(6H)-carboxylate from Intermediate 39, Step A, was deprotected with trifluoroacetic acid, except that reaction time was limited to 4 min in order to prevent decomposition. LC/MS: 231 (M+1).

Note that, in this case, reaction time should also be kept short for removal of the N-Boc protecting group from the acylated product formed in the next step.

EXAMPLE 1

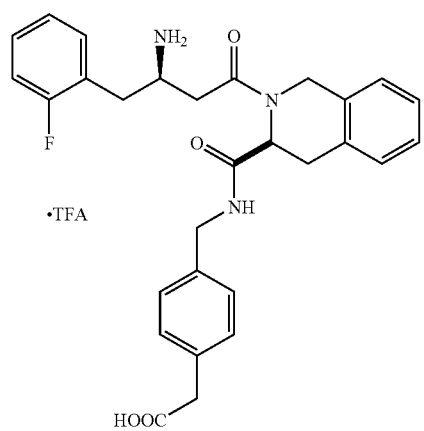

[4-[[[[(3S)-2-[(3R)-3-Amino-4-(2-fluorophenyl)bu-tanoyl]-1,2,3,4-tetrahydroisoquinolin-3-yl]carbonyl]amino]methyl]phenyl]acetic acid trifluoroacetic acid salt Step A: Methyl [4-[[[[(3S)-2-[(3R)-3-[(tert-butoxycarbonyl)amino]-4-(2-fluorophenyl)butanoyl]-1,2,3,4-tetrahydroisoguinolin-3-yl]carbonyl]amino]methyl]phenyl]acetate A mixture of methyl [4-[[[(3S)-1,2,3,4-tetrahydroisoquinolin-3-ylcarbonyl]amino]methyl]phenyl]acetate trifluoroacetic acid salt (Intermediate 16, 45 mg, 0.10 mmol), commercially available (3R)-3-[(tert-butoxycarbonyl)amino]4-(2-fluorophenyl)butanoic acid (42 mg, 0.14 mmol), 1-(3-(dimethylamino)propyl]-3-ethylcarbodiimide hydrochloride (EDC; 29 mg, 0.15 mmol), 1-hydroxybenzotriazole (HOBt; 20 mg, 0.15 mmol) and N,N-diisopropylethylamine (0.052 mL, 0.30 mmol) in 1.0 mL of dichloromethane was stirred at room temperature for 2 h. The reaction mixture was subjected directly to flash chromatography (silica gel; 60% ethyl acetate/hexanes as eluant) to afford the title compound as a viscous oil.

Step B: [4-[[[[(3S)-2-[(3R)-3-[(tert-Butoxycarbonyl)amino]-4-(2-fluorophenyl)butanoyl]-1,2,3,4-tetrahydroisoguinolin-3-yl]carbonyl]amino]methyl]phenyl]acetic acid, lithium salt To a stirred solution of the compound from Step A above in 1.8 mL of 3:2:1 tetrahydrofuran/methanol/water was added 10 mg of lithium hydroxide monohydrate. The mixture was stirred at room temperature for 1.5 h, and was then concentrated under reduced pressure to afford the title compound as a nearly colorless gum.

Step C: [4-[[[[(3S)-2-[(3R)-3-Amino-4-(2-fluorophenyl)butanoyl]-1,2,3,4-tetrahydroisoquinolin-3-yl]carbonyl]amino]methyl]phenyl]acetic acid, trifluoroacetic acid salt The product from Step B above was suspended in 2 mL of dichloromethane and 1 mL of trifluoroacetic acid was added. After stirring at room temperature for 1 h, the solution was concentrated under reduced pressure and purified by preparative HPLC (YMC Pro C18 column, gradient elution, 10-90% acetonitrile/water containing 0.1% trifluoroacetic acid) to afford the title compound as a white powder. LC/MS: 504.2 (M+1).

EXAMPLE 2

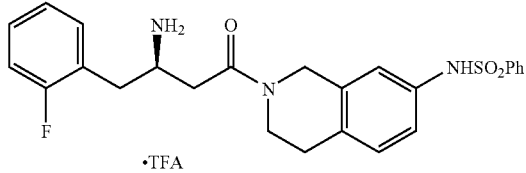

N-[2-[(3R)-3-Amino-4-(2-fluorophenyl)butanoyl]-1,2,3,4-tetrahydroisoguinolin-7-yl]benzenesulfonamide, trifluoroacetic acid salt Step A: 2-[(3R)-3-[(tert-Butoxycarbonyl)amino]-4-(2-fluorophenyl)butanoyl]-7-nitro-1,2,3,4-tetrahydroisoquinoline (3R)-3-[(tert-Butoxycarbonyl)amino]4-(2-fluorophenyl)butanoic acid (0.69 g; 2.34 mmol) and 7-nitro-1,2,3,4 tetrahydroisoquinoline (0.50 g; 2.34 mmol) were treated with EDC (0.54 g, 2.8 mmol), HOBt (0.38 g, 2.8 mmol) and N,N-diisopropylethylamine (0.60 g, 4.67 mmol) essentially following the procedure outlined in Example 1, Step A. Purification by flash chromatography (silica gel; 35% ethyl acetate/hexanes as eluant) afforded the title compound. LC/MS: 358.1 (M+1-BOC)

Step B: 7-Amino-2-[(3R)-3-[(tert-butoxycarbonyl)amino]-4-(2-fluorophenyl)butanoyl]-1,2,3,4-tetrahydroisoquinoline To the product (0.43 g) from Step A above in 4 mL of methanol was added 20% palladium hydroxide on carbon (Pearlman's catalyst, 0.04 g). The reaction was placed under a balloon of hydrogen and allowed to stir at room temperature overnight. The reaction flask was purged, the mixture was filtered and concentrated in vacuo. The residue was purified by flash chromatography (silica gel; 55% ethyl acetate/hexanes) to afford the title compound. LC/MS: 328 (M−100).

Step C: N-[2-[(3R)-3-[(tert-Butoxycarbonyl)amino]-4-(2-fluorophenyl)butanoyl]-1,2,3,4-tetrahydroisoguinolin-7-yl]benzenesulfonamide To an ice-cold solution of the product (0.040 g; 0.09 mmol) from Step B above in dichloromethane (0.5 mL) was added sequentially pyridine (0.011 g, 0.14 mmol) and benzenesulfonyl chloride (0.018 g, 0.103 mmol), and the reaction was then allowed to warm to room temperature overnight. The volatiles were removed under reduced pressure and the residue was purified by flash chromatography (silica gel; 50% ethyl acetate/hexanes as eluant) to afford the title compound. LC/MS: 568.1 (M+1).

Step D: N-[2-[(3R)-3-Amino-4-(2-fluorophenyl)butanoyl]-1,2,3,4-tetrahydroisoguinolin-7-yl]benzenesulfonamide, trifluoroacetic acid salt To the product from Step C was added 1 mL of dichloromethane and 2 mL of trifluoroacetic acid. The reaction was allowed to stand at room temperature for 2 h and the volatiles were removed under reduced pressure to afford the title compound. LC/MS: 468.1: (M+1).

EXAMPLE 3

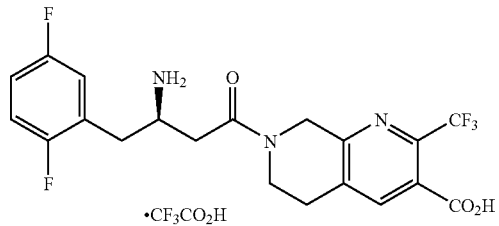

7-[(3R)-3-Amino-4-(2,5-difluorophenyl)butanoyl]-2-(trifluoromethyl)-5-6,7,8-tetrahydro-1,7-naphthyridine-3-carboxylic acid, trifluoroacetic acid salt Step A: Ethyl 7-[(3R)-3-[(tert-butoxycarbonyl)amino]-4-(2,5-difluorophenyl)butanoyl]-2-(trifluoromethyl)-5,6,7,8-tetrahydro-1,7-naphthyridine-3-carboxylate (3R)-3-[(tert-Butoxycarbonyl)amino]-4-(2,5-difluorophenyl)butanoic acid (intermediate 1) and ethyl 2-(trifluoromethyl)-5,6,7,8-tetrahydro-1,7-naphthyridine-3-carboxylate hydrochloride (intermediate 27) were treated with EDC, HOBt and N,N-diisopropylethylamine according to the procedure described for Example 1, Step A to afford the title compound as a white foam.

Step B: 7-[(3R)-3-[(tert-Butoxycarbonyl)amino]-4-(2,5-difluorophenyl)butanoyl]-2-(trifluoromethyl)-5,6,7,8-tetrahydro-1,7-naphthyridine-3-carboxylic acid A solution of the product from Step A above (92 mg, 0.161 mmol) in 1.2 mL of 3:2:1 tetrahydrofuran/methanol/water was treated with lithium hydroxide monohydrate (10 mg) and the solution was stirred at room temperature for 18 h. The volatiles were removed under a stream of nitrogen, and the residue was dissolved in 4 mL of water. The solution was acidified by portionwise addition of citric acid monohydrate, and the product was extracted into ethyl acetate. The combined organic extracts were dried over magnesium sulfate and concentrated to afford the title compound as a white foam.

Step C: 7-[(3R)-3-Amino-4-(2,5-difluorophenyl)butanoyl]-2-(trifluoromethyl)-5,6,7,8-tetrahydro-1,7-naphthyridine-3-carboxylic acid, trifluoroacetic acid salt A solution of the product from Step B above (23 mg) in 3 mL of dichloromethane was treated with 1 mL of trifluoroacetic acid, and the solution was kept at room temperature for 1 h. The volatiles were removed under a stream of nitrogen, and the residue was triturated with ether. The product was collected and dried in vacuo to afford the title compound as a white powder. LC/MS: 444.0 (M+1).

EXAMPLE 4

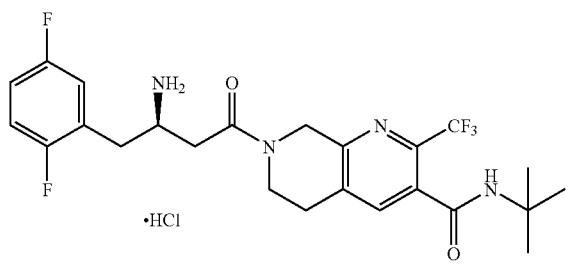

7-[(3R)-3-Amino-4-(2,5-difluorophenyl)butanoyl]-N-(tert-butyl)-2-(trifluoromethyl)-5,6,7,8-tetrahydro-1,7-naphthyridine-3-carboxamide, hydrochloride Step A: 7-[(3R)-3-[(tert-Butoxycarbonyl)amino]-4-(2,5-difluorophenyl)butanoyl]-N-(tert-butyl)-2-(trifluoromethyl)-5,6,7,8-tetrahydro-1,7-naphthyridine-3-carboxamide To a solution of the product (33 mg, 0.061 mmol) from Example 3, Step B, 1-[3-(dimethylamino)propyl]-3-ethylcarbodiimide hydrochloride (EDC; 12 mg, 0.063 mmol), 1-hydroxybenzotriazole (HOBt; 9 mg, 0.067 mmol) and N,N-diisopropylethyl amine (0.026 mL, 0.15 mmol) in 1.0 mL of dichloromethane was added tert-butylamine (0.011 mL, 0.100 mmol). The solution was stirred at room temperature for 18 h. The reaction mixture was subjected directly to flash chromatography (silica gel; 35 to 75% ethyl acetate/hexanes step-gradient elution) to afford the title compound as a white foam.

Step B: 7-[(3R)-3-Amino-4-(2,5-difluorophenyl)butanoyl]-N-(tert-butyl)-2-(trifluoromethyl)-5,6,7,8-tetrahydro-1,7-naphthyridine-3-carboxamide, hydrochloride A solution of the product (25 mg) from Step A above, 0.5 mL of methanol and 2.5 mL of 4.0M hydrogen chloride in 1,4-dioxane was kept at room temperature for 18 h. The volatiles were removed under a stream of nitrogen, and the residue was triturated with ether. The resultant precipitate was collected and dried in vacuo to afford the title compound as a white powder. LC/MS: 499.1 (M+1).

EXAMPLE 5

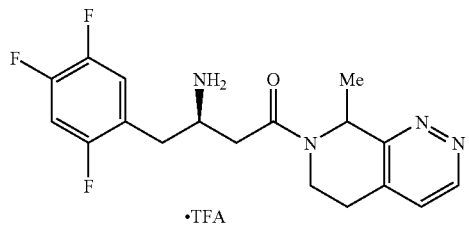

7-[(3R)-3-Amino-4-(2,4,5-trifluorophenyl)butanoyl]-8-methyl-5,6,7,8-tetrahydropyrido[3,4-c]pyridazine, trifluoroacetic acid salt Step A: 7-[(3R)-3-[(tert-Butoxycarbonyl)amino]-4-(2,4,5-trifluorophenyl)butanoyl]-8-methyl-5,6,7,8-tetrahydropyrido[3,4-c]pyridazine To a solution of 73.9 mg (0.281 mmol) of 8-methyl-5,6,7,8-tetrahydropyrido[3,4-c]pyridazine, trifluoroacetate salt (Intermediate 34), 93.6 mg (0.281 mmol) of (3R)-3-[(tert-butoxycarbonyl)amino]4-(2,4,5-trifluorophenyl)butanoic acid (Intermediate 3) and 0.150 mL (0.843 mmol) of N,N-diisopropylethylamine in 2.5 ml of DMF were added O-(7-azabenzotriazol-yl)-N,N,N',N'-tetra-methyluronium hexafluorophosphate (HATU; 128 mg, 0.337 mmol), 1-hydroxy-7-azabenzotriazole (HOAt; 45.9 mg, 0.337 mmol). The reaction was stirred at room temperature for 18 h. Then the reaction mixture was partitioned between ethyl acetate and 0.5M aqueous sodium bicarbonate solution. The aqueous phase was extracted with three portions of ethyl acetate. The combined organic phase was washed with brine, dried over magnesium sulfate and concentrated in vacuo. The mixture was purified by preparative TLC (100% ethyl acetate), then by chiral HPLC (ChiralCell OJ column, 14% ethanol/hexanes) to afford the title compound as a solid. The slower eluting isomer was used in Step B below. LC/MS: 409 (M+1-56).

Step B: 7-[(3R)-3-Amino-4-(2,4,5-trifluorophenyl)butanoyl]-8-methyl-5,6,7,8 tetrahydropyrido[3,4-c]pyridazine, trifluoroacetic acid salt The title compound was prepared from 7-[(3R)-3-[(tert-butoxycarbonyl)amino]-4-(2,4,5-trifluorophenyl)butanoyl]-

8-methyl-5,6,7,8-tetrahydropyrido[3,4-c]pyridazine (Step A) using a procedure analogous to that of Example 1, Step C to give the title compound as a solid. LC/MS: 365 (M+1).

EXAMPLE 6

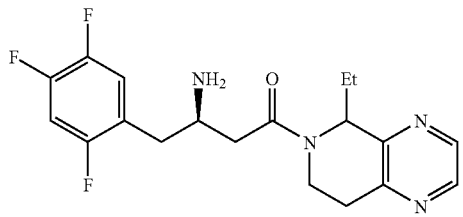

6-[(3R)-3-Amino-4-(2,4,5-trifluorophenyl)butanoyl]-5-ethyl-5,6,7,8-tetrahydropyrido[3,4-b]pyrazine Step A: 6-[(3R)-3-(tert-Butoxycarbonylamino)-4-(2,4,5-trifluorophenyl)butanoyl]-5-ethyl-5,6,7,8-tetrahydropyrido[3,4-b]pyrazine 5-Ethyl-5,6,7,8-tetrahydropyrido[3,4-b]pyrazine dihydrochloride (Intermediate 32, 26 mg, 0.11 mmol) was dissolved in N,N-dimethylformamide (DMF, 0.75 mL) containing N,N-diisopropylethylamine (0.046 mL, 34 mg, 0.26 mmol). (3R)-3-(tert-Butoxycarbonylamino)4 (2,4,5-trifluorophenyl)butanoic acid (Intermediate 3, 36 mg, 0.11 mmol), 1-hydroxybenzotriazole (16 mg, 0.12 mmol), and a portion of molecular sieve pellets (4 Å) were added, followed 10 min later by 1-[3-(dimethylamino)propyl]-3-ethylcarbodiimide hydrochloride (33 mg, 0.17 mmol). After stirring for 16 h at room temperature, the mixture was partitioned between ethyl acetate (25 mL) and saturated aqueous sodium bicarbonate solution (10 mL). The organic layer was washed with saturated aqueous brine (10 mL) and the aqueous layers were extracted in succession with ethyl acetate (25 mL). The organic layers were dried over sodium sulfate, decanted, and evaporated. Purification by flash column chromatography (silica gel, 15-20% ethyl aceate/0.75-1.0% methanol/dichloromethane) gave the title compound as a mixture of diastereomers. Separation was accomplished by EPLC using a Chiralcel OJ column, eluting with 8% ethanol in hexanes. The first-eluting diastereomer was used in Step B to produce the more active final product. LC/MS: 501 (M+Na).

Step B: 6-[(3R)-3-Amino-4-(2,4,5-trifluorophenyl)butanoyl]-5-ethyl-5,6,7,8-tetrahydropyrido[3,4-b]pyrazine A solution of methanolic hydrogen chloride (approx. 1.6M, 1.5 mL) was added to 6-[(3R)-3-(tert-butoxycarbonylamino)-4-(2,4,5-trifluorophenyl)butanoyl]-5-ethyl-5,6,7,8-tetrahydropyrido[3,4-b]pyrazine (18 mg, 0.038 mmol) dissolved in 0.25 mL of methanol. After 2.5 h, the solution was added to saturated aqueous sodium bicarbonate solution (10 mL), which was then extracted with two portions of ethyl acetate (25 mL and 15 mL). The organic layers were washed in succession with saturated aqueous brine (5 mL), dried over sodium sulfate, decanted, and concentrated. The residue was dissolved in methanol, and the resulting solution was filtered (0.45 micron PTFE membrane) and evaporated to provide the title compound as a very viscous colorless syrup. LC/MS: 379 (M+1).

Essentially following the procedures outlined for Examples 1-6, the compounds listed in Tables 2 and 3 were prepared.

TABLE 2

| Example | $R^2$ | $R^9$ | MS (M + 1) |
|---|---|---|---|
| 7 | 2-F,5-F | pyrrolidin-1-ylcarbonyl | 428.2 |
| 8 | 2-F | piperidin-1-ylcarbonyl | 424.0 |
| 9 | 2-F | 4-[(methoxycarbonyl)methyl]benzylaminocarbonyl | 518.3 |
| 10 | 2-F | 4-[(benzyloxy)carbonyl]piperazin-1-ylcarbonyl | 559.0 |
| 11 | 2-F,5-F | 4-[(benzyloxy)carbonyl]piperazin-1-ylcarbonyl | 577.3 |

TABLE 3

| Ex. | $R^2$ | $R^8$ | W | X | Y | Z | MS (M + 1) |
|---|---|---|---|---|---|---|---|
| 12 | 2-F,5-F | H | C—H | C—H | C—H | C—H | 331.2 |
| 13 | 2-F,5-F | H | C—H | C—OMe | C—OMe | C—H | 391.2 |
| 14 | 2-F,5-F | H | C—H | C—H | C—CN | C—H | 356.2 |
| 15 | 2-F,5-F | H | C—H | C—$CO_2$Me | C—H | C—H | 389.2 |
| 16 | 2-F,5-F | H | C—H | C—$CO_2$H | C—H | C—H | 375.2 |
| 17 | 2-F | H | C—H | C—NHAc | C—H | C—H | 370.1 |
| 18 | 2-F | H | C—H | C—$NHSO_2$Me | C—H | C—H | 406.2 |
| 19 | 3-F,4-F | H | C—H | C—$NHSO_2$Me | C—H | C—H | 424.2 |

TABLE 3-continued

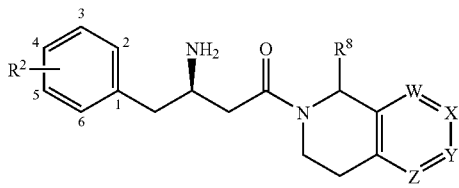

| Ex. | R² | R⁸ | W | X | Y | Z | MS (M + 1) |
|---|---|---|---|---|---|---|---|
| 20 | 3-F,4-F | H | C—H | C—NHSO₂Ph | C—H | C—H | 486.2 |
| 21 | 2-F,5-F | H | C—H | C—CF₃ | C—H | C—H | 399.0 |
| 22 | 2-F,5-F | H | C—H | C—H | C—OH | C—H | 347.2 |
| 23 | 2-F,5-F | H | C—H | C—H | C—H | C—OH | 347.2 |
| 24 | 2-F,5-F | H | C—H | C—SO₂NH₂ | C—H | C—H | 410.1 |
| 25 | 2-F,5-F | H | C—H | N | C—H | N | 333.1 |
| 26 | 2-F,5-F | H | C—H | N | C-Me | N | 347.1 |
| 27 | 2-F,5-F | H | C—H | N | C—CF₃ | N | 401.1 |
| 28 | 2-F,5-F | H | C—OH | N | C—CF₃ | N | 417.1 |
| 29 | 2-F,5-F | H | C—H | C—CO₂Et | C—CF₃ | N | 472.1 |
| 30 | 2-F,5-F | H | C—H | C—CO₂H | C—CF₃ | N | 444.1 |
| 31 | 2-F,5-F | H | C—H | C—CO₂Me | C—CF₃ | N | 458.2 |
| 32 | 2-F,5-F | H | C—H | C—CO₂Et | C—H | N | 404 |
| 33 | 2-F,5-F | H | C—H | C—CO₂H | C—H | N | 376.2 |
| 34 | 3-F,4-F | H | C—H | C—CO₂H | C—Cl | N | 410 |
| 35 | 2-F,5-F | H | C—H | C—CO₂Et | C—Cl | N | 438.2 |
| 36 | 2-F,5-F | H | C—H | C—CO₂H | C—Cl | N | 410.1 |
| 37 | 2-F,5-F | H | C—H | C—CO₂Et | C—OH | N | 420.0 |
| 38 | 2-F,5-F | H | C—H | C—CO₂H | C—OH | N | 392.1 |
| 39 | 2-F,5-F | H | C—H | C—H | C—CF₃ | N | 400.1 |
| 40 | 2-F,5-F | H | C—H | C—CF₃ | C—H | N | 400.0 |
| 41 | 2-F,5-F | H | C—H | C-[5-(trifluoro-methyl)oxadiazol-3-yl] | C—H | N | 468.1 |
| 42 | 2-F,5-F | H | N | C—CF₃ | C—H | C—H | 400.0 |
| 43 | 2-F,4-F,5-F | H | C—H | C—CF₃ | N | OMe | 448.0 |
| 44 | 2-F,4-F,5-F | H | N | N | C-Ph | N | 428 |
| 45 | 2-F,4-F,5-F | H | N | N | C-Me | N | 366 |
| 46 | 2-F,4-F,5-F | H | N | N | C-(4-F-Ph) | N | 446 |
| 47 | 2-F,4-F,5-F | H | N | N | C-cyclopropyl | N | 392 |
| 48 | 2-F,4-F,5-F | H | N | N | C—CF₃ | N | 420 |
| 49 | 2-F,4-F,5-F | H | N | C-(4-F-Ph) | N | N | 446 |
| 50 | 2-F,4-F,5-F | Me | N | C—H | C—H | N | 365 |

EXAMPLE OF A PHARMACEUTICAL FORMULATION

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

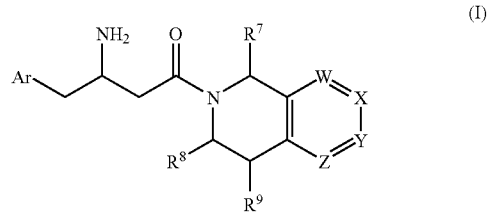

(I)

or a pharmaceutically acceptable salt thereof; wherein
each n is independently 0, 1, or 2;
W, X, Y, and Z are each independently N or CR¹;
with the proviso that at least one and only one of W, X, Y and Z is N;
Ar is phenyl substituted with one to five R² substituents;

each $R^1$ is independently selected from the group consisting of
hydrogen,
halogen,
hydroxy,
cyano,
$C_{1-10}$ alkyl, wherein alkyl is unsubstituted or substituted with one to five substituents independently selected from halogen or hydroxy,
$C_{1-10}$ alkoxy, wherein alkoxy is unsubstituted or substituted with one to five substituents independently selected from halogen or hydroxy,
$C_{1-10}$ alkylthio, wherein alkylthio is unsubstituted or substituted with one to five substituents independently selected from halogen or hydroxy,
$C_{2-10}$ alkenyl, wherein alkenyl is unsubstituted or substituted with one to five substituents independently selected from halogen, hydroxy, COOH, and $COOC_{1-6}$ alkyl,
$(CH_2)_n COOH$,
$(CH_2)_n COOC_{1-6}$ alkyl,
$(CH_2)_n CONR^3R^4$, wherein $R^3$ and $R^4$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, $C_{1-6}$ alkoxy, $(CH_2)_n COOH$, and $(CH_2)_n COOC_{1-6}$ alkyl, wherein alkyl and alkoxy are unsubstituted or substituted with one to five halogens;
or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOH$, $(CH_2)_n COOC_{1-6}$ alkyl, $C_{1-6}$ alkyl, and $C_{1-6}$ alkoxy, wherein alkyl and alkoxy are unsubstituted or substituted with phenyl or one to five halogens;
$(CH_2)_n$—$NR^3R^4$,
$(CH_2)_n$—$OCONR^3R^4$,
$(CH_2)_n$—$SO_2NR^3R^4$,
$(CH_2)_n$—$SO_2R^5$,
$(CH_2)_n$—$NR^6SO_2R^5$,
$(CH_2)_n$—$NR^6CONR^3R^4$,
$(CH_2)_n$—$NR^6COR^6$,
$(CH_2)_n$—$NR^6CO_2R^5$,
$(CH_2)_n$—$COR^6$,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-aryl, wherein aryl is unsubstituted or substituted with one to five substituents independently selected from halogen, cyano, hydroxy, $NR^6SO_2R^5$, $SO_2R^5$, $CO_2H$, $COOC_{1-6}$ alkyl, $C_{1-6}$ alkyl, and
$C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens;
each $R^2$ is independently selected from the group consisting of
hydrogen,
halogen,
cyano,
hydroxy,
$C_{1-6}$ alkyl, unsubstituted or substituted with one to five halogens, and
$C_{1-6}$ alkoxy, unsubstituted or substituted with one to five halogens;
each $R^5$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^5$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
each $R^6$ is hydrogen or $R^5$;
$R^7$, $R^8$, and $R^9$ are each independently selected from the group consisting of
hydrogen,
cyano,
$(CH_2)_n COOH$,
$(CH_2)_n COOC_{1-6}$ alkyl,
$C_{1-10}$ alkyl, unsubstituted or substituted with one to five substituents independently selected from halogen, hydroxy, $C_{1-6}$ alkoxy,
and phenyl-$C_{1-3}$ alkoxy, wherein alkoxy is unsubstituted or substituted with one to five halogens,
$(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and $(CH_2)_n CONR^3R^4$, wherein $R^3$ and $R^4$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, $C_{1-6}$ alkoxy, $(CH_2)_n COOH$, and $(CH_2)_n COOC_{1-6}$ alkyl, wherein alkyl and alkoxy are unsubstituted or substituted with one to five halogens;

or $R^3$ and $R^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOH$, $(CH_2)_n COOC_{1-6}$ alkyl, $C_{1-6}$ alkyl, and $C_{1-6}$ alkoxy, wherein alkyl and alkoxy are unsubstituted or substituted with phenyl or one to five halogens; and wherein any methylene ($CH_2$) carbon atom in $R^7$, $R^8$ or $R^9$ is unsubstituted or substituted with one to two groups independently selected from halogen, hydroxy, and $C_{1-4}$ alkyl unsubstituted or substituted with one to five halogens.

2. The compound of claim 1 of structural formula Ia wherein the carbon atom marked with an * has the R configuration

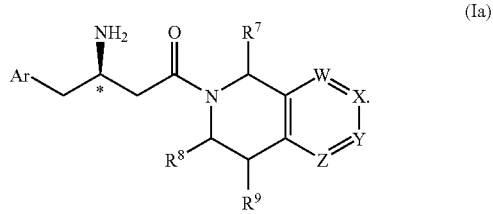

(Ia)

3. The compound of claim 1 of structural formula Ie:

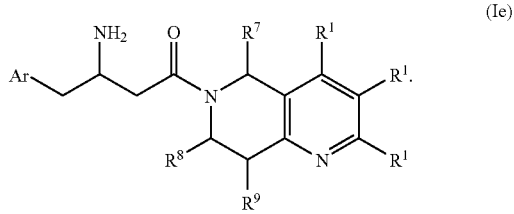

(Ie)

4. The compound of claim 3 of structural formula If wherein the carbon atom marked with an * has the R configuration:

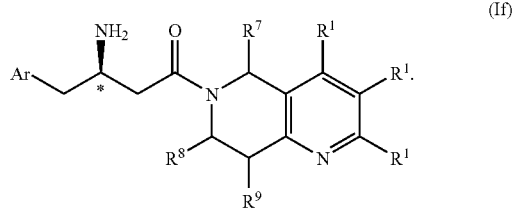

(If)

5. The compound of claim 3 wherein $R^8$ and $R^9$ are hydrogen.

6. The compound of claim 1 of structural formula Ih:

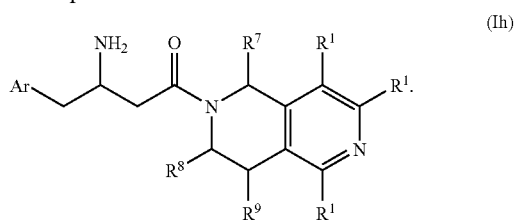

(Ih)

7. The compound of claim 6 of structural formula Ii wherein the carbon atom marked with an * has the R configuration:

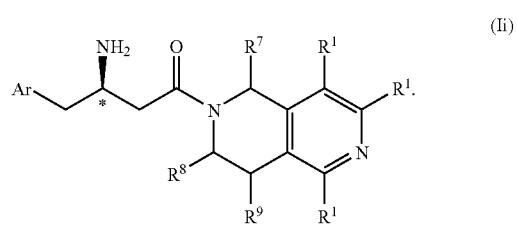

(Ii)

8. The compound of claim 6 wherein $R^8$ and $R^9$ are hydrogen.

9. The compound of claim 1 of structural formula Ik:

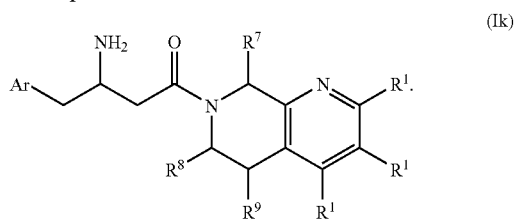

(Ik)

10. The compound of claim 9 of structural formula Il wherein the carbon atom marked with an * has the R configuration:

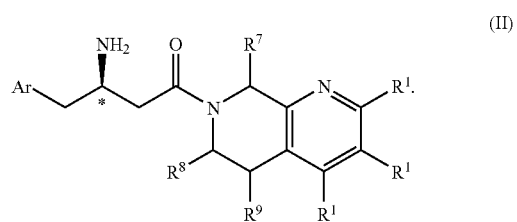

(Il)

11. The compound of claim 9 wherein $R^8$ and $R^9$ are hydrogen.

12. The compound of claim 1 wherein $R^2$ is selected from the group consisting of hydrogen, fluoro, chloro, bromo, trifluoromethyl, and methyl.

13. The compound of claim 1 wherein $R^1$ is selected from the group consisting of:
hydrogen,
halogen,
hydroxy,
cyano,
$C_{1-10}$ alkyl, wherein alkyl is unsubstituted or substituted with one to five substituents independently selected from halogen or hydroxy,
$C_{1-10}$ alkoxy, wherein alkoxy is unsubstituted or substituted with one to five substituents independently selected from halogen or hydroxy,
$(CH_2)_n COOH$, (CH$_2$)$_n$COOC$_{1-6}$ alkyl,
(CH$_2$)$_n$CONR$^3$R$^4$, wherein R$^3$ and R$^4$ are independently selected from the group consisting of hydrogen, tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, C$_{1-6}$ alkoxy, (CH$_2$)$_n$COOH, and (CH$_2$)$_n$COOC$_{1-6}$ alkyl, wherein alkyl and alkoxy are unsubstituted or substituted with one to five halogens;
or R$^3$ and R$^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, (CH$_2$)$_n$COOC$_{1-6}$ alkyl, C$_{1-6}$ alkyl, and C$_{1-6}$ alkoxy, wherein alkyl and alkoxy are unsubstituted or substituted with phenyl or one to five halogens;
(CH$_2$)$_n$—SO$_2$NR$^3$R$^4$,
(CH$_2$)$_n$—NR$^6$SO$_2$R$^5$,
(CH$_2$)$_n$—NR$^6$COR$^6$,
(CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens,
(CH$_2$)$_n$-aryl, wherein aryl is unsubstituted or substituted with one to five substituents independently selected from halogen, cyano, hydroxy, NR$^6$SO$_2$R$^5$, SO$_2$R$^5$, CO$_2$H, COOC$_{1-6}$ alkyl, C$_{1-6}$ alkyl, and C$_{1-6}$ alkoxy, wherein alkyl and alkoxy are unsubstituted or substituted with one to five halogens,
(CH$_2$)$_n$-heteroaryl, wherein heteroaryl is unsubstituted or substituted with one to three substituents independently selected from hydroxy, halogen, C$_{1-6}$ alkyl, and C$_{1-6}$ alkoxy, wherein alkyl and alkoxy are unsubstituted or substituted with one to five halogens, and
wherein any methylene (CH$_2$) carbon atom in R$^1$ is unsubstituted or substituted with one to two groups independently selected from halogen, hydroxy, and C$_{1-4}$ alkyl unsubstituted or substituted with one to five halogens.

14. The compound of claim 13 wherein R$^1$ is selected from the group consisting of
hydrogen,
methyl,
trifluoromethyl,
phenyl,
4-fluorophenyl,
cyclopropyl,
chloro,
methoxy,
hydroxy,
cyano,
methoxycarbonyl,
ethoxycarbonyl,
tert-butylaminocarbonyl,
carboxy,
acetamido,
methanesulfonylamino,
benzenesulfonylamino,
aminosulfonyl, and
5-(trifluoromethyl)oxadiazol-3-yl.

15. The compound of claim 1 wherein R$^7$, R$^8$, and R$^9$ are each independently selected from the group consisting of:
hydrogen,
C$_{1-10}$ alkyl, unsubstituted or substituted with one to five substituents independently selected from halogen, hydroxy, C$_{1-6}$ alkoxy, and phenyl-C$_{1-3}$ alkoxy, wherein alkoxy is unsubstituted or substituted with one to five halogens, and
(CH$_2$)$_n$CONR$^3$R$^4$, wherein R$^3$ and R$^4$ are independently selected from the group consisting of hydrogen, tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, C$_{1-6}$ alkoxy, (CH$_2$)$_n$COOH, and (CH$_2$)$_n$COOC$_{1-6}$ alkyl, wherein alkyl and alkoxy are unsubstituted or substituted with one to five halogens;
or R$^3$ and R$^4$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, (CH$_2$)$_n$COOC$_{1-6}$ alkyl, C$_{1-6}$ alkyl, and C$_{1-6}$ alkoxy, wherein alkyl and alkoxy are unsubstituted or substituted with phenyl or one to five halogens; and
wherein any methylene (CH$_2$) carbon atom in R$^7$, R$^8$ or R$^9$ is unsubstituted or substituted with one to two groups independently selected from halogen, hydroxy, and C$_{1-4}$ alkyl unsubstituted or substituted with one to five halogens.

16. The compound of claim 15 wherein R$^7$, R$^8$, and R$^9$ are each independently selected from the group consisting of
hydrogen,
methyl,
ethyl,
[[4-(carboxymethyl)phenyl]methyl]aminocarbonyl,
pyrrolidin-1-ylcarbonyl,
piperidin-1-ylcarbonyl,
4-[(methoxycarbonyl)methyl]benzylaminocarbonyl, and
4-[(benzyloxy)carbonyl]piperazin-1-ylcarbonyl.

17. The compound of claim 16 wherein R$^7$ and R$^9$ are hydrogen.

18. The compound of claim 16 wherein R$^8$ and R$^9$ are hydrogen.

19. The compound of claim 18 wherein R$^7$ is hydrogen.

20. The compound of claim 16 which is selected from the group consisting of:

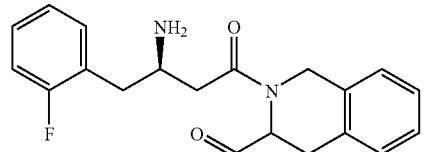

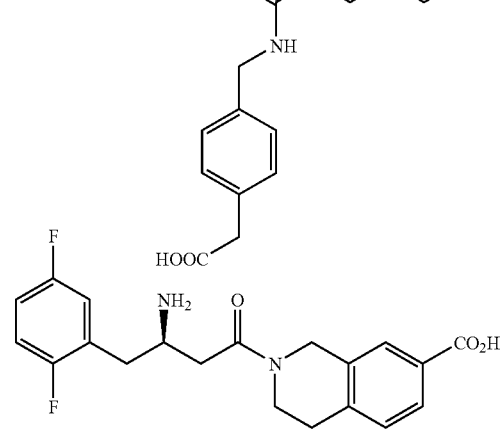

-continued

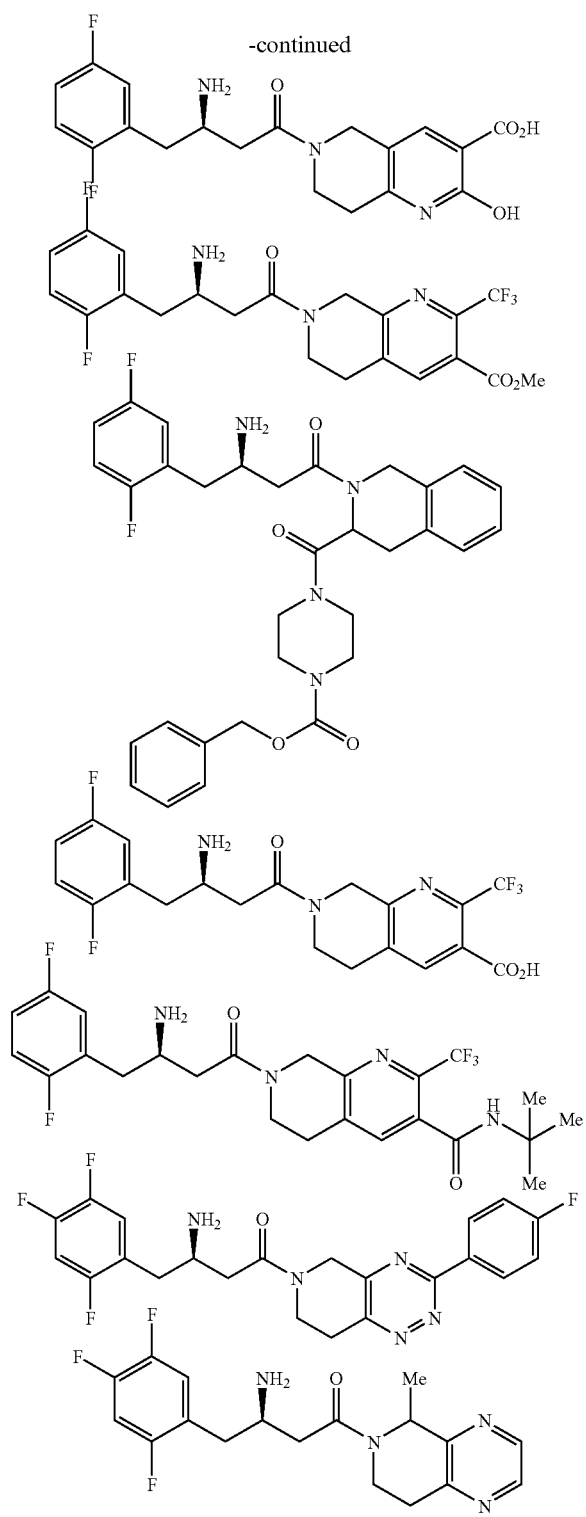
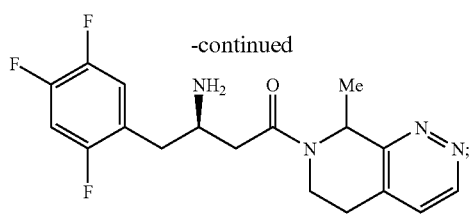

or a pharmaceutically acceptable salt thereof.

21. A pharmaceutical composition which comprises a compound of claim 1 and a pharmaceutically acceptable carrier.

22. A method for treating non-insulin dependent (Type 2) diabetes in a mammal in need thereof which comprises the administration to the mammal of a therapeutically effective amount of a compound of claim 1.

23. A method for treating hyperglycemia in a mammal in need thereof which comprises the administration to the mammal of a therapeutically effective amount of a compound of claim 1.

24. The pharmaceutical composition of claim 21 further comprising one or more additional active ingredients selected from the group consisting of:
   (a) a second dipeptidyl peptidase IV inhibitor;
   (b) an insulin sensitizer selected from the group consisting of a PPARγ agonist, a PPARα/γ dual agonist, a PPARα agonist, a biguanide, and a protein tyrosine phosphatase-1B inhibitor;
   (c) an insulin or insulin mimetic;
   (d) a sulfonylurea or other insulin secretagogue;
   (e) an α-glucosidase inhibitor;
   (f) a glucagon receptor antagonist;
   (g) GLP-1, a GLP-1 mimetic, or a GLP-1 receptor agonist;
   (h) GIP, a GIP mimetic, or a GIP receptor agonist;
   (i) PACAP, a PACAP mimetic, or a PACAP receptor agonist;
   (j) a cholesterol lowering agent selected from the group consisting of (i) HMG-CoA reductase inhibitor, (ii) sequestrant, (iii) nicotinyl alcohol, nicotinic acid or a salt thereof, (iv) PPARα agonist, (v) PPARα/γ dual agonist, (vi) inhibitor of cholesterol absorption, (vii) acyl CoA:cholesterol acyltransferase inhibitor, and (viii) anti-oxidant;
   (k) a PPARδ agonist;
   (l) an antiobesity compound;
   (m) an ileal bile acid transporter inhibitor;
   (n) an anti-inflammatory agent; and
   (o) an antihypertensive agent.

* * * * *